United States Patent
Ivachtchenko et al.

(10) Patent No.: US 9,790,207 B2
(45) Date of Patent: Oct. 17, 2017

(54) PAN-GENOMIC INHIBITORS OF NS5A PROTEIN ENCODED BY HCV, PHARMACEUTICAL COMPOSITIONS, INTERMEDIATES FOR INHIBITOR SYNTHESIS, AND THEIR SYNTHESIS AND APPLICATION METHODS

(71) Applicants: Alexandre Vasilievich Ivachtchenko, Encinitas, CA (US); Andrey Alexandrovich Ivashchenko, Moscow (RU); Nikolay Filippovich Savchuk, Rancho Santa Fe, CA (US); ALLA CHEM, LLC, Carson City, NV (US)

(72) Inventors: Alexandre Vasilievich Ivachtchenko, Encinitas, CA (US); Oleg Dmitrievich Mitkin, Khimki (RU)

( * ) Notice: Subject to any disclaimer, the term of this patent is extended or adjusted under 35 U.S.C. 154(b) by 0 days.

(21) Appl. No.: 14/845,333

(22) Filed: Sep. 4, 2015

(65) Prior Publication Data
US 2017/0066746 A1    Mar. 9, 2017

(51) Int. Cl.
  *C07D 403/14*    (2006.01)
  *A61K 31/4178*   (2006.01)
  (Continued)

(52) U.S. Cl.
  CPC ........ *C07D 403/14* (2013.01); *A61K 31/4178* (2013.01); *A61K 31/427* (2013.01);
  (Continued)

(58) Field of Classification Search
  None
  See application file for complete search history.

(56) References Cited

U.S. PATENT DOCUMENTS

| | | | | |
|---|---|---|---|---|
| 2010/0158862 A1* | 6/2010 | Kim | .................. | C07D 403/14 424/85.2 |
| 2013/0253008 A1* | 9/2013 | Ivachtchenko | ...... | C07D 403/04 514/316 |

OTHER PUBLICATIONS

Ivachtchenko et al., J. Med. Chem. 57, 7716-30 (2014).*

* cited by examiner

Primary Examiner — Theodore R West

(57) ABSTRACT

Compound represented by formula 1:

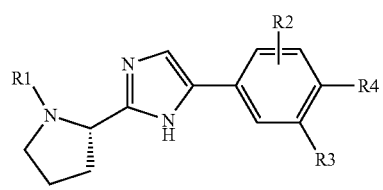

or a pharmaceutically acceptable salt, a hydrate, a crystalline form, or a stereoisomer thereof, wherein:

R1 is hydrogen, tert-butoxycarbonyl,

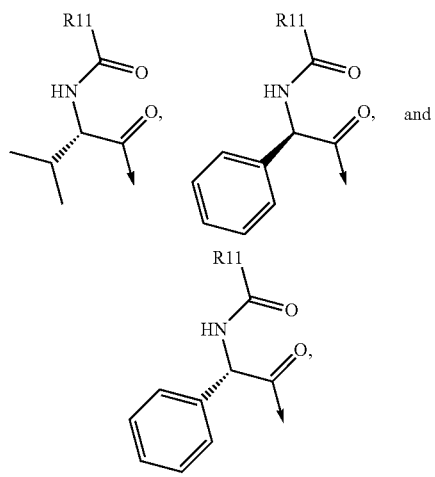

where R11 is an optionally substituted $C_1$-$C_6$ alkyl, an optionally substituted $C_3$-$C_6$ cycloalkyl, or an optionally substituted $C_1$-$C_6$ alkyloxy, and arrows (←) indicate the position of substituents attachment;

R2 is hydrogen, halogen, or $C_1$-$C_4$alkyl;

R3 is an optionally substituted aryl, an optionally substituted aryloxy, an optionally substituted arylsulfanyl, an optionally substituted arylamino, or an optionally substituted nitrogen hetaryl;

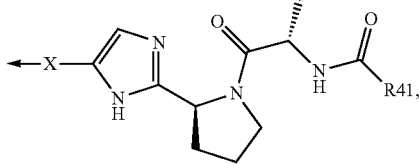

(Continued)

-continued
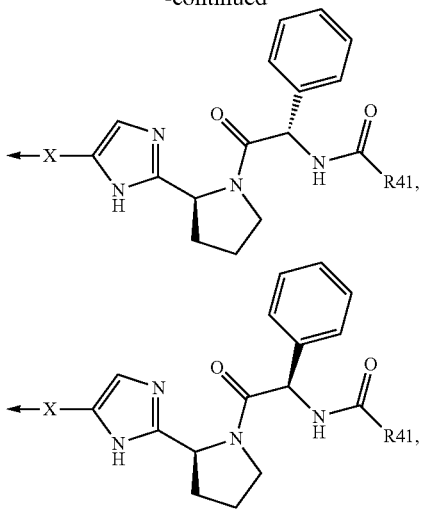
where R41 is an optionally substituted $C_1$-$C_6$ alkyl, an optionally substituted $C_3$-$C_6$ cycloalkyl, or an optionally substituted $C_1$-$C_6$ alkyloxy; X is buta-1,3-diynylene or 1,4-phenylene; arrows (←) indicate the position of substituents attachment.
10 Claims, No Drawings
(51) Int. Cl.
A61K 31/496 (2006.01)
C07D 401/14 (2006.01)
A61K 31/4439 (2006.01)
A61K 45/06 (2006.01)
A61K 38/21 (2006.01)
A61K 31/7056 (2006.01)
A61K 38/48 (2006.01)
A61K 31/427 (2006.01)
(52) U.S. Cl.
CPC ........ A61K 31/4439 (2013.01); A61K 31/496 (2013.01); A61K 31/7056 (2013.01); A61K 38/21 (2013.01); A61K 38/482 (2013.01); A61K 45/06 (2013.01); C07D 401/14 (2013.01); C12Y 304/21 (2013.01)

PAN-GENOMIC INHIBITORS OF NS5A PROTEIN ENCODED BY HCV, PHARMACEUTICAL COMPOSITIONS, INTERMEDIATES FOR INHIBITOR SYNTHESIS, AND THEIR SYNTHESIS AND APPLICATION METHODS

FIELD OF THE INVENTION

The present invention relates to novel antiviral agents and intermediates for their synthesis. More specifically, the present invention relates to compounds that are pan-genomic inhibitors of NS5A protein encoded by Hepatitis C virus (HCV), pharmaceutical compositions comprising such compounds, methods for inhibiting HCV viral replication, and methods for treating or preventing HCV infection. The present invention also relates to novel substituted imidazoles useful as intermediates for the synthesis of antiviral agents disclosed herein. The invention also relates to processes for making the compounds.

BACKGROUND OF THE INVENTION

Hepatitis C infection caused by HCV is among the most common liver diseases; widespread throughout the world. On the basis of annual World Health Organization (WHO) reports, more than 130-150 million people are infected and more than 350-500 K individuals die from HCV-related liver pathologies [WHO fact sheet N0 164. Hepatitis C; World Health Organization: Geneva, updated July 2013]. In accordance with the Centers for Disease Control and Prevention statistical estimation, approximately 3.2 million people chronically infected in the USA [Hepatitis C. Information for Health Professionals; Centers for E Control: Atlanta]. Acute disease states are frequently observe long-term and asymptomatic periods. Approximately 75-85% of newly infected persons become chronically infected. Among these patients, 60-70% will suffer chronic liver disease. In 5-20% of cases, cirrhosis or liver cancer is diagnosed, resulting in 1-5% lethal outcomes. It is not surprising that HCV is the leading indication for liver transplantation [Germani, G. et al. HCV in liver transplantation. Semin. Immunopathol. 2013, 35 (1), 101-110].

Based on the foregoing, there exists a significant need to identify compounds that are pan-genomic inhibitors of the NS5A protein encoded by HCV.

A number of NS5A inhibitors are currently undergoing clinical trials or already used for the treatment of hepatitis C including Daclatasvir (BMS-790052) [Belema, M. et al. *J. Med. Chem.* 57, 1643-1672, 2014, WO 2008/021927, WO 2008/021928, WO-2008/021936], Ledipasvir (GS-5885) [Link, J. et al. *J. Med. Chem.* 57, 2033-2046, 2014, WO 2010/132601], Ombitasvir (ABT-267) [DeGoey, et al. *J. Med. Chem.* 57, 2047-2057, 2014, WO 2010/144646], Elbasvir (MK-8742) [Coburn, C. A. et al. *Chem Med Chem.* 8, 1930-1940, 2013, WO 2012/040923, WO 2012/041014], Hepavivir (AV-4025) [Ivathtchenko, A. V. et al. J. Med. Chem. 57, 7716-30, 2014, WO 2012/074437] (Table 1).

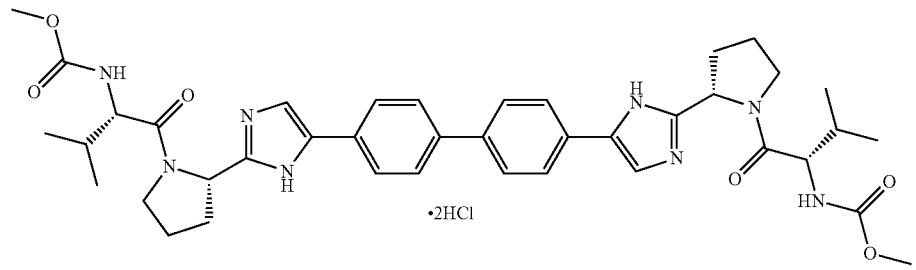

Declatasvir (BMA-790052)

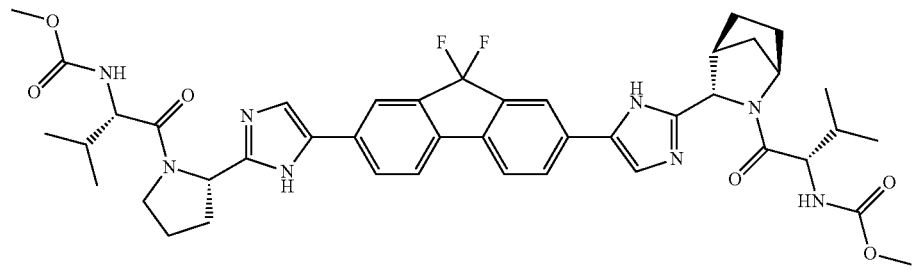

Ledipasvir (GS-5885)

-continued
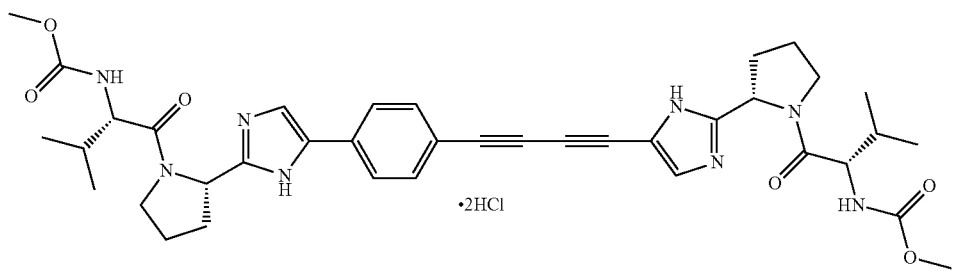
AV-4025
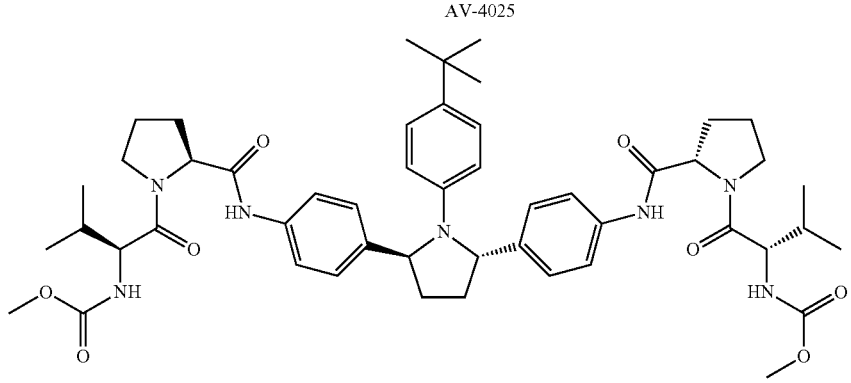
Ombitasvir (ABT-267)
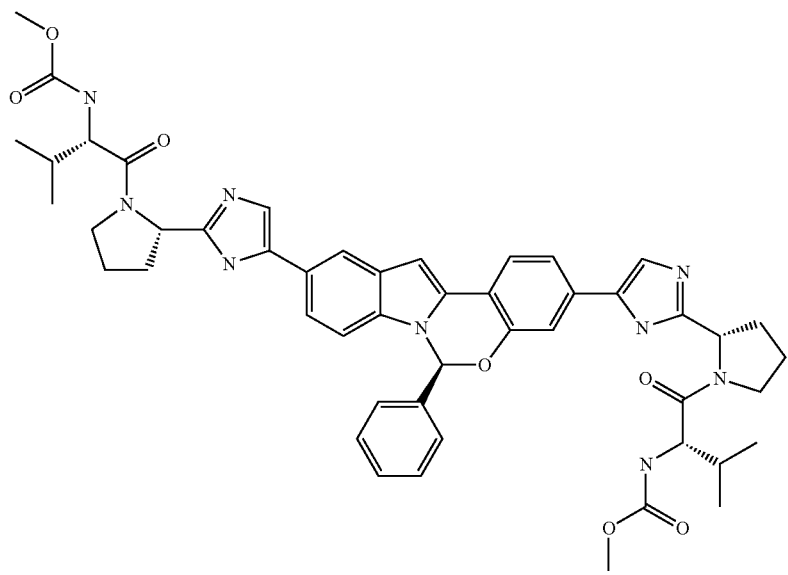
Elbasvir (MK-8742)
TABLE 1
The activity and bioavailability of known HCV NS5A inhibitors.
| NS5A inhibitors | EC$_{50}$, pM HCV Genotype NS5A | | | | | | Bioavailability in rat, F, % |
|---|---|---|---|---|---|---|---|
| | GT1a | GT1b | GT2a | GT3a | GT4a | GT5a | |
| Daclatasvir (BMS-790052), BMS[a] | 50 | 9 | 71 | 103 | 12 | 33 | 11.0[b] |
| Ledipasvir (GS-5885), Giliad[c] | 31[a] | 5[a] | 20,800[a] | 10,100[a] | 7[a] | | 32.5 |
| AV-4025, AllaChem[d] | 59[b] | 3.4[d] | 51[b] | 2,569 | 12 | 172 | 65.0 |

TABLE 1-continued

The activity and bioavailability of known HCV NS5A inhibitors.

| NS5A inhibitors | EC$_{50}$, pM HCV Genotype NS5A | | | | | | Bioavailability in rat, F, % |
|---|---|---|---|---|---|---|---|
| | GT1a | GT1b | GT2a | GT3a | GT4a | GT5a | |
| Ombitasvir (ABT-267), Abbot[a,e] | 14.1 | 5 | 12.4 | 19.3 | 1.7 | 4.3 | 6.2 |
| Elbasvir (MK-8742), Merck[a,f] | 4 | 3 | 3 | 20 | 3 | | 9.0 |

[a]Belema, M. et al. (2014) *J. Med. Chem.* 57, 1643-1672.
[b][hyperlink removed]
[c]Link, J. et al. (2014) *J. Med. Chem.* 57, 2033-2046.
[d]Ivachtchenko, A. V. et al. (2014) *J. Med. Chem.* 57, 7716-7730.
[e]DeGoey, et al. (2014). *J. Med. Chem.* 57, 2047-2057.
[f]Coburn, C. A. et al. (2013). *ChemMedChem.* 8, 1930-1940.

However, known inhibitors possess some drawbacks. Thus, the pan-genomic HCV NS5A inhibitors Daclatasvir, Ombitasvir, and Elbasvir have limited bioavailability (Table 1), and Ledipasvir and AV-4025 have insufficient activities against GT3a and GT5a of HCV NS5A. In this context, searching for new pan-genomic HCV NS5A inhibitors with improved characteristics is an important task.

DISCLOSURE OF THE INVENTION

The present invention relates to a novel compound of formula (1):

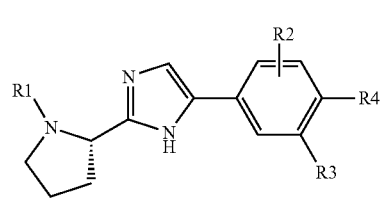

or a pharmaceutically acceptable salt, a hydrate, a crystalline form, or a stereoisomer thereof, wherein:
R1 is hydrogen, tert-butoxycarbonyl,

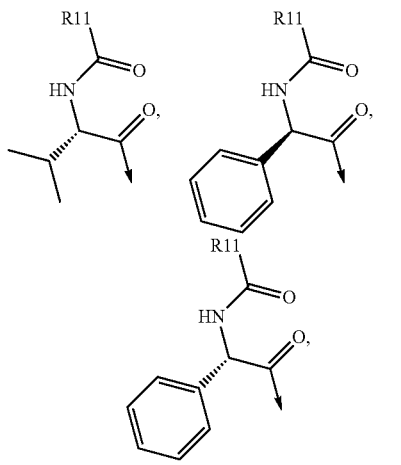

where R11 is an optionally substituted $C_1$-$C_6$ alkyl, an optionally substituted $C_3$-$C_6$ cycloalkyl, or an optionally substituted $C_1$-$C_6$ alkyloxy, and arrows (←) indicate the position of substituents attachment;

R2 is hydrogen, halogen, $C_1$-$C_4$alkyl;

R3 is an optionally substituted aryl, an optionally substituted aryloxy, an optionally substituted arylsulfanyl, an optionally substituted arylamino, or an optionally substituted nitrogen hetaryl;

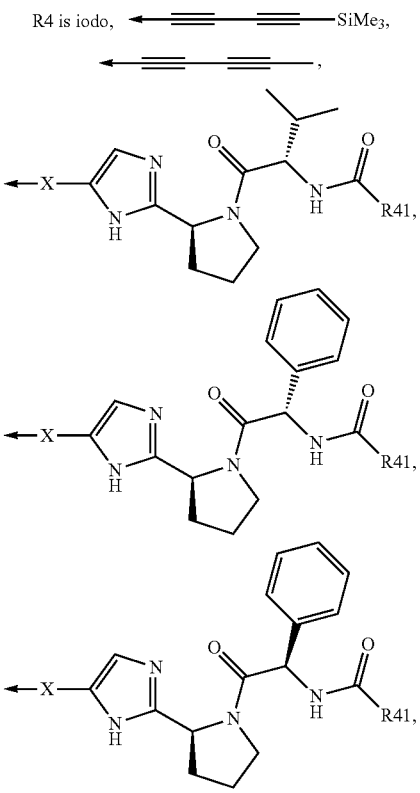

where R41 is an optionally substituted $C_1$-$C_6$ alkyl, an optionally substituted $C_3$-$C_6$ cycloalkyl, or an optionally substituted $C_1$-$C_6$ alkyloxy; X is buta-1,3-diynylene or 1,4-phenylene; arrows (←) indicate the position of substituents attachment.

Inventors have surprisingly found that the compounds of formula 1.2 or a pharmaceutically acceptable salt, a hydrate, or a crystalline form containing, in contrast to known HCV NS5A inhibitors Daclatasvir, Ledipasvir, and AV-4025, a linker comprising volumetric aryl or hetaryl substituent R2 and/or R3 are highly effective pan-genomic HCV NS5A inhibitors.

wherein:

R42 is phenyl or isopropyl;

C* is (R) or (S) chiral carbon;

R1, R2, R3, R11, R41, X and arrows (←) are as defined above.

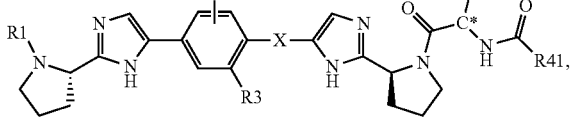

The most preferred inhibitor is one selected from the group of compounds 2(1)-2(33) or a pharmaceutically acceptable salt, a hydrate, or a crystalline form thereof.

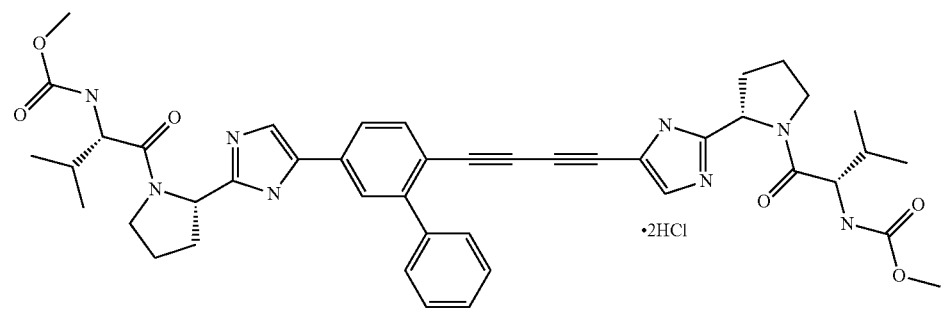

2(1)·2HCl

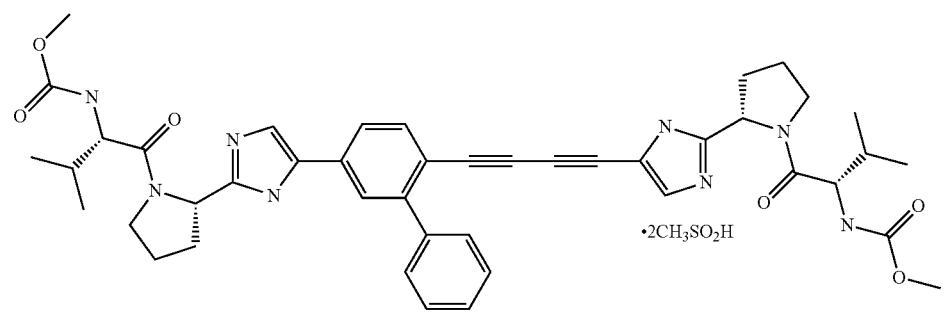

2(1)·2CH₃SO₃H

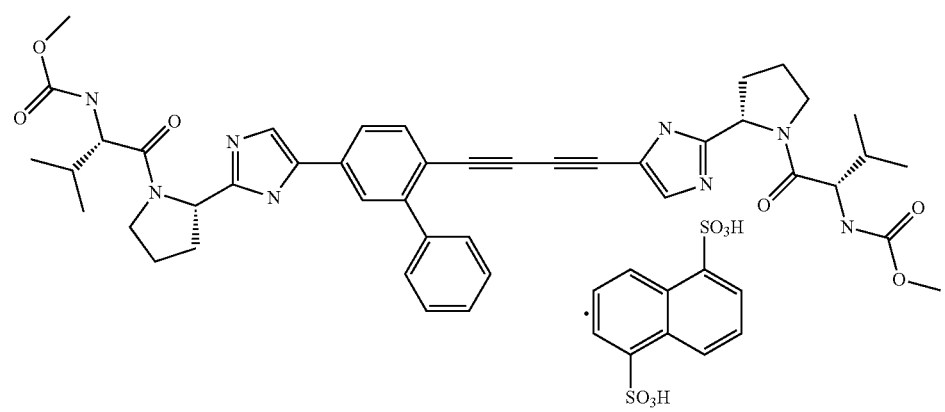

2(1)·naphthalene-1,5-disulfonic acid

-continued
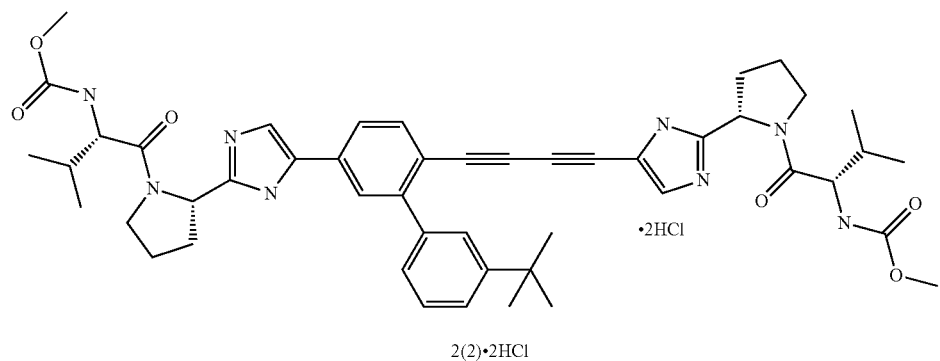
2(2)·2HCl
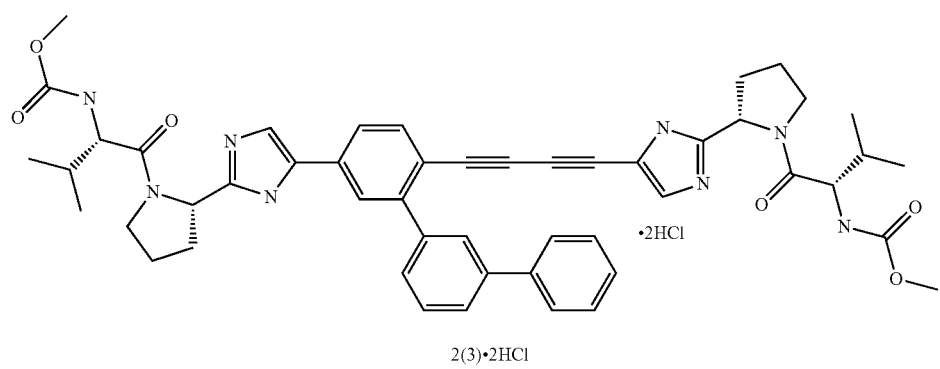
2(3)·2HCl
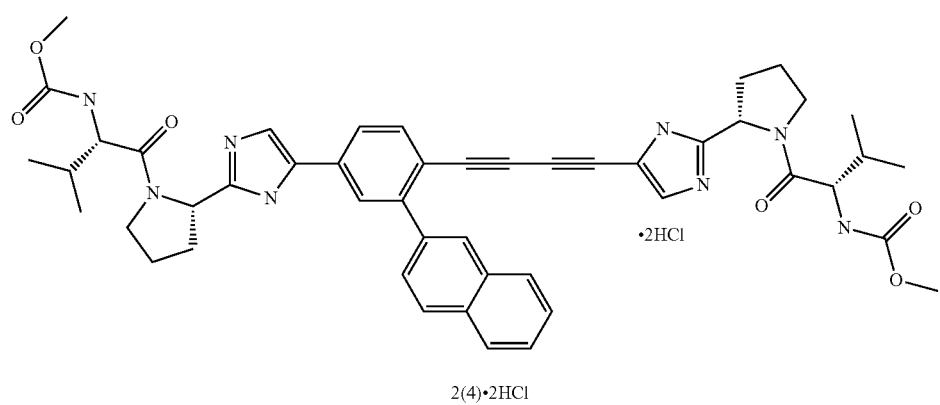
2(4)·2HCl
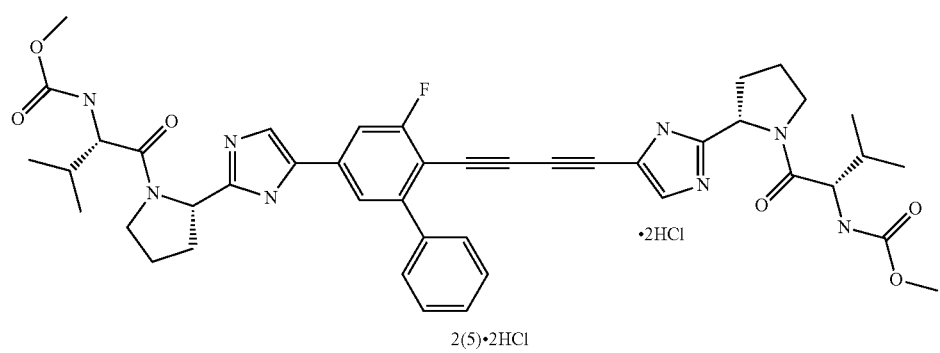
2(5)·2HCl

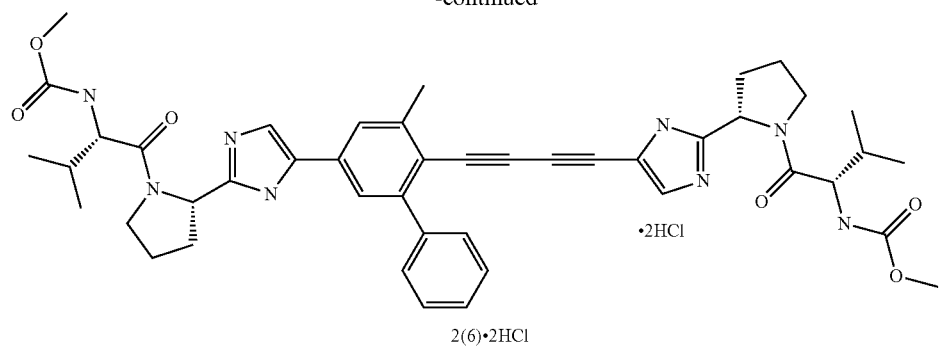
2(6)·2HCl
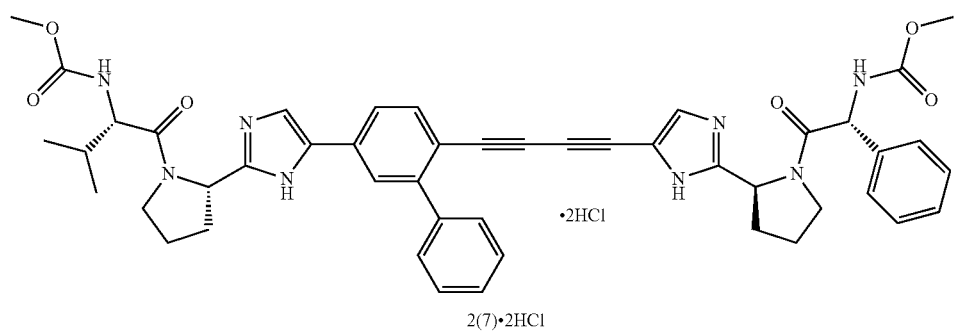
2(7)·2HCl
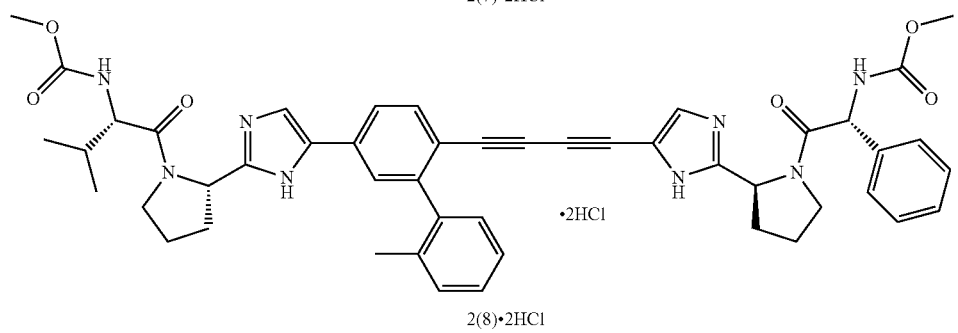
2(8)·2HCl
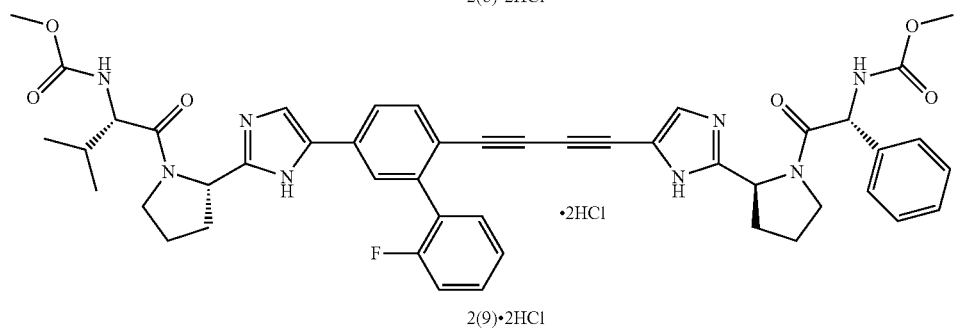
2(9)·2HCl
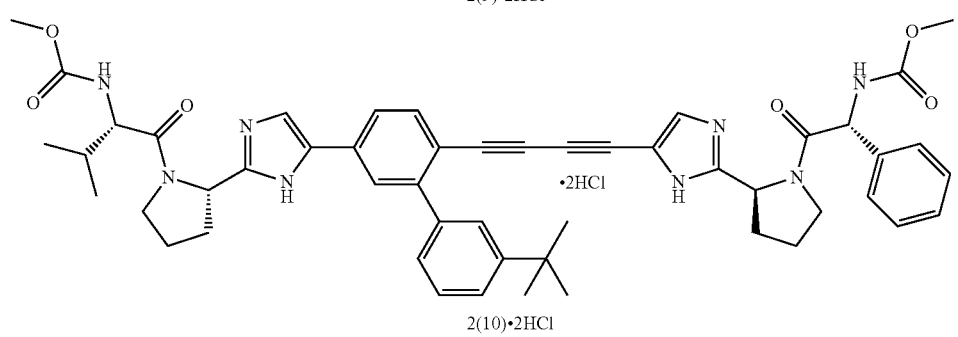
2(10)·2HCl

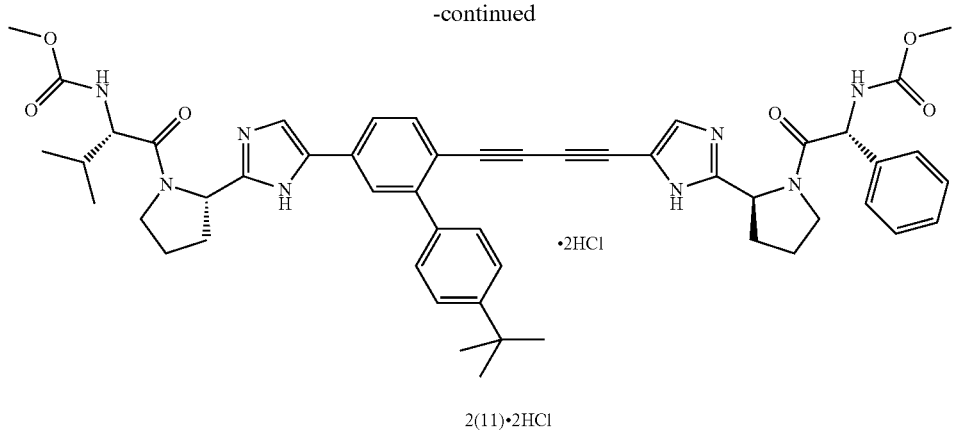
2(11)·2HCl
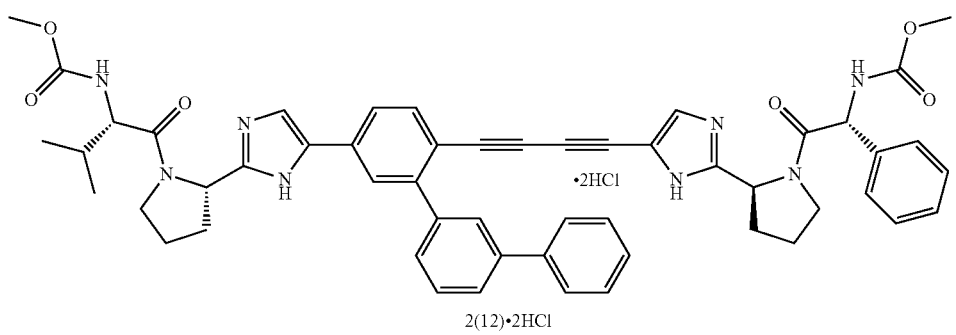
2(12)·2HCl
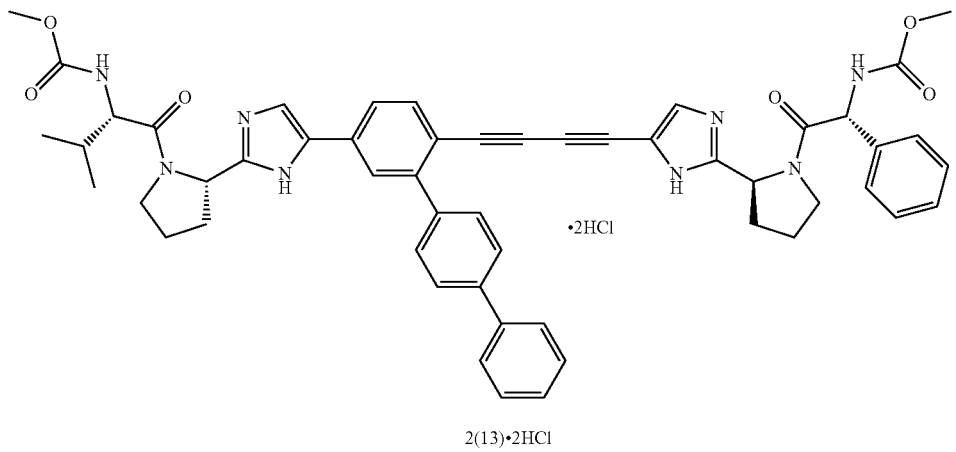
2(13)·2HCl
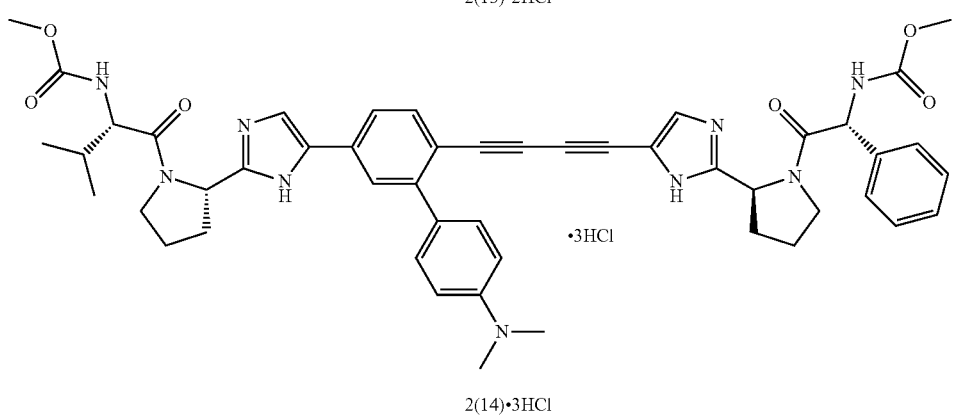
2(14)·3HCl

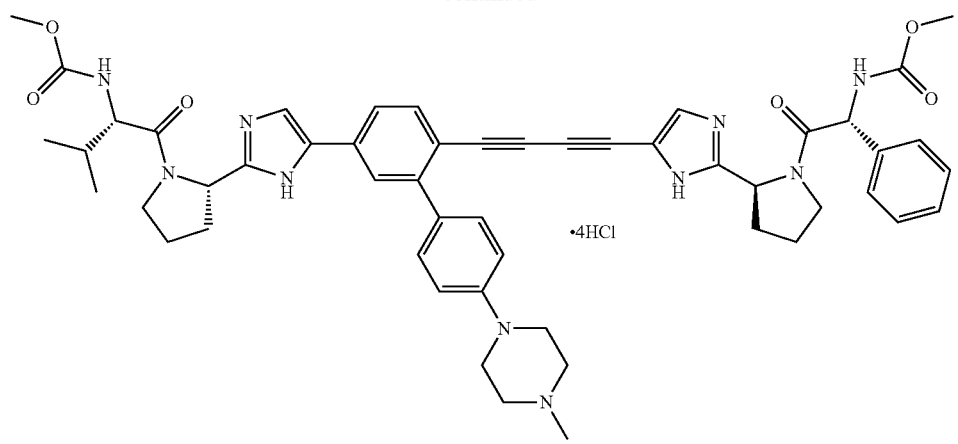
2(15)·4HCl
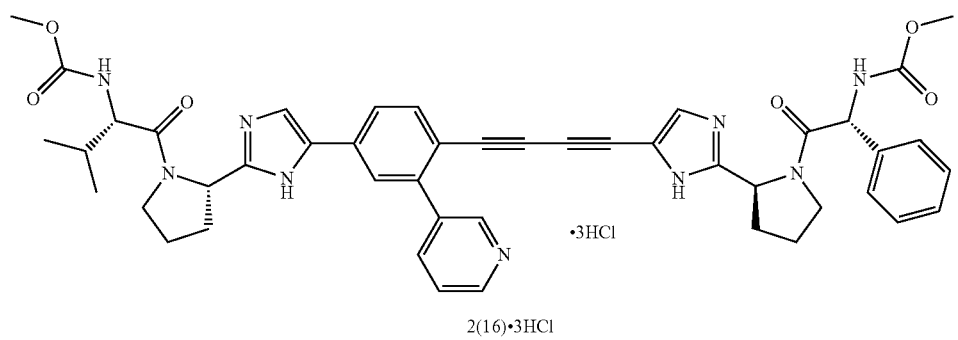
2(16)·3HCl
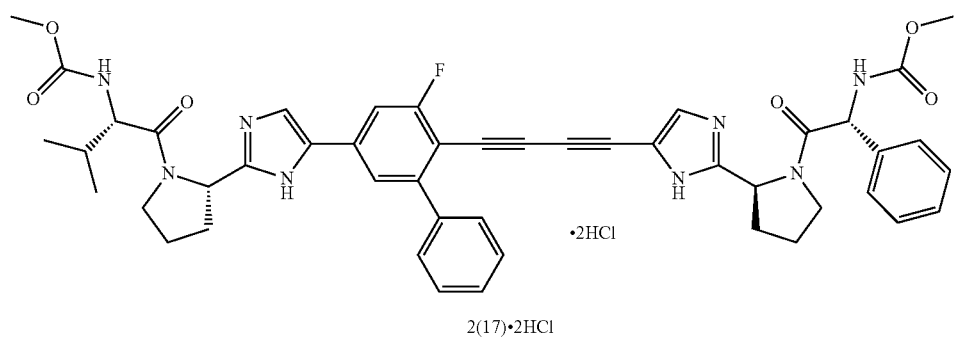
2(17)·2HCl
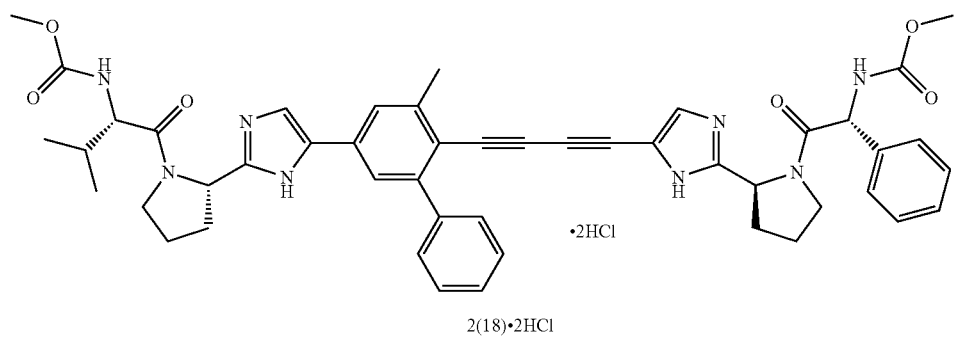
2(18)·2HCl

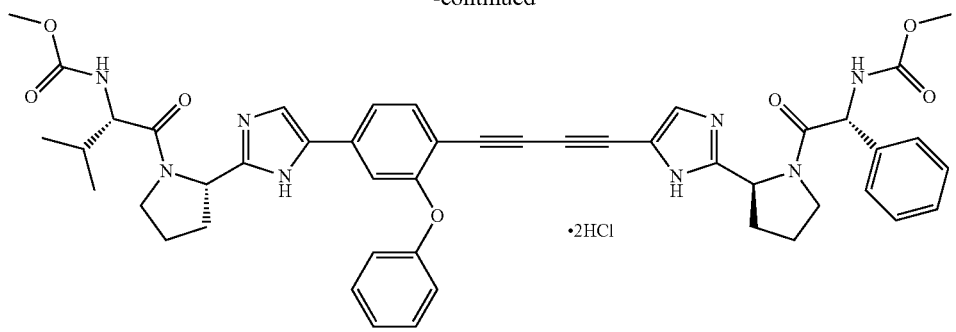
2(19)·2HCl
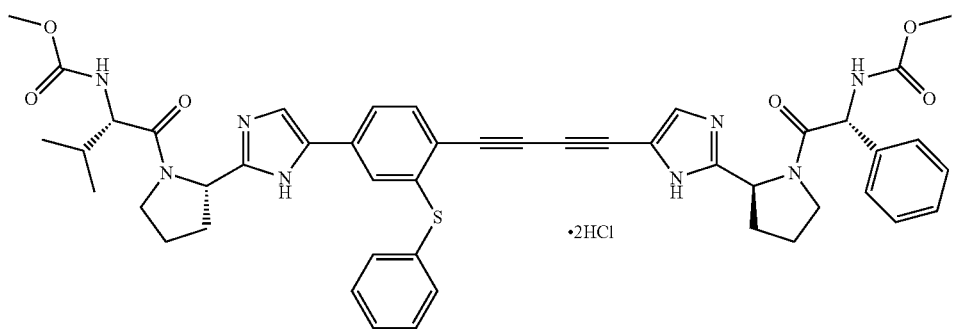
2(20)·2HCl
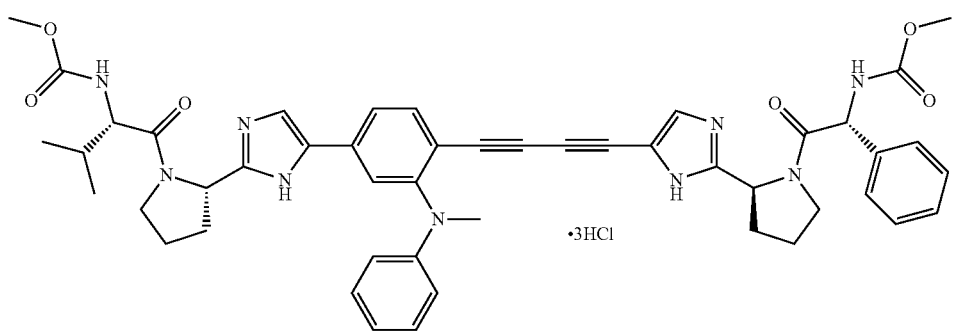
2(21)·3HCl
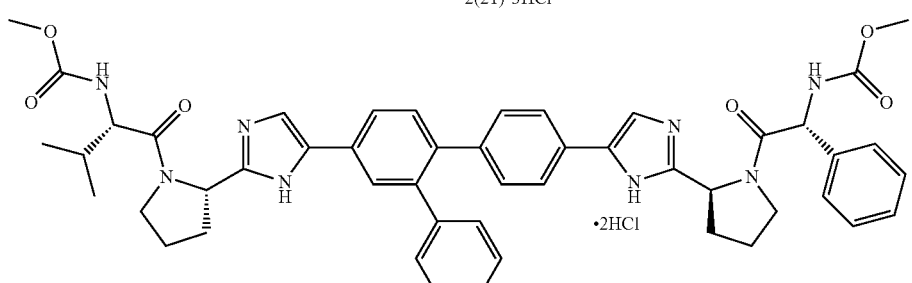
2(22)·2HCl

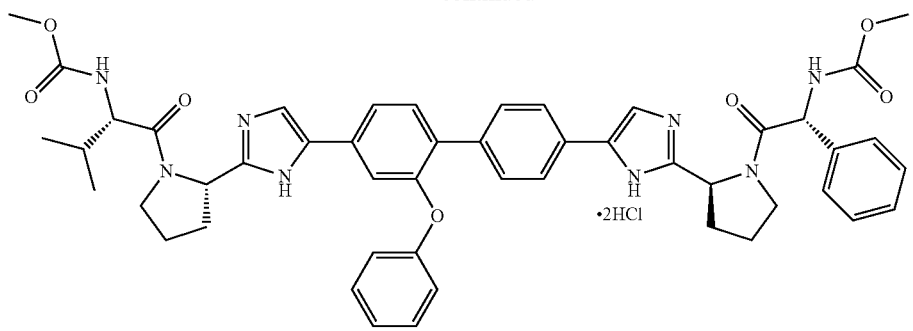
2(23)·2HCl
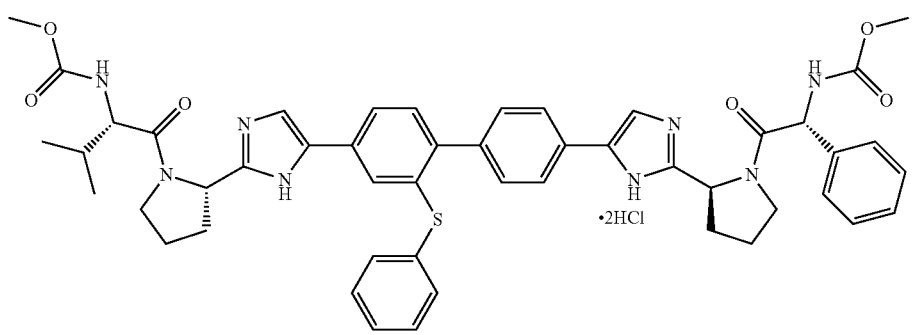
2(24)·2HCl
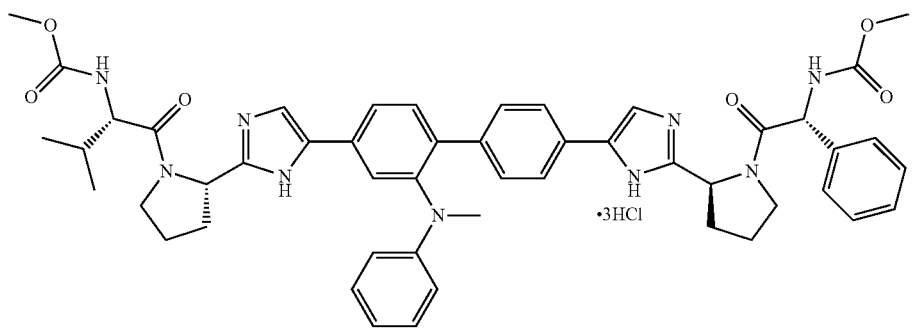
2(25)·3HCl
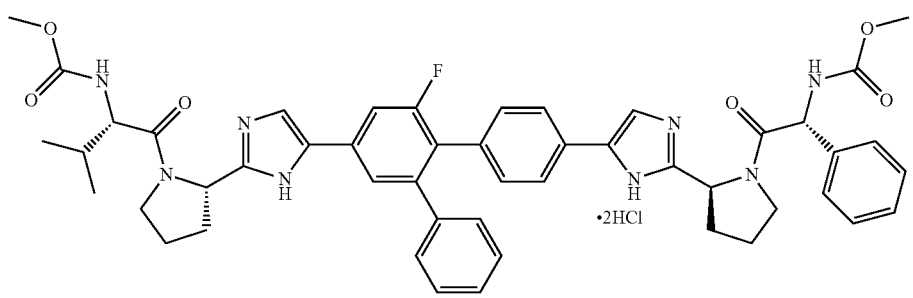
2(26)·2HCl

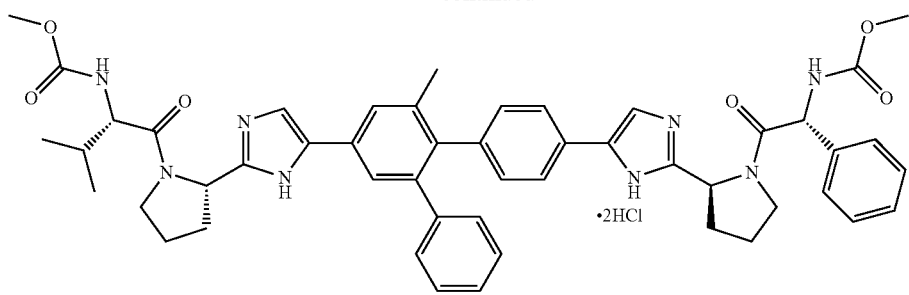
2(27)·2HCl
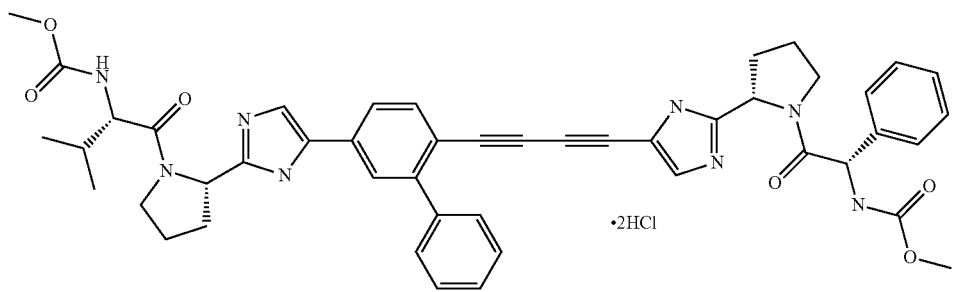
2(28)·2HCl
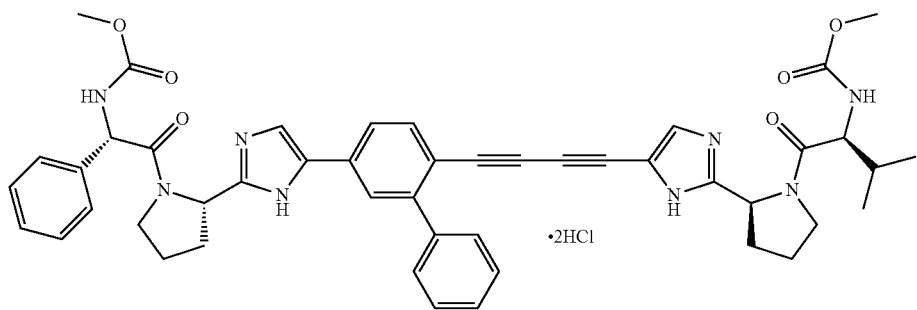
2(29)·2HCl
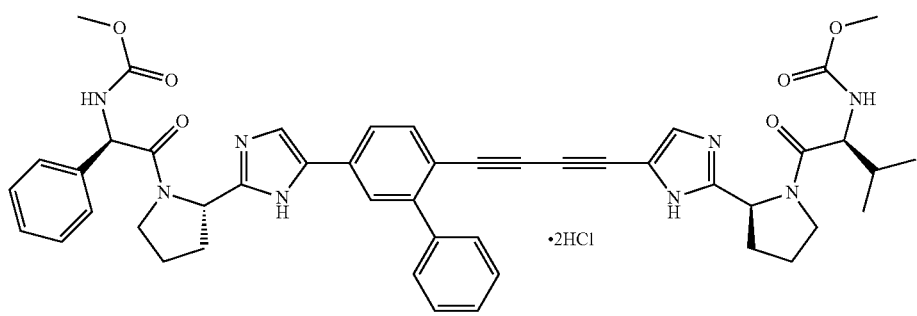
2(30)·2HCl

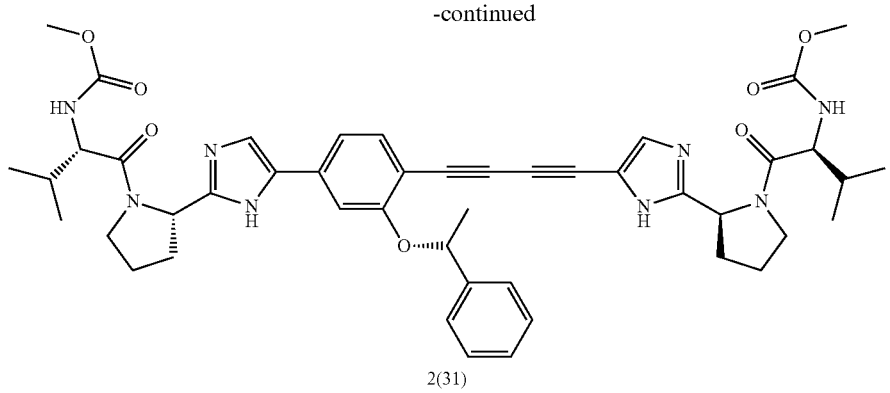

2(31)

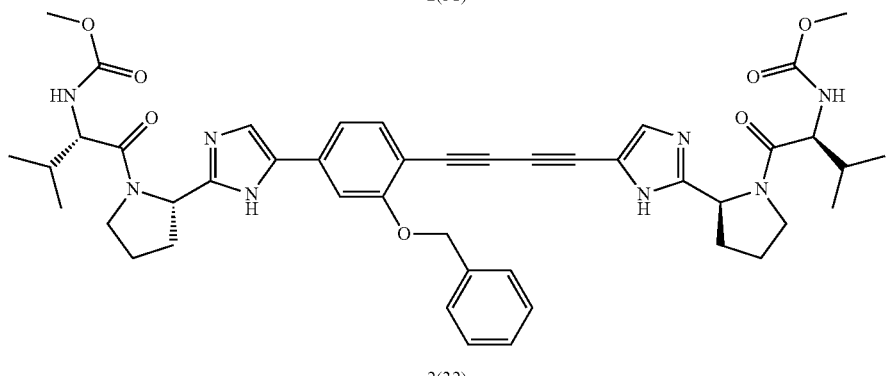

2(32)

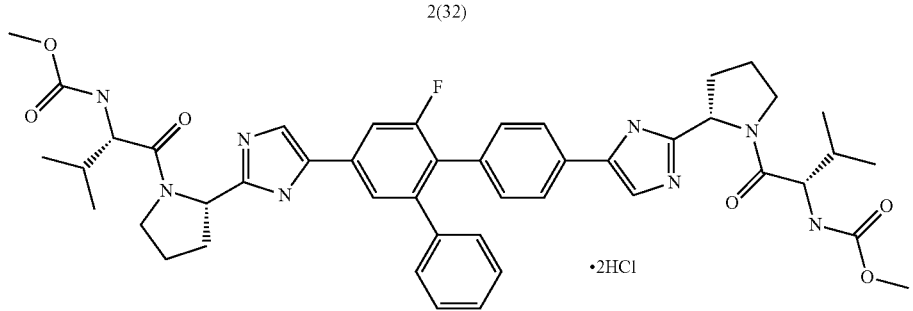

2(33)

[(S)-1-((S)-2-{5-[4-(5-{2-[(S)-1-((S)-2-Methoxycarbo-nylamino-3-methyl-butyryl)-pyrrolidin-2-yl]-3H-imida-zol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(1).2HCl),

[(S)-1-((S)-2-{5-[4-(5-{2-[(S)-1-((S)-2-Methoxycarbo-nylamino-3-methyl-butyryl)-pyrrolidin-2-yl]-3H-imida-zol-4-yl}-biphenyl-2-yl)-buta-1,3-diynyl]-1H-imidazol-2-yl}-pyrrolidine-1-carbonyl)-2-methyl-propyl]-carbamic acid methyl ester dimesylate (2(1).2CH$_3$SO$_3$H),

[(S)-1-((S)-2-{5-[4-(5-{2-[(S)-1-((S)-2-Methoxycarbo-nylamino-3-methyl-butyryl)-pyrrolidin-2-yl]-3H-imida-zol-4-yl}-biphenyl-2-yl)-buta-1,3-diynyl]-1H-imidazol-2-yl}-pyrrolidine-1-carbonyl)-2-methyl-propyl]-carbamic acid methyl ester naphtalene-1,5-disulfonate (2(1).2CH$_3$SO$_3$H),

[(S)-1-((S)-2-{5-[4-(3'-tert-Butyl-5-{2-[(S)-1-((S)-2-methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(2).2HCl),

[(S)-1-((S)-2-{5-[4-(5-{2-[(S)-1-((S)-2-Methoxycarbo-nylamino-3-methyl-butyryl)-pyrrolidin-2-yl]-3H-imida-zol-4-yl}-[1,1';  3',1"]terphenyl-2-yl)-buta-1,3-diynyl]-1H-imidazol-2-yl}-pyrrolidine-1-carbonyl)-2-methyl-propyl]-carbamic acid methyl ester dihydrochloride (2(3).2HCl),

[(S)-1-((S)-2-{5-[4-(4-{2-[(S)-1-((S)-2-Methoxycarbo-nylamino-3-methyl-butyryl)-pyrrolidin-2-yl]-3H-imida-zol-4-yl}-2-naphthalen-2-yl-phenyl)-buta-1,3-diynyl]-1H-imidazol-2-yl}-pyrrolidine-1-carbonyl)-2-methyl-propyl]-carbamic acid methyl ester dihydrochloride (2(4).2HCl),

[(S)-1-((S)-2-{5-[4-(2-Fluoro-4-{2-[(S)-1-((S)-2-methoxy-carbonylamino-3-methyl-butyryl)-pyrrolidin-2-yl]-3H-imidazol-4-yl}-phenyl)-buta-1,3-diynyl]-1H-imidazol-2-yl}-pyrrolidine-1-carbonyl)-2-methyl-propyl]-carbamic acid methyl ester dihydrochloride (2(5).2HCl),

[(S)-1-((S)-2-{5-[4-(4-{2-[(S)-1-((S)-2-Methoxycarbo-nylamino-3-methyl-butyryl)-pyrrolidin-2-yl]-3H-imida-zol-4-yl}-2-methyl-phenyl)-buta-1,3-diynyl]-1H-imida-zol-2-yl}-pyrrolidine-1-carbonyl)-2-methyl-propyl]-carbamic acid methyl ester dihydrochloride (2(6).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(7).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-2'-methyl-biphenyl-3-yl]-1H-imidazol-2-yl}-pyrrolidine-1-carbonyl)-2-methyl-propyl]-carbamic acid methyl ester dihydrochloride (2(8).2HCl),

[(S)-1-((S)-2-{5-[2'-Fluoro-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(9).2HCl),

[(S)-1-((S)-2-{5-[3'-tert-Butyl-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(10).2HCl),

[(S)-1-((S)-2-{5-[4'-tert-Butyl-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(11).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-[1,1';3',1"]terphenyl-3-yl]-1H-imidazol-2-yl}-pyrrolidine-1-carbonyl)-2-methyl-propyl]-carbamic acid methyl ester dihydrochloride (2(12).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-[1,1';4',1"]terphenyl-3-yl]-1H-imidazol-2-yl}-pyrrolidine-1-carbonyl)-2-methyl-propyl]-carbamic acid methyl ester dihydrochloride (2(13).2HCl),

[(S)-1-((S)-2-{5-[4'-Dimethylamino-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester troihydrochloride (2(14).3HCl),

[(S)-1-((S)-2-{5-[4'-(4-Methyl-piperazin-1-yl)-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester tetrahydrochloride (2(15).4HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-pyridin-3-yl-phenyl]-1H-imidazol-2-yl}-pyrrolidine-1-carbonyl)-2-methyl-propyl]-carbamic acid methyl ester trihydrochloride (2(16).3HCl),

[(S)-1-((S)-2-{5-[5-Fluoro-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(17).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-5-methyl-biphenyl-3-yl]-1H-imidazol-2-yl}-pyrrolidine-1-carbonyl)-2-methyl-propyl]-carbamic acid methyl ester dihydrochloride (2(18).2HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-phenoxy-phenyl]-1H-imidazol-2-yl}-pyrrolidine-1-carbonyl)-2-methyl-propyl]-carbamic acid methyl ester dihydrochloride (2(19).2HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-phenyl sulfanyl-phenyl]-1H-imidazol-2-yl}-pyrrolidine-1-carbonyl)-2-methyl-propyl]-carbamic acid methyl ester dihydrochloride (2(20).2HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-(methyl-phenyl-amino)-phenyl]-1H-imidazol-2-yl}-pyrrolidine-1-carbonyl)-2-methyl-propyl]-carbamic acid methyl ester trihydrochloride (2(21).3HCl), ((S)-1-{(S)-2-[5-(4-{2-[(S)-1-((R)-2-Methoxycarbonylamino-2-phenyl-acetyl)-pyrrolidin-2-yl]-3H-imidazol-4-yl}-[1,1';2',1"]terphenyl-4'-yl)-1H-imidazol-2-yl]-pyrrolidine-1-carbonyl}-2-methyl-propyl)-carbamic acid methyl ester dihydrochloride (2(22).2HCl), ((S)-1-{(S)-2-[5-(4'-{2-[(S)-1-((R)-2-Methoxycarbonylamino-2-phenyl-acetyl)-pyrrolidin-2-yl]-3H-imidazol-4-yl}-2-phenoxy-biphenyl-4-yl)-1H-imidazol-2-yl]-pyrrolidine-1-carbonyl}-2-methyl-propyl)-carbamic acid methyl ester dihydrochloride (2(23).2HCl), ((S)-1-{(S)-2-[5-(4'-{2-[(S)-1-((R)-2-Methoxycarbonylamino-2-phenyl-acetyl)-pyrrolidin-2-yl]-3H-imidazol-4-yl}-2-phenyl sulfanyl-biphenyl-4-yl)-1H-imidazol-2-yl]-pyrrolidine-1-carbonyl}-2-methyl-propyl)-carbamic acid methyl ester dihydrochloride (2(24).2HCl),

[(S)-1-((S)-2-{5-[4'-{2-[(S)-1-((R)-2-Methoxycarbonylamino-2-phenyl-acetyl)-pyrrolidin-2-yl]-3H-imidazol-4-yl}-2-(methyl-phenyl-amino)-biphenyl-4-yl]-1H-imidazol-2-yl}-pyrrolidine-1-carbonyl)-2-methyl-propyl]-carbamic acid methyl ester trihydrochloride (2(25).3HCl), ((S)-1-{(S)-2-[5-(6'-Fluoro-4-{2-[(S)-1-((R)-2-methoxycarbonylamino-2-phenyl-acetyl)-pyrrolidin-2-yl]-3H-imidazol-4-yl}-[1,1';2',1"]terphenyl-4'-yl)-1H-imidazol-2-yl]-pyrrolidine-1-carbonyl}-2-methyl-propyl)-carbamic acid methyl ester dihydrochloride (2(26).2HCl), ((S)-1-{(S)-2-[5-(4-{2-[(S)-1-((R)-2-Methoxycarbonylamino-2-phenyl-acetyl)-pyrrolidin-2-yl]-3H-imidazol-4-yl}-6'-methyl-[1,1';2',1"]terphenyl-4'-yl)-1H-imidazol-2-yl]-pyrrolidine-1-carbonyl}-2-methyl-propyl)-carbamic acid methyl ester dihydrochloride (2(27).2HCl),

[(S)-1-((S)-2-{5-[6-(4-{2-[(S)-1-((S)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(28).2HCl),

[(S)-1-((S)-2-{5-[4-(5-{2-[(S)-1-((S)-2-Methoxycarbonylamino-2-phenyl-acetyl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(29).2HCl),

[(S)-1-((S)-2-{5-[4-(5-{2-[(S)-1-((R)-2-Methoxycarbonylamino-2-phenyl-acetyl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(30).2HCl),

[(S)-1-((S)-2-{5-[4-(4-{2-[(S)-1-((S)-2-Methoxycarbonylamino-3-methyl-butyryl)-pyrrolidin-2-yl]-3H-imidazol-4-yl}-buta-1,3-diynyl)-3-((R)-1-phenyl-ethoxy)-phenyl]-1H-imidazol-2-yl}-pyrrolidine-1-carbonyl)-2-methyl-propyl]-carbamic acid methyl ester dihydrochloride (2(31).2HCl),

[(S)-1-((S)-2-{5-[3-Benzyloxy-4-(4-{2-[(S)-1-((S)-2-methoxycarbonylamino-3-methyl-butyryl)-pyrrolidin-2-yl]-3H-imidazol-4-yl}-buta-1,3-diynyl)-phenyl]-1H-imidazol-2-yl}-pyrrolidine-1-carbonyl)-2-methyl-propyl]-carbamic acid methyl ester dihydrochloride (2(32).2HCl), ((S)-1-{(S)-2-[5-(3'-Fluoro-5'-{2-[(S)-1-((S)-2-methoxycarbonylamino-3-methyl-butyryl)-pyrrolidin-2-yl]-3H-imidazol-4-yl}-[1,1';2',1"]terphenyl-4"-yl)-1H-imidazol-2-yl]-pyrrolidine-1-carbonyl}-2-methyl-propyl)-carbamic acid methyl ester dihydrochloride (2(33).2HCl), The new inhibitors of formula 2 demonstrate a very high picomolar activity both against GT1b HCV ($EC_{50}$ usually <2 pM, Table 2) and against GT2a and GT3a HCV, said activity drastically exceeding that of Daclatasvir, Ledipasvir, and AV-4025 (Table 3). Thus, the $EC_{50}$ activities against GT2a HCV of the new inhibitors given in Table 3 vary from 3.0 pM (inhibitor 2(18).2HCl) to 12.8 pM (inhibitor 2(14). 2HCl), while for Daclatasvir, Ledipasvir, and AV-4025, the $EC_{50}$ activities against GT2a HCV are 71 pM, 20.800 pM, and 51 pM, respectively. The new inhibitors are highly active against GT3a HCV (Table 3) as well, with $EC_{50}$ varying from 9.2 pM (inhibitor 2(26).2HCl) to 40.3 pM (inhibitor 2(19).2HCl), while for Daclatasvir, Ledipasvir, and AV-4025, the $EC_{50}$ activities against GT3a HCV are 103 pM, 10.100 pM, and 2.569 pM, respectively (Table 1). As compared with Daclatasvir, Ombitasvir, and Elbasvir, the new inhibitors have a higher bioavailability. For example, the bioavailability of inhibitor 2(7).2HCl in rats is 31%, while those for Daclatasvir, Ombitasvir, and Elbasvir are 11%, 6.2%, and 9%, respectively (Table 1).

TABLE 2

Activity and cytotoxicity of pan-genomic HCV NS5A inhibitors against gT1b

| | Mean value | | | | | | Cytotox | |
| --- | --- | --- | --- | --- | --- | --- | --- | --- |
| | gT1b 10% FBS, $EC_{50}$ (pM) | | | gT1b 40% NHS, $EC_{50}$ (pM) | | | gT1b 10% FBS | |
| Sample_ID | mean | min | Max | mean | min | max | $CC_{50}$ (nM) | max. inh. |
| 2(1)•2HCl | 1.79 | 1.25 | 2.57 | 12.39 | 9.12 | 16.85 | N/A | 42% |
| 2(2)•2HCl | 1.67 | 1.20 | 2.33 | 6.60 | 4.14 | 10.51 | N/A | 38% |
| 2(3)•2HCl | 1.24 | 0.88 | 1.77 | 17.15 | 15.68 | 18.76 | N/A | 29% |
| 2(4)•2HCl | 1.56 | 1.16 | 2.09 | 16.28 | 12.03 | 22.03 | N/A | 31% |
| 2(5)•2HCl | 1.53 | 1.05 | 2.23 | 7.40 | 4.94 | 11.08 | N/A | 38% |
| 2(6)•2HCl | 2.25 | 1.49 | 3.39 | 18.71 | 14.77 | 23.70 | N/A | 46% |
| 2(7)•2HCl | 1.92 | 1.29 | 2.86 | 12.55 | 10.49 | 15.01 | N/A | 32% |
| 2(10)•2HCl | 1.22 | 1.02 | 1.47 | 8.13 | 6.25 | 10.56 | N/A | 37% |
| 2(11)•2HCl | 1.24 | 0.89 | 1.74 | 10.73 | 7.93 | 14.52 | N/A | 29% |
| 2(12)•2HCl | 1.79 | 1.44 | 2.23 | 13.45 | 10.80 | 16.75 | N/A | 29% |
| 2(13)•2HCl | 1.61 | 1.00 | 2.56 | 14.42 | 10.51 | 19.77 | N/A | 24% |
| 2(14)•2HCl | 1.51 | 1.18 | 1.92 | 12.99 | 10.32 | 16.36 | N/A | 23% |
| 2(15)•2HCl | 3.65 | 2.27 | 5.88 | 23.86 | 12.15 | 46.85 | 16200 | 82% |
| 2(16)•2HCl | 4.70 | 2.71 | 8.13 | 36.21 | 31.04 | 42.24 | N/A | 32% |
| 2(17)•2HCl | 1.36 | 0.97 | 1.90 | 9.18 | 6.58 | 12.81 | N/A | 22% |
| 2(18)•2HCl | 1.89 | 1.35 | 2.65 | 10.92 | 7.34 | 16.24 | N/A | 12% |
| 2(19)•2HCl | 1.53 | 1.19 | 1.97 | 8.41 | 5.92 | 11.96 | N/A | 38% |
| 2(20)•2HCl | 1.70 | 1.05 | 2.77 | 9.02 | 7.22 | 11.27 | N/A | 43% |
| 2(21)•2HCl | 1.79 | 1.15 | 2.79 | 14.17 | 12.42 | 16.16 | N/A | 14% |
| 2(22)•2HCl | 2.58 | 1.87 | 3.56 | 38.81 | 30.23 | 49.82 | N/A | 30% |
| 2(23)•2HCl | 2.10 | 1.76 | 2.50 | 15.73 | 9.20 | 26.89 | N/A | 27% |
| 2(24)•2HCl | 1.33 | 1.04 | 1.71 | 8.02 | 6.18 | 10.41 | N/A | 42% |
| 2(25)•2HCl | 1.72 | 0.98 | 2.99 | 11.50 | 9.08 | 14.57 | N/A | 18% |
| 2(30)•2HCl | 2.10 | 1.28 | 3.43 | 25.33 | 21.38 | 30.02 | N/A | 33% |
| 2(26)•2HCl | 3.2 | 2.1 | 5.0 | 14.5 | 10.6 | 20.0 | N/A | 39% |
| 2(27)•2HCl | 5.1 | 4.0 | 6.6 | 14.5 | 8.3 | 25.4 | N/A | 31% |

TABLE 3

Activity and cytotoxicity of pan-genomic HCV NS5A inhibitors against gT1b

| ID | gT1a, EC$_{50}$ (pM) | | | gT2a, EC$_{50}$ (pM) | | | gT3a, EC$_{50}$ (pM) | | | gT4a, EC$_{50}$ (pM) | | | gT5a, EC$_{50}$ (pM) | | |
|---|---|---|---|---|---|---|---|---|---|---|---|---|---|---|---|
| | mean | min | max | mean | min | max | mean | min | max | mean | min | max | mean | min | max |
| 2(7)•2HCl | 22.5 | 10.5 | 48.0 | 5.9 | 3.6 | 9.6 | 23.0 | 11.7 | 45.3 | 8.5 | 6.8 | 10.7 | 19.8 | 14.8 | 26.6 |
| 2(14)•2HCl | 137.6 | 88.0 | 215.2 | 12.8 | 4.7 | 34.9 | 38.5 | 25.2 | 58.7 | 10.8 | 25.2 | 58.7 | 52.0 | 582.3 | 824.9 |
| 2(17)•2HCl | 50.8 | 35.2 | 73.4 | 5.0 | 3.0 | 8.5 | 20.1 | 16.9 | 24.0 | 11.8 | 16.9 | 24.0 | 26.0 | 115.1 | 124.7 |
| 2(18)•2HCl | 124.1 | 94.9 | 162.3 | 3.0 | 1.3 | 7.1 | 26.0 | 20.0 | 33.8 | 9.6 | 20.0 | 33.8 | 19.2 | 20.3 | 33.1 |
| 2(19)•2HCl | 213.7 | 150.7 | 303.3 | 12.6 | 7.2 | 22.0 | 40.3 | 28.6 | 56.8 | 6.0 | 28.6 | 56.8 | 18.8 | 20.7 | 22.5 |
| 2(21)•2HCl | 72.0 | 54.5 | 95.0 | 10.6 | 8.0 | 13.9 | 35.1 | 30.4 | 40.6 | 11.0 | 30.4 | 40.6 | 26.6 | 15.1 | 24.4 |
| 2(22)•2HCl | 117.0 | 75.8 | 180.6 | 3.9 | 2.4 | 6.4 | 16.6 | 11.6 | 23.8 | 9.4 | 11.6 | 23.8 | 31.3 | 277.0 | 457.2 |
| 2(23)•2HCl | 154.5 | 114.2 | 209.2 | 4.1 | 3.1 | 5.3 | 10.3 | 8.9 | 11.8 | 5.4 | 8.9 | 11.8 | 13.6 | 29.2 | 33.5 |
| 2(24)•2HCl | 557.1 | 526.9 | 589.0 | 4.0 | 2.3 | 6.8 | 28.5 | 20.2 | 40.1 | 8.3 | 20.2 | 40.1 | 21.6 | 10.7 | 17.3 |
| 2(25)•2HCl | 345.1 | 263.7 | 451.5 | 5.5 | 4.6 | 6.7 | 24.2 | 18.6 | 31.5 | 13.9 | 18.6 | 31.5 | 43.2 | 24.5 | 28.8 |
| 2(26)•2HCl | 30.3 | 28.1 | 32.8 | 3.1 | 2.4 | 3.8 | 9.8 | 6.3 | 15.0 | 7.9 | 5.2 | 12.2 | 14.3 | 11.9 | 17.2 |
| 2(27)•2HCl | 202.8 | 75.5 | 545.2 | 7.9 | 4.2 | 14.9 | 25.2 | 17.4 | 36.6 | 12.3 | 9.4 | 16.1 | 25.8 | 22.3 | 29.9 |

A further embodiment of the present invention includes pharmaceutical compositions comprising any single compound of formula 2 or a combination of two or more compounds of formula 2 delineated herein, or a pharmaceutically acceptable salt of any of thereof, with a pharmaceutically acceptable carrier or excipient.

It will be further shown that compounds of formula 2 of the present invention can be administered as a sole active pharmaceutical agent, or used in combination with one or more agents to treat or prevent hepatitis C infections or symptoms associated with HCV infection. Other agents to be administered in combination with one or more compounds of formula 2 of the present invention include therapeuticals for diseases caused by HCV infection that suppresses HCV viral replication by direct or indirect mechanisms. These agents include, but not limited to, host immune modulators (for example, interferon-alpha, pegylated interferon-alpha, consensus interferon, interferon-beta, interferon-gamma, CpG oligonucleotides, and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; antisense RNA; vaccines comprising HCV antigens or antigen adjuvant combinations directed against HCV; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein, and NS5A protein.

Accordingly, one embodiment of the present invention provides a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound of formula 2 or a combination of compounds of formula 2 of the present invention, or a pharmaceutically acceptable salt thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. A nonlimiting example of the RNA-containing virus is hepatitis C virus (HCV).

A further embodiment of the present invention provides a method for treating or preventing infection caused by an RNA-containing virus comprising co-administering to a patient in need of such treatment an agent or a combination of agents that treat or alleviate symptoms of HCV infection including cirrhosis and inflammation of the liver, with a therapeutically effective amount of a compound of formula 2 or a combination of compounds of formula 2 of the present invention, or a pharmaceutically acceptable salt thereof. A non-limiting example of the RNA-containing virus is hepatitis C virus (HCV).

Yet another embodiment of the present invention provides a method for treating or preventing infection caused by an RNA-containing virus comprising co-administering to a patient in need of such treatment one or more agents that treat patients for disease caused by hepatitis B (HBV) infection, with a therapeutically effective amount of a compound of formula 2 or a combination of compounds of formula 2 of the present invention, or a pharmaceutically acceptable salt thereof. An agent that treats patients for disease caused by hepatitis B (HBV) infection may be, for example, but not limited to, L-deoxythymidine, adefovir, lamivudine or tenofovir, or any combination thereof. A non-limiting example of an RNA-containing virus is hepatitis C virus (HCV).

A further embodiment of the present invention provides a method for treating or preventing infection caused by an RNA-containing virus comprising co-administering to a patient in need of such treatment one or more agents that treat patients for disease caused by human immunodeficiency virus (HIV) infection, with a therapeutically effective amount of a compound of formula 2 or a combination of compounds of formula 2 of the present invention, or a pharmaceutically acceptable salt thereof. The agent that treats patients for disease caused by human immunodeficiency virus (HIV) infection may include, but is not limited to, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of an RNA-containing virus is hepatitis C virus (HCV).

It can occur that a patient may be co-infected with hepatitis C virus and one or more other viruses, including, but not limited to, human immunodeficiency virus (HIV), hepatitis A virus (HAV), or hepatitis B virus (HBV). Thus, also contemplated herein is combination therapy to treat such co-infections by co-administering a compound of formula 2 according to the present invention with at least one HIV, HAY, or HBV inhibitor.

In addition, the present invention provides the use of a compound or a combination of compounds of formula 2 of the invention, or a therapeutically acceptable salt thereof, and one or more agents selected from a group consisting of a host immune modulator and one or more additional antiviral agents, or a combination thereof, to prepare a medicament for the treatment of an infection caused by an RNA-containing virus in a patient, particularly, hepatitis C virus. Examples of the host immune modulator are, but not limited to, interferon-alpha, pegylated-interferon-alpha, interferon-beta, interferon-gamma, a cytokine, and a vaccine. Preferably, said additional antiviral agent inhibits replication of HCV either by inhibiting host cellular functions associated with viral replication or by targeting proteins of the viral genome.

When used in the above or other treatments, the combination of one or more compounds of formula 2 of the present invention, together with one or more agents as defined herein above, can be employed in a pure form or, where such forms exist, as a pharmaceutically acceptable salt thereof. Alternatively, such combination of therapeutic agents can be administered as a pharmaceutical composition containing a therapeutically effective amount of the compound or a combination of compounds of interest, or a pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention provides a method for treating or preventing infection caused by an RNA-containing virus, particularly, a hepatitis C virus (HCV), comprising administering to a patient in need of such treatment a pharmaceutical composition comprising a compound of formula 2 or a combination of compounds of formula 2 of the invention or a pharmaceutically acceptable salt thereof, and one or more agents as defined hereinabove, with a pharmaceutically acceptable carrier.

When administered as a combination, the therapeutic agents can be formulated as separate compositions given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to, agents that interfere with either host or viral mechanisms necessary for the formation and/or replication of the virus in a mammal. Such agents can be selected from another anti-HCV agent, an HIV inhibitor, an HAY inhibitor, or an HBV inhibitor.

Other agents that can be administered in combination with a compound of formula 2 of the present invention include a cytochrome P450 monooxygenase inhibitor (herein also referred to as a CYP inhibitor), which is expected to inhibit the metabolism of the compounds claimed herein. Therefore, the cytochrome P450 monooxygenase inhibitor would be in an amount effective to inhibit the metabolism of the compounds claimed herein. Accordingly, the CYP inhibitor is administered in an amount sufficient to increase the bioavailiablity of the compound of formula 2 of the invention, when the bioavailability is increased in comparison with the bioavailability in the absence of the CYP inhibitor.

In one embodiment, the invention provides methods for improving the pharmacokinetics of the compounds of formula 2 of the invention. The advantages of improving the pharmacokinetics of drugs are recognized in the art (see, for example, US Patent App. No. 2004/0091527; US 2004/0152625; and US2004/0091527). Accordingly, one embodiment of this invention provides a method comprising administering an inhibitor of CYP3A4 and compound 2.

Another embodiment of this invention provides a method comprising administering a compound of formula 2 of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharma cokinetics of the compound of formula 2 of the invention may be used in the method of this invention. These CYP inhibitors include, but are not limited to, ritonavir (see, for example, WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combination of the invention by means of a single patient pack, or patient packs of each formulation, containing within a package an insert instructing the patient in the correct use of the invention is a desirable additional feature of this invention.

A further aspect of the invention is a pack comprising at least one compound of formula 2 of the invention and a CYP inhibitor as well as an information insert containing directions for the use of the combination of the invention. In an alternative embodiment of this invention, the pack further comprises one or more additional agents as described herein. The additional agent or agents may be provided in the same pack or in separate packs.

Another aspect of this involves a packaged kit for a patient to use for treating or preventing HCV infection, comprising: a single or a plurality of pharmaceutical formulations of each pharmaceutical component; a container housing the pharmaceutical formulation(s) during storage and prior to administration; and instructions for drug administration in a manner effective to treat or prevent HCV infection.

Accordingly, this invention provides kits for simultaneous or sequential administration of a compound of formula 2 of the invention, with a CYP inhibitor (and optionally an additional agent) or derivatives thereof being prepared in a conventional manner. Typically, such kit will comprise, e.g., a composition of a compound of formula 2 of the invention and optionally an additional agent(s) in a pharmaceutically acceptable carrier (and in one or in a plurality of pharmaceutical formulations) and written instructions for simultaneous or sequential administration.

In another embodiment, a packaged kit is provided that contains one or more dosage forms for self-administration; a container means, preferably sealed, for housing the dosage forms during storage and prior to use; and instructions for drug administration. The instructions will typically be written instructions on a package insert, a label, and/or on other components of the kit, and the dosage form or forms are as described herein. Each dosage form may be individually housed, as in a sheet of metal plastic foil laminate, with each dosage form isolated from the others in individual cells or bubbles, or the dosage forms may be housed in a single container, as in a plastic bottle. The present kits will also typically include means for packaging individual kit components, i.e., dosage forms, container means, and written instructions for use. Such packaging means may take the form of a cardboard or paper box, a plastic or foil pouch, etc.

Another embodiment of this invention provides intermediates of formula 3, 4 or a pharmaceutically acceptable salt thereof. These intermediates of formula 3, 4 or a pharmaceutically acceptable salt thereof are used for the synthesis of compounds of formula 2 of the invention.

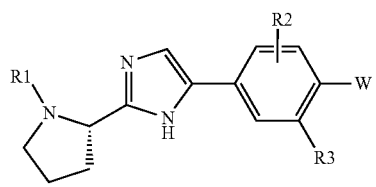

3

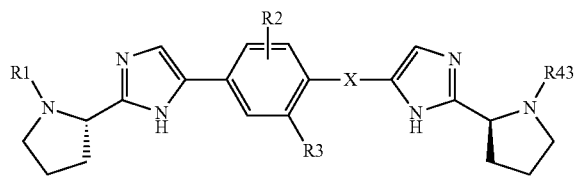

4 wherein:
W is iodo, 4-trimethylsilanyl-buta-1,3-diynyl and 3-buta-1,3-diynyl;
R43 is hydrogen, tert-butoxycarbonyl,

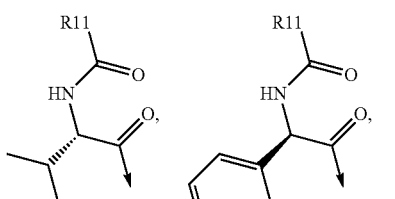

and

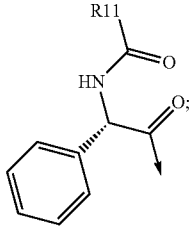

R1, R2, R3, R11, X, and arrows (←) are as defined above;

The most preferred intermediates are those selected from the groups of compounds 3(1)-3(40) and 4(1)-4(28) or a pharmaceutically acceptable salt thereof

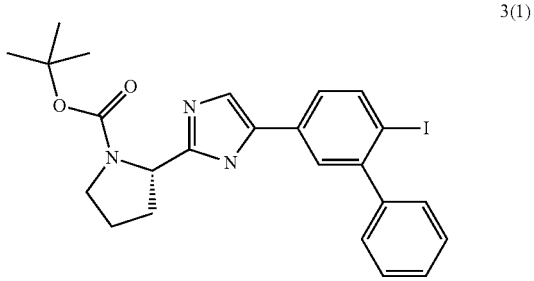

3(1)

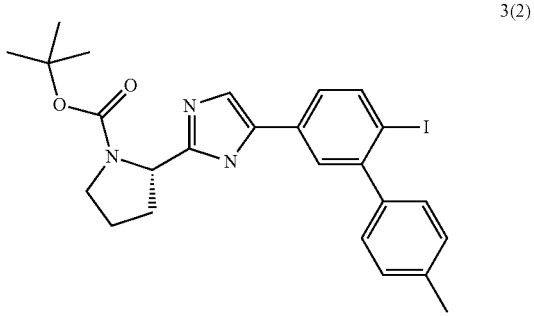

3(2)

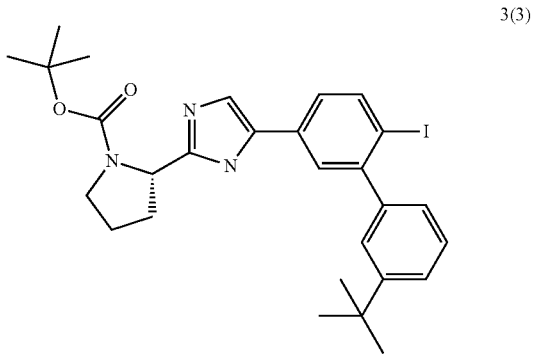

3(3)

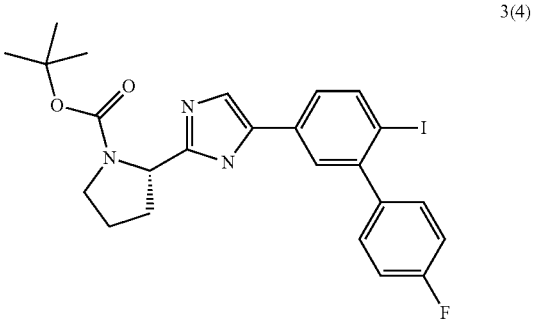

3(4)

-continued
3(5)
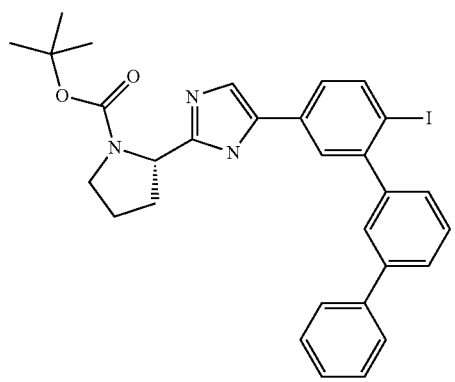
3(10)
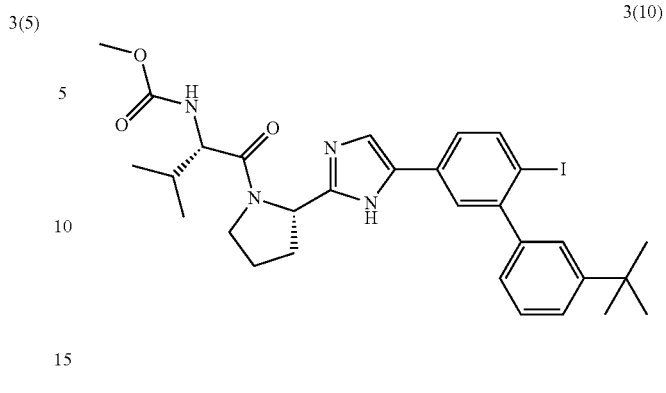
3(6)
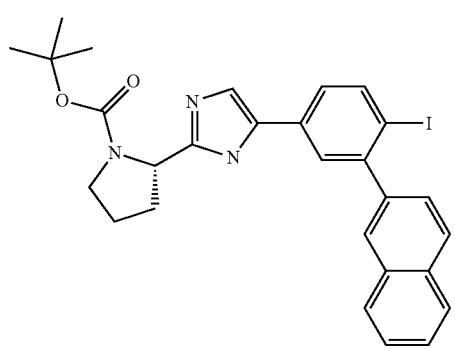
3(11)
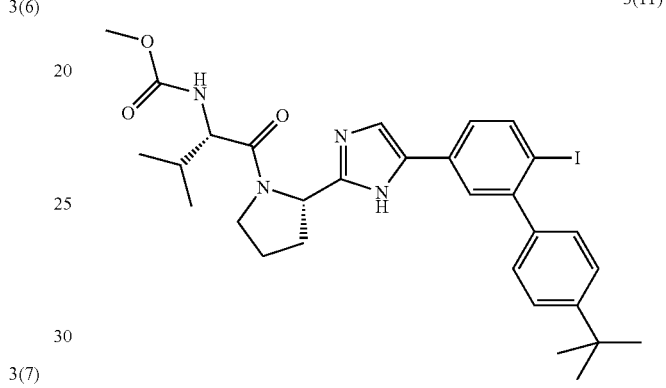
3(7)
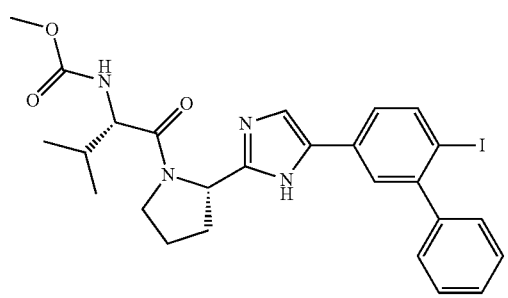
3(12)
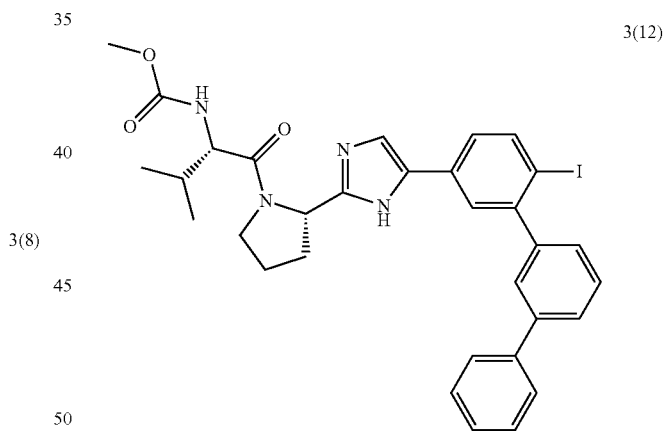
3(8)
3(9)
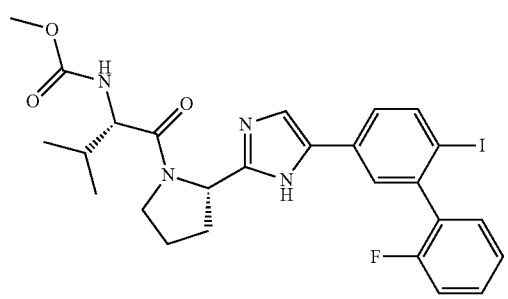
3(13)
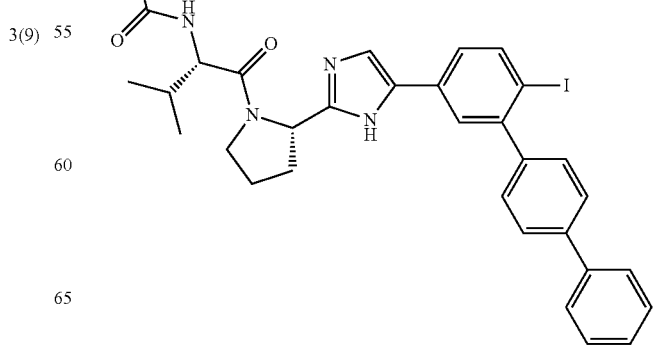

37
-continued
3(14)
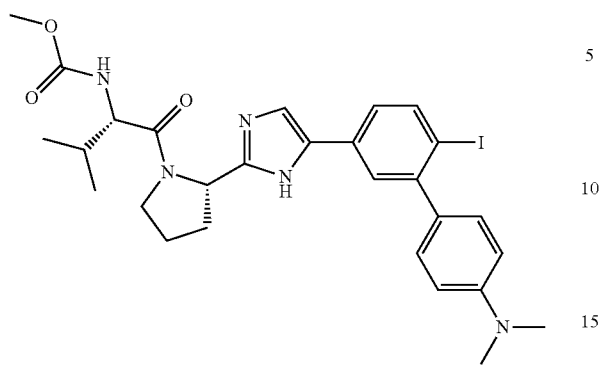
3(15)
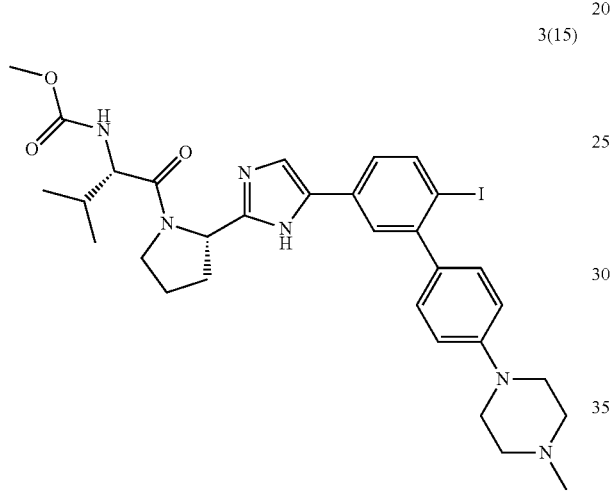
3(16)
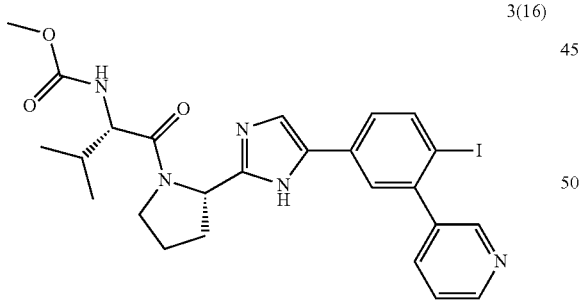
3(17)
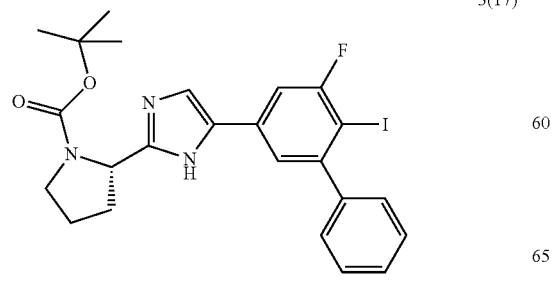
38
-continued
3(18)
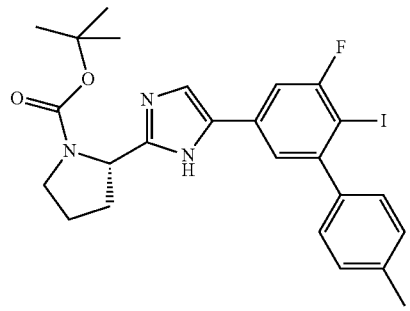
3(19)
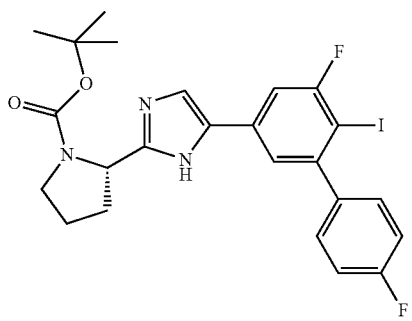
3(20)
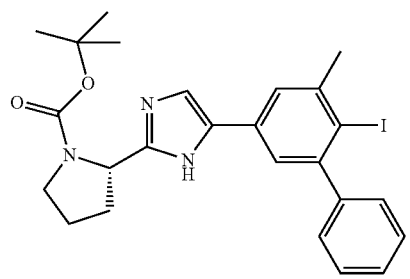
3(21)
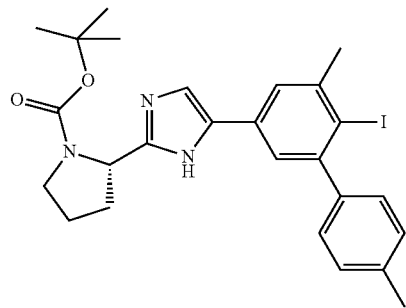
3(22)
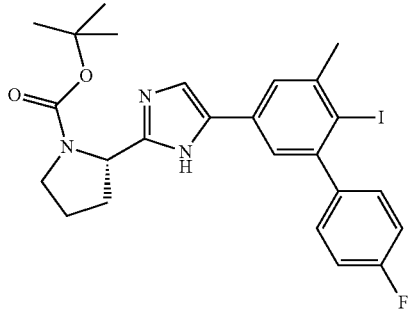

3(23)
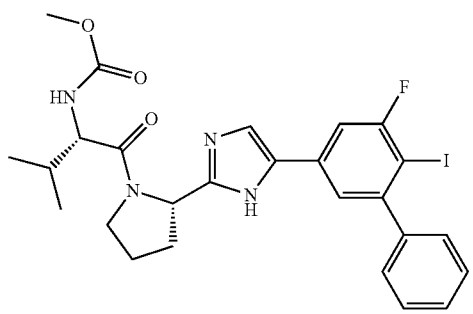
3(24)
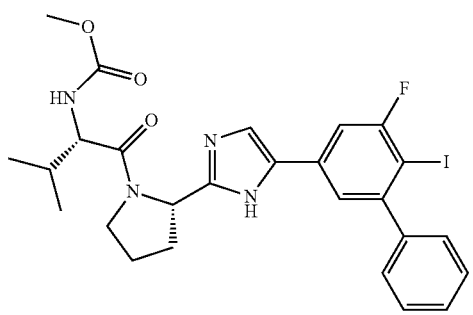
3(25)
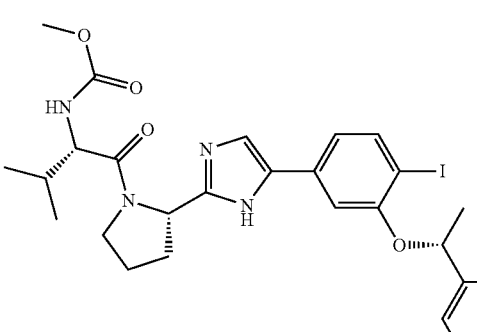
3(26)
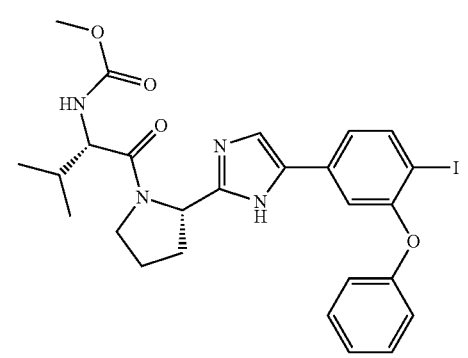
3(27)
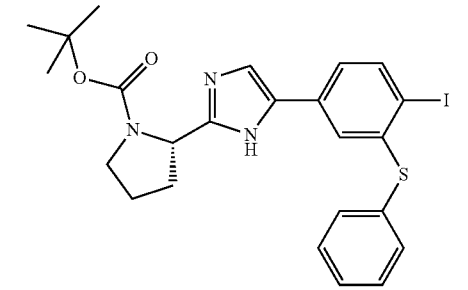
3(28)
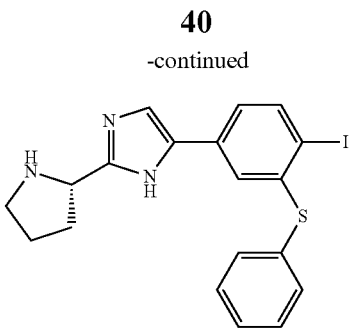
3(29)
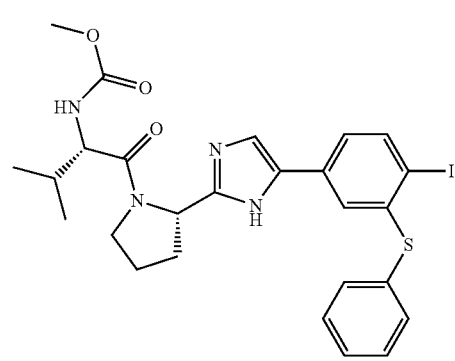
3(30)
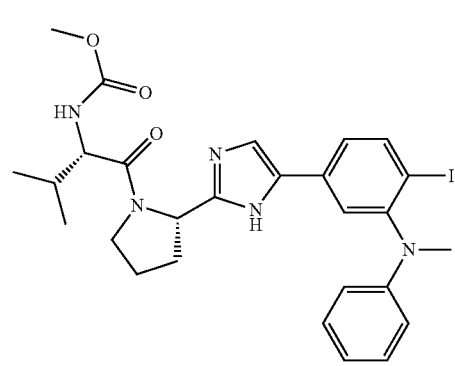
3(31)
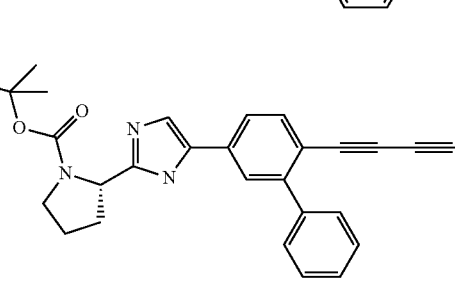
3(32)
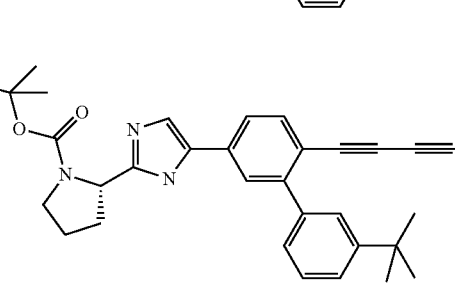

3(33)
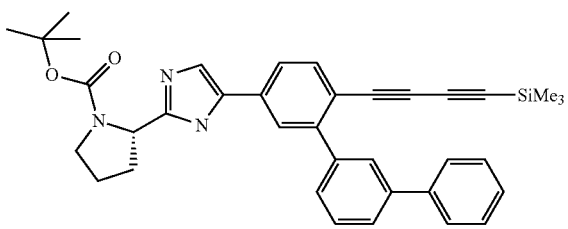

3(34)
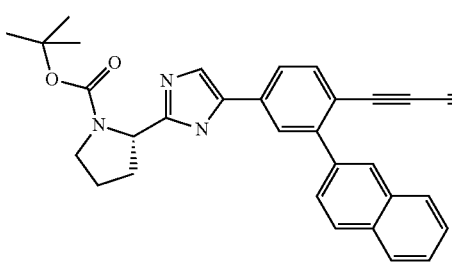

3(35)
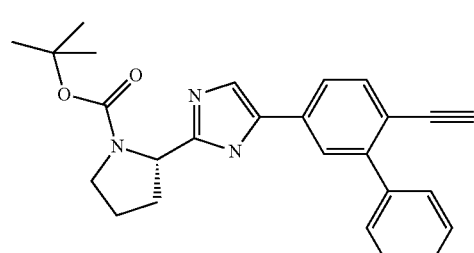

3(36)
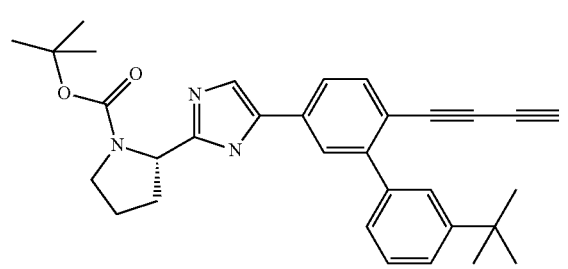

3(37)
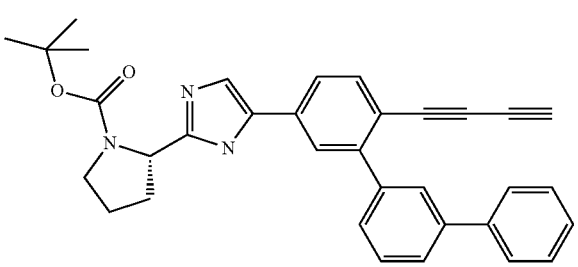

3(38)
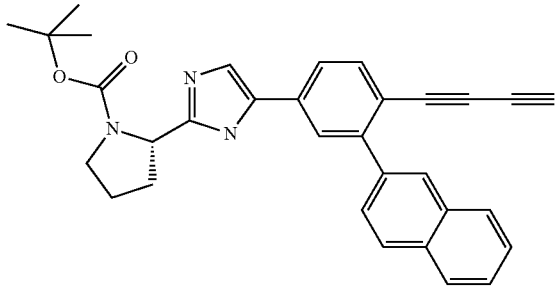

3(39)
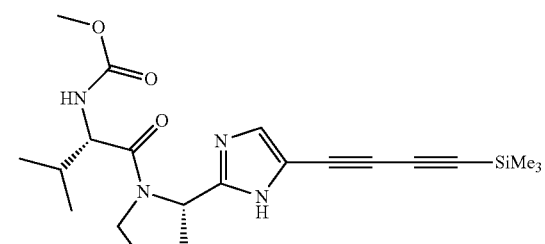

3(40)
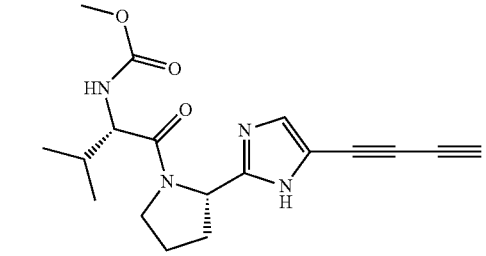

(S)-2-[5-(6-Iodo-biphenyl-3-yl)-1H-imidazol-2-yl]-pyrrolidine-1-carboxylic acid tert-butyl ester (3(1)),
(S)-2-[5-(6-Iodo-4'-methyl-biphenyl-3-yl)-1H-imidazol-2-yl]-pyrrolidine-1-carboxylic acid tert-butyl ester (3(2)),
(S)-2-[5-(3'-tert-Butyl-6-iodo-biphenyl-3-yl)-1H-imidazol-2-yl]-pyrrolidine-1-carboxylic acid tert-butyl ester (3(3)),
(S)-2-[5-(4'-Fluoro-6-iodo-biphenyl-3-yl)-1H-imidazol-2-yl]-pyrrolidine-1-carboxylic acid tert-butyl ester (3(4)),
(S)-2-[5-(6-Iodo-[1,1';3',1"]terphenyl-3-yl)-1H-imidazol-2-yl]-pyrrolidine-1-carboxylic acid tert-butyl ester (3(5)),
(S)-2-[5-(4-Iodo-3-naphthalen-2-yl-phenyl)-1H-imidazol-2-yl]-pyrrolidine-1-carboxylic acid tert-butyl ester (3(6)),
((S)-1-{(S)-2-[5-(6-Iodo-biphenyl-3-yl)-1H-imidazol-2-yl]-pyrrolidine-1-carbonyl}-2-methyl-propyl)-carbamic acid methyl ester (3(7)),
((S)-1-{(S)-2-[5-(2'-Fluoro-6-iodo-biphenyl-3-yl)-1H-imidazol-2-yl]-pyrrolidine-1-carbonyl}-2-methyl-propyl)-carbamic acid methyl ester (3(8)),
((S)-1-{(S)-2-[5-(6-Iodo-2'-methyl-biphenyl-3-yl)-1H-imidazol-2-yl]-pyrrolidine-1-carbonyl}-2-methyl-propyl)-carbamic acid methyl ester (3(9)),
((S)-1-{(S)-2-[5-(3'-tert-Butyl-6-iodo-biphenyl-3-yl)-1H-imidazol-2-yl]-pyrrolidine-1-carbonyl}-2-methyl-propyl)-carbamic acid methyl ester (3(10)),
((S)-1-{(S)-2-[5-(4'-tert-Butyl-6-iodo-biphenyl-3-yl)-1H-imidazol-2-yl]-pyrrolidine-1-carbonyl}-2-methyl-propyl)-carbamic acid methyl ester (3(11)),
((S)-1-{(S)-2-[5-(6-Iodo-[1,1';3',1"]terphenyl-3-yl)-1H-imidazol-2-yl]-pyrrolidine-1-carbonyl}-2-methyl-propyl)-carbamic acid methyl ester (3(12)), ((S)-1-{(S)-2-[5-(6-Iodo-[1,1';4',1"]terphenyl-3-yl)-1H-imidazol-2-yl]-pyrrolidine-1-carbonyl}-2-methyl-propyl)-carbamic acid methyl ester (3(13)),
((S)-1-{(S)-2-[5-(4'-Dimethylamino-6-iodo-biphenyl-3-yl)-1H-imidazol-2-yl]-pyrrolidine-1-carbonyl}-2-methyl-propyl)-carbamic acid methyl ester (3(14)),
[(S)-1-((S)-2-{5-[6-Iodo-4'-(4-methyl-piperazin-1-yl)-biphenyl-3-yl]-1H-imidazol-2-yl}-pyrrolidine-1-carbonyl)-2-methyl-propyl]-carbamic acid methyl ester (3(15)),
((S)-1-{(S)-2-[5-(4-Iodo-3-pyridin-3-yl-phenyl)-1H-imidazol-2-yl]-pyrrolidine-1-carbonyl}-2-methyl-propyl)-carbamic acid methyl ester (3(16)),
(S)-2-[5-(5-Fluoro-6-iodo-biphenyl-3-yl)-1H-imidazol-2-yl]-pyrrolidine-1-carboxylic acid tert-butyl ester (3(17)),
(S)-2-[5-(5-Fluoro-6-iodo-4'-methyl-biphenyl-3-yl)-1H-imidazol-2-yl]-pyrrolidine-1-carboxylic acid tert-butyl ester (3(18)),
(S)-2-[5-(5,4'-Difluoro-6-iodo-biphenyl-3-yl)-1H-imidazol-2-yl]-pyrrolidine-1-carboxylic acid tert-butyl ester (3(19)),
(S)-2-[5-(6-Iodo-5-methyl-biphenyl-3-yl)-1H-imidazol-2-yl]-pyrrolidine-1-carboxylic acid tert-butyl ester (3(20)),
(S)-2-[5-(6-Iodo-5,4'-dimethyl-biphenyl-3-yl)-1H-imidazol-2-yl]-pyrrolidine-1-carboxylic acid tert-butyl ester (3(21)),
(S)-2-[5-(4'-Fluoro-6-iodo-5-methyl-biphenyl-3-yl)-1H-imidazol-2-yl]-pyrrolidine-1-carboxylic acid tert-butyl ester (3(22)),
((S)-1-{(S)-2-[5-(5-Fluoro-6-iodo-biphenyl-3-yl)-1H-imidazol-2-yl]-pyrrolidine-1-carbonyl}-2-methyl-propyl)-carbamic acid methyl ester (3(23)),
((S)-1-{(S)-2-[5-(5-Fluoro-6-iodo-biphenyl-3-yl)-1H-imidazol-2-yl]-pyrrolidine-1-carbonyl}-2-methyl-propyl)-carbamic acid methyl ester (3(24)),
[(S)-1-((S)-2-{5-[4-Iodo-3-((R)-1-phenyl-ethoxy)-phenyl]-1H-imidazol-2-yl}-pyrrolidine-1-carbonyl)-2-methyl-propyl]-carbamic acid methyl ester (3(25)),
((S)-1-{(S)-2-[5-(4-Iodo-3-phenoxy-phenyl)-1H-imidazol-2-yl]-pyrrolidine-1-carbonyl}-2-methyl-propyl)-carbamic acid methyl ester (3(26)),
(S)-2-[5-(4-Iodo-3-phenylsulfanyl-phenyl)-1H-imidazol-2-yl]-pyrrolidine-1-carboxylic acid tert-butyl ester (3(27)),
5-(4-Iodo-3-phenylsulfanyl-phenyl)-2-(S)-pyrrolidin-2-yl-1H-imidazole (3(28)),
((S)-1-{(S)-2-[5-(4-Iodo-3-phenylsulfanyl-phenyl)-1H-imidazol-2-yl]-pyrrolidine-1-carbonyl}-2-methyl-propyl)-carbamic acid methyl ester (3(29)),
[(S)-1-((S)-2-{5-[4-Iodo-3-(methyl-phenyl-amino)-phenyl]-1H-imidazol-2-yl}-pyrrolidine-1-carbonyl)-2-methyl-propyl]-carbamic acid methyl ester (3(30)),
(S)-2-{5-[6-(4-Trimethylsilanyl-buta-1,3-diynyl)-biphenyl-3-yl]-1H-imidazol-2-yl}-pyrrolidine-1-carboxylic acid tert-butyl ester (3(31)),
(S)-2-{5-[3'-tert-Butyl-6-(4-trimethylsilanyl-buta-1,3-diynyl)-biphenyl-3-yl]-1H-imidazol-2-yl}-pyrrolidine-1-carboxylic acid tert-butyl ester (3(32)),
(S)-2-{5-[6-(4-Trimethylsilanyl-buta-1,3-diynyl)-[1,1';3',1"]terphenyl-3-yl]-1H-imidazol-2-yl}-pyrrolidine-1-carboxylic acid tert-butyl ester (3(33)),
(S)-2-{5-[3-Naphthalen-2-yl-4-(4-trimethylsilanyl-buta-1,3-diynyl)-phenyl]-1H-imidazol-2-yl}-pyrrolidine-1-carboxylic acid tert-butyl ester (3(34)),
(S)-2-[5-(6-Buta-1,3-diynyl-biphenyl-3-yl)-1H-imidazol-2-yl]-pyrrolidine-1-carboxylic acid tert-butyl ester (3(35)),
(S)-2-[5-(6-Buta-1,3-diynyl-3'-tert-butyl-biphenyl-3-yl)-1H-imidazol-2-yl]-pyrrolidine-1-carboxylic acid tert-butyl ester (3(36)),
(S)-2-[5-(6-Buta-1,3-diynyl-[1,1';3',1"]terphenyl-3-yl)-1H-imidazol-2-yl]-pyrrolidine-1-carboxylic acid tert-butyl ester (3(37)),
(S)-2-[5-(4-Buta-1,3-diynyl-3-naphthalen-2-yl-phenyl)-1H-imidazol-2-yl]-pyrrolidine-1-carboxylic acid tert-butyl ester (3(38)),
((S)-2-Methyl-1-{(S)-2-[5-(4-trimethylsilanyl-buta-1,3-diynyl)-1H-imidazol-2-yl]-pyrrolidine-1-carbonyl}-propyl)-carbamic acid methyl ester (3(39)),
{(S)-1-[(S)-2-(5-Buta-1,3-diynyl-1H-imidazol-2-yl)-pyrrolidine-1-carbonyl]-2-methyl-propyl}-carbamic acid methyl ester (3(40)).

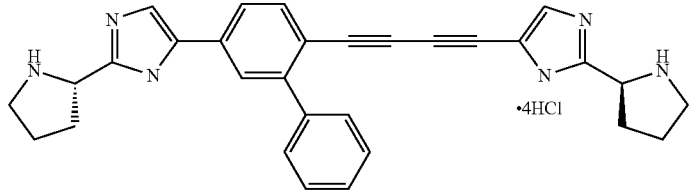

4(1)·4HCl

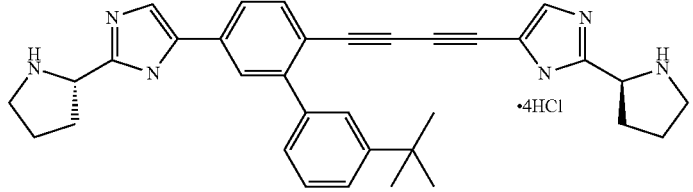

4(2)·4HCl

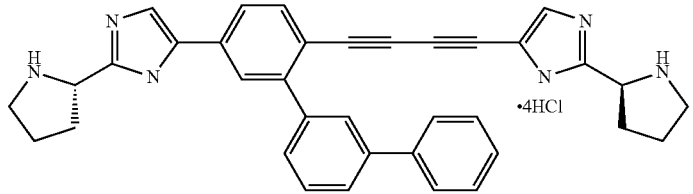

4(3)·4HCl

-continued
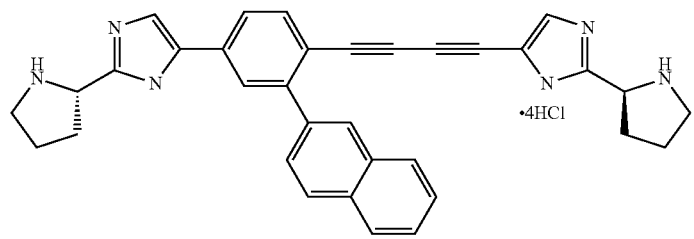
4(4)·4HCl
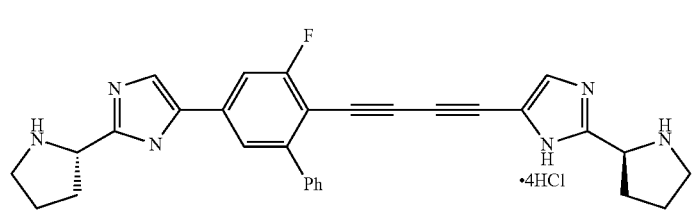
4(5)·4HCl
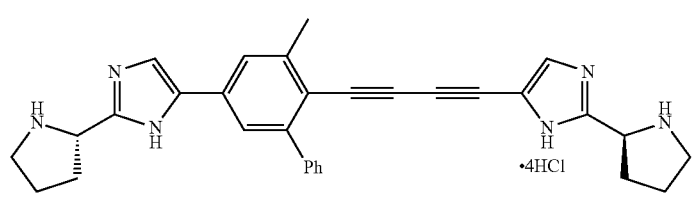
4(6)·4HCl
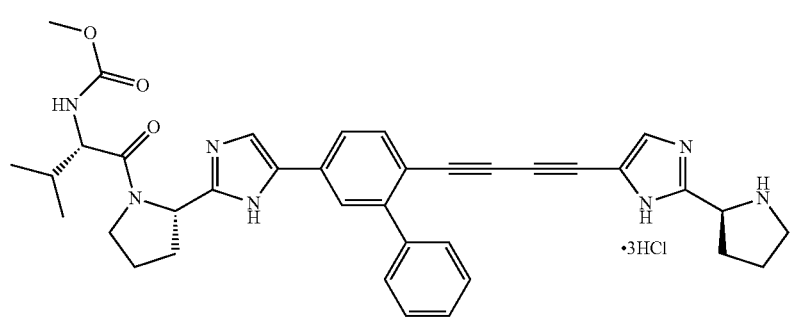
4(7)·3HCl
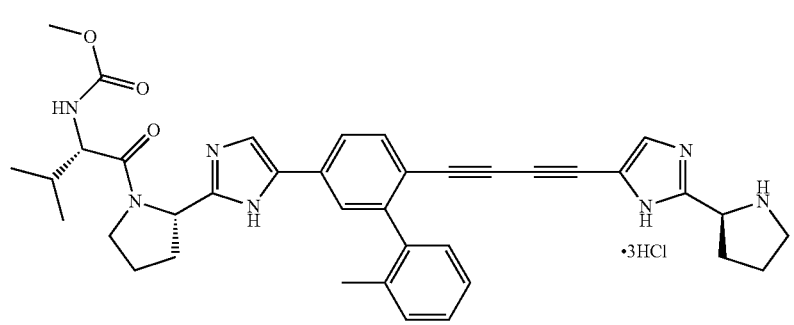
4(8)·3HCl
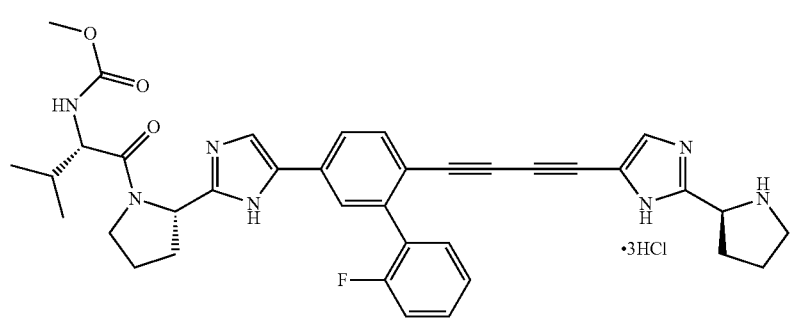
4(9)·3HCl

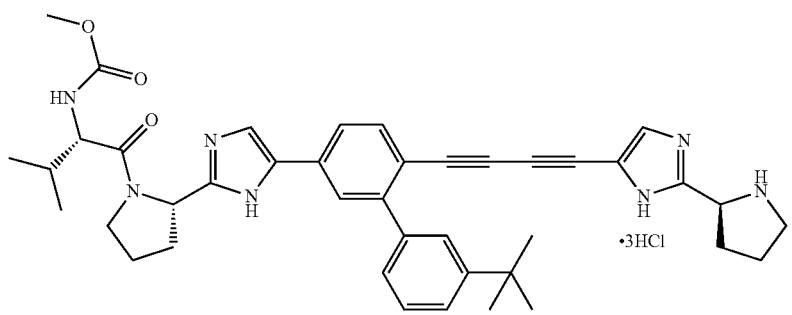
4(10)·3HCl
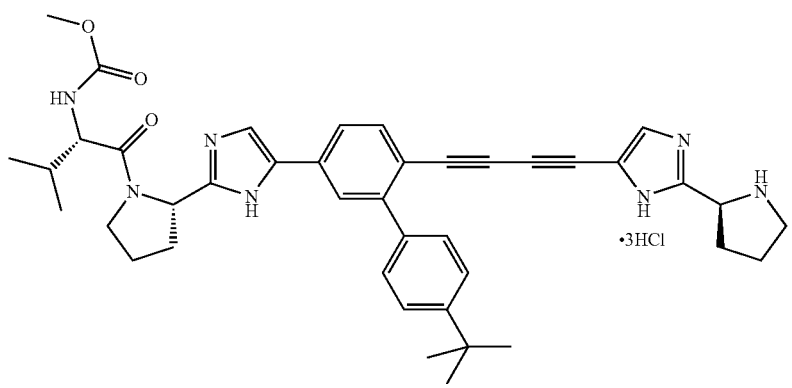
4(11)·3HCl
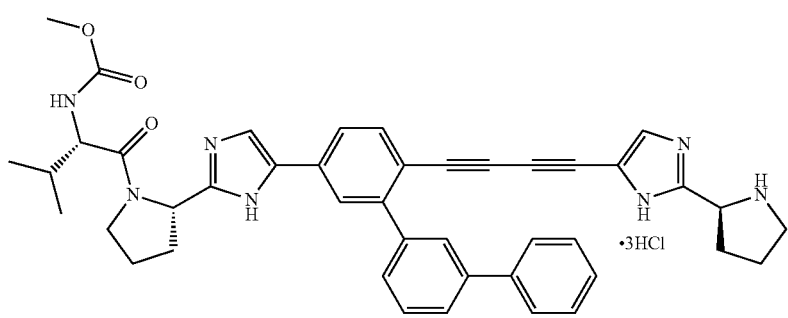
4(12)·3HCl
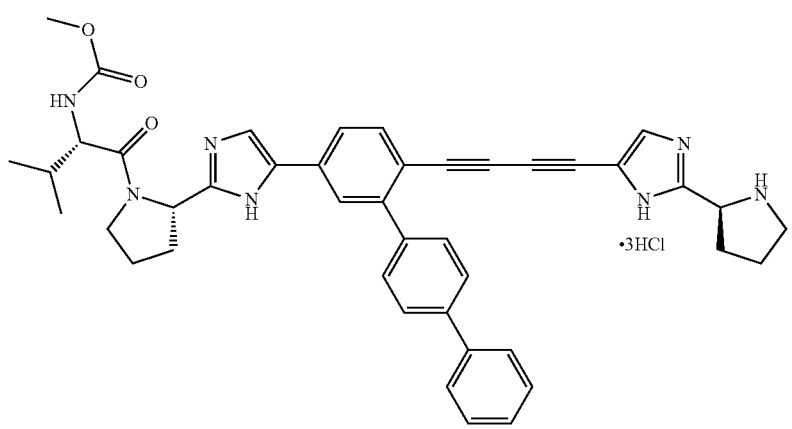
4(13)·3HCl 4(14)·4HCl
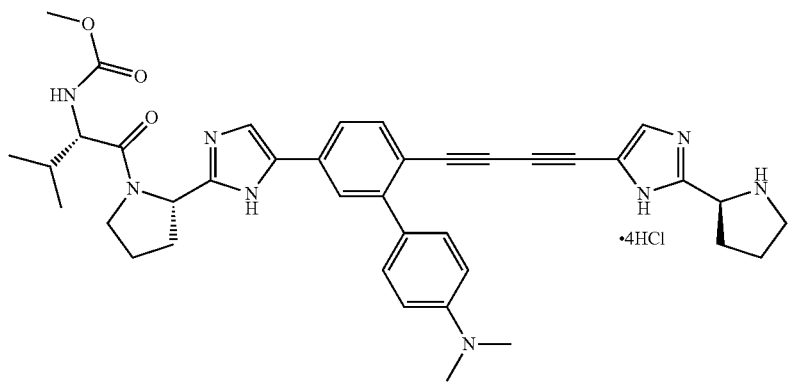
4(15)·5HCl
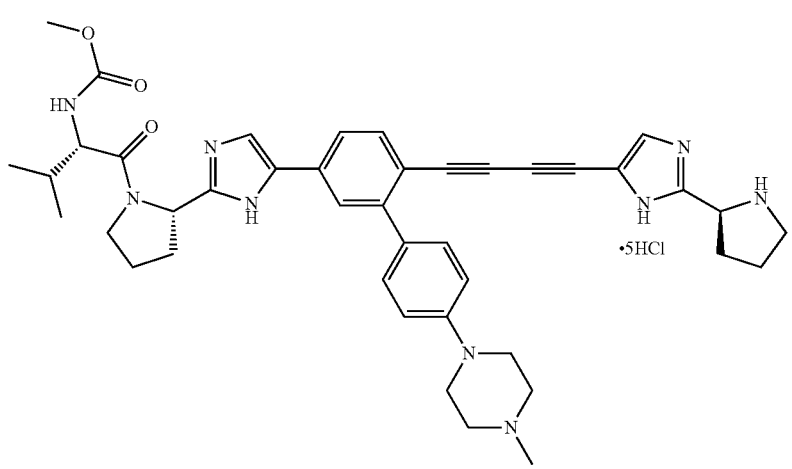
4(16)·4HCl
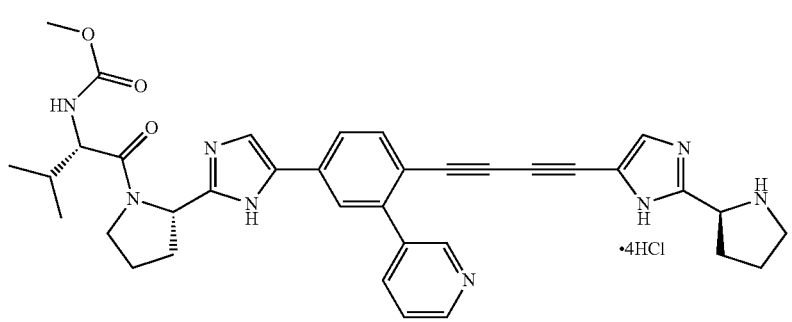
4(17)·3HCl
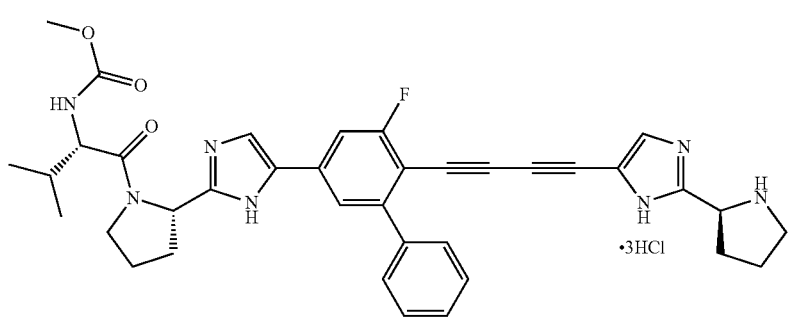

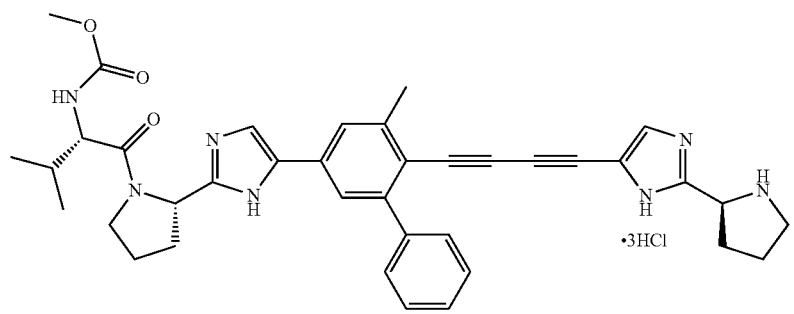
4(18)·3HCl
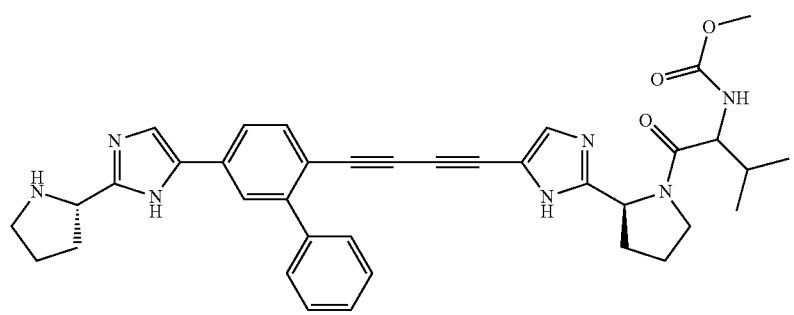
4(19)·3HCl
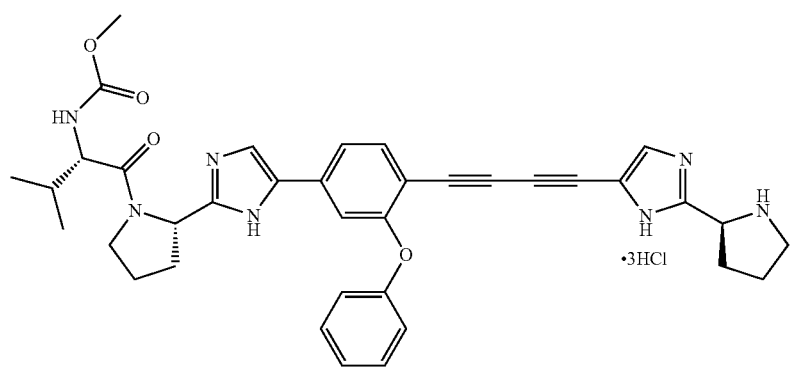
4(20)·3HCl
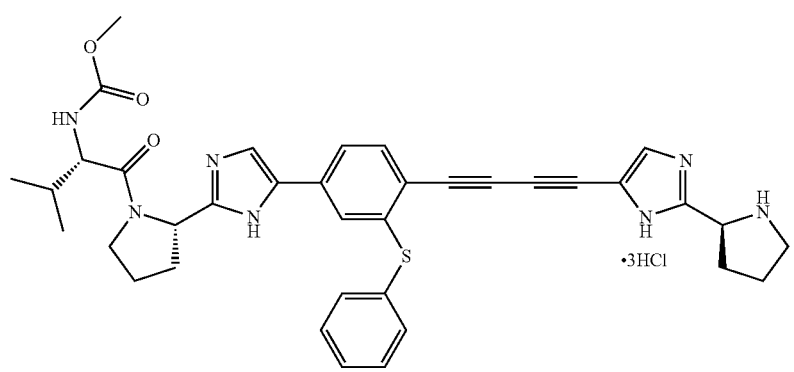
4(21)·3HCl 4(22)·4HCl
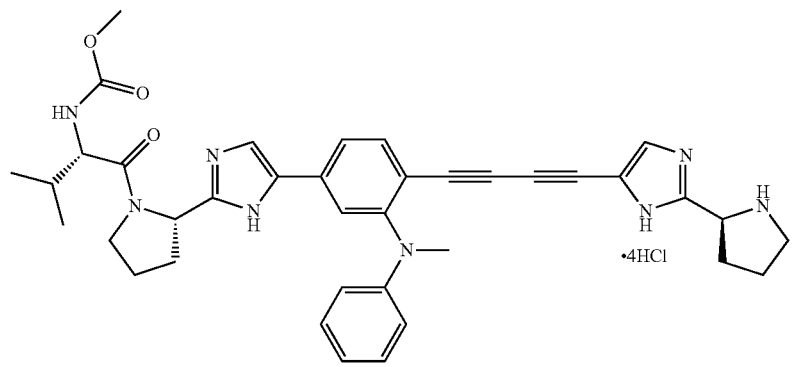
4(23)·3HCl
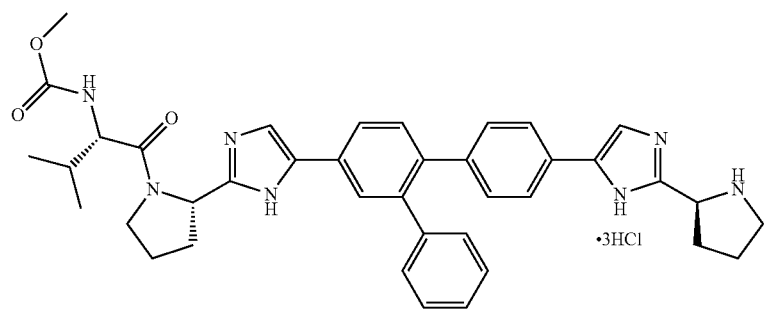
4(24)·3HCl
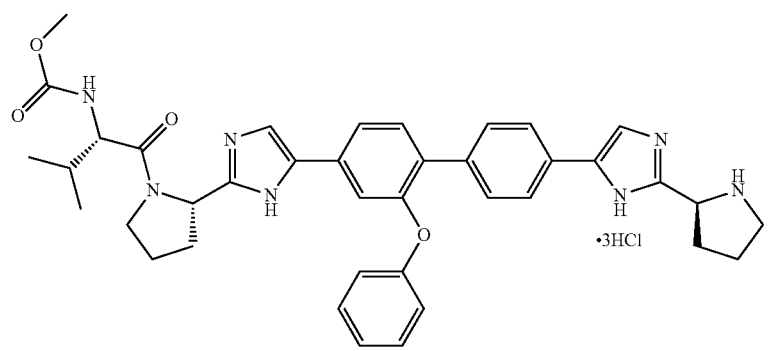
4(25)·3HCl
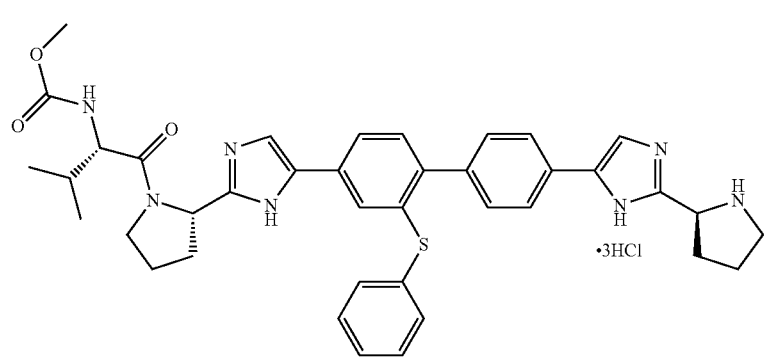

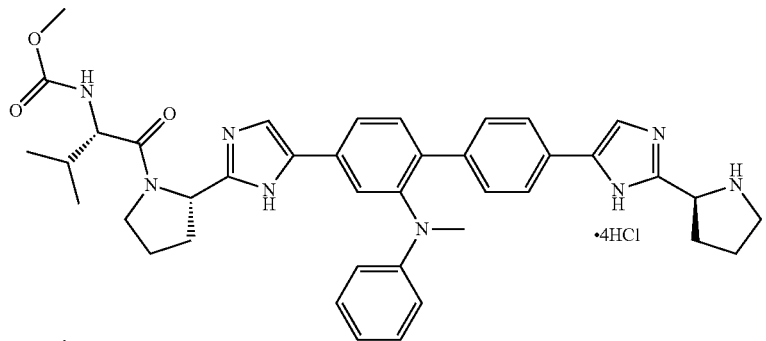

4(26)·4HCl

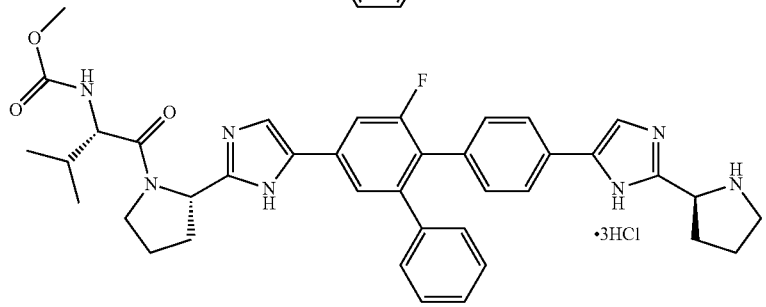

4(27)·3HCl

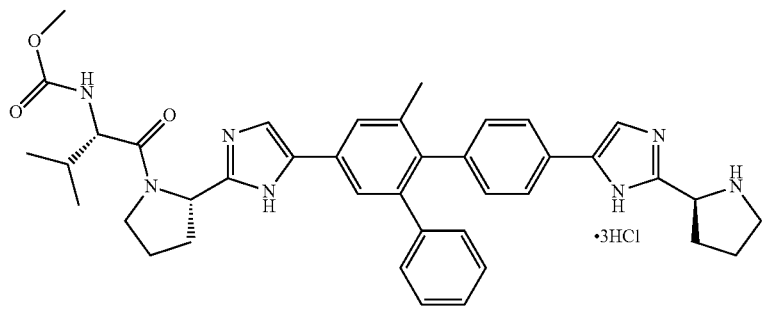

4(28)·3HCl (S)-2-(5-{6-[4-((S)-2-Pyrrolidin-2-yl-3H-imidazol-4-yl)-buta-1,3-diynyl]-biphenyl-3-yl}-1H-imidazol-2-yl)-pyrrolidine tetrahydrochloride (4(1).4HCl), (S)-2-(5-{3'-tert-Butyl-6-[4-((S)-2-pyrrolidin-2-yl-3H-imidazol-4-yl)-buta-1,3-diynyl]-biphenyl-3-yl}-1H-imidazol-2-yl)-pyrrolidine tetrahydrochloride (4(2).4HCl), (S)-2-(5-{6-[4-((S)-2-Pyrrolidin-2-yl-3H-imidazol-4-yl)-buta-1,3-diynyl]-[1,1',3',1"]terphenyl-3-yl}-1H-imidazol-2-yl)-pyrrolidine tetrahydrochloride (4(3).4HCl), (S)-2-(5-{3-Naphthalen-2-yl-4-[4-((S)-2-pyrrolidin-2-yl-3H-imidazol-4-yl)-buta-1,3-diynyl]-phenyl}-1H-imidazol-2-yl)-pyrrolidine tetrahydrochloride (4(4).4HCl), (S)-2-(5-{5-Fluoro-6-[4-((S)-2-pyrrolidin-2-yl-3H-imidazol-4-yl)-buta-1,3-diynyl]-biphenyl-3-yl}-1H-imidazol-2-yl)-pyrrolidine tetrahydrochloride (4(5).4HCl), (S)-2-(5-{5-Methyl-6-[4-((S)-2-pyrrolidin-2-yl-3H-imidazol-4-yl)-buta-1,3-diynyl]-biphenyl-3-yl}-1H-imidazol-2-yl)-pyrrolidine tetrahydrochloride (4(6).4HCl), {(S)-2-Methyl-1-((S)-2-(5-{6-[4-((S)-2-pyrrolidin-2-yl-3H-imidazol-4-yl)-1H-imidazol-2-yl)-pyrrolidine-1-carbonyl]-propyl}-carbamic acid methyl ester trihydrochloride (4(7).3HCl), {(S)-2-Methyl-1-[(S)-2-(5-{2'-methyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester trihydrochloride (4(8).3HCl), {(S)-1-[(S)-2-(5-{2'-Fluoro-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(9).3HCl), {(S)-1-[(S)-2-(5-{3'-tert-Butyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(10).3HCl), {(S)-1-[(S)-2-(5-{4'-tert-Butyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(11).3HCl), {(S)-2-Methyl-1-[(S)-2-(5-{6-[4-((S)-2-pyrrolidin-2-yl-3H-imidazol-4-yl)-buta-1,3-diynyl]-[1,1';3',1"]terphenyl-3-yl}-1H-imidazol-2-yl)-pyrrolidine-1-carbonyl]-propyl}-carbamic acid methyl ester trihydrochloride (4(12).3HCl), {(S)-2-Methyl-1-[(S)-2-(5-{6-[4-((S)-2-pyrrolidin-2-yl-3H-imidazol-4-yl)-buta-1,3-diynyl]-[1,1';4',1"]terphenyl-3-yl}-1H-imidazol-2-yl)-pyrrolidine-1-carbonyl]-propyl}-carbamic acid methyl ester trihydrochloride (4(13).3HCl), {(S)-1-[(S)-2-(5-{4'-Dimethylamino-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester tetrahydrochloride (4(14).4HCl), {(S)-2-Methyl-1-[(S)-2-(5-{4'-(4-methyl-piperazin-1-yl)-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester pentahydrochloride (4(15).5HCl), {(S)-2-Methyl-1-[(S)-2-(5-{3-pyridin-3-yl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester tetrahydrochloride (4(16).4HCl), {(S)-1-[(S)-2-(5-{5-Fluoro-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(17).3HCl), {(S)-2-Methyl-1-[(S)-2-(5-{5-methyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester trihydrochloride (4(18).3HCl), {(S)-2-Methyl-1-[(S)-2-(5-{4-[5-((S)-2-pyrrolidin-2-yl-3H-imidazol-4-yl)-biphenyl-2-yl]-buta-1,3-diynyl}-1H-imidazol-2-yl)-pyrrolidine-1-carbonyl]-propyl}-carbamic acid methyl ester trihydrochloride (4(19).3HCl), {(S)-2-Methyl-1-[(S)-2-(5-{3-phenoxy-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester trihydrochloride (4(20).3HCl), (S)-2-Methyl-1-[(S)-2-(5-{3-phenyl sulfanyl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester trihydrochloride (4(21).3HCl), 1H-imidazol-2-yl}-pyrrolidine-1-carbonyl)-propyl]-carbamic acid methyl ester tetrahydrochloride (4(26).4HCl),

[(S)-1-((S)-2-{5-[6'-Fluoro-4-((S)-2-pyrrolidin-2-yl-3H-imidazol-4-yl)-[1,1';2',1"]terphenyl-4'-yl]-1H-imidazol-2-yl}-pyrrolidine-1-carbonyl)-2-methyl-propyl]-carbamic acid methyl ester trihydrochloride (4(27).3HCl),

[(S)-2-Methyl-1-((S)-2-{5-[6'-methyl-4-((S)-2-pyrrolidin-2-yl-3H-imidazol-4-yl)-[1,1';2',1"]terphenyl-4'-yl]-1H-imidazol-2-yl}-pyrrolidine-1-carbonyl)-propyl]-carbamic acid methyl ester trihydrochloride (4(28).3HCl).

The starting materials employed in the above synthesis of novel compounds of formula 1-4 and stereoisomers, salts, hydrates, solvates, or crystalline forms thereof are commercially available compounds or they can be easily prepared by methods known in the art. The quality of the compounds was monitored by LCMS and NMR.

The synthesis of methyl [(S)-1-((S)-2-{5-[(5-{2-[(S)-1-((5)-2-methoxycarbonylamino-3-methylbutyryl)pyrrolidin-2-yl]-1H-imidazol-5-yl}biphenyl-2-yl)buta-1,3-diynyl]-1H-imidazol-2-yl}pyrrolidine-1-carbonyl)-2-methylpropyl]-carbamate dihydrochlorides ((2(1)-2(6)).2HCl), and dimesilates (2(1), 2(4)).2CH$_3$SO$_3$H was carried by acylating intermediates (4(1).3HCl-4(6).3HCl). Moc-L-Valine (Scheme 1) and subsequent transformation of the resulting inhibitors 2(1)-2(6) into the corresponding salts.

Scheme 1

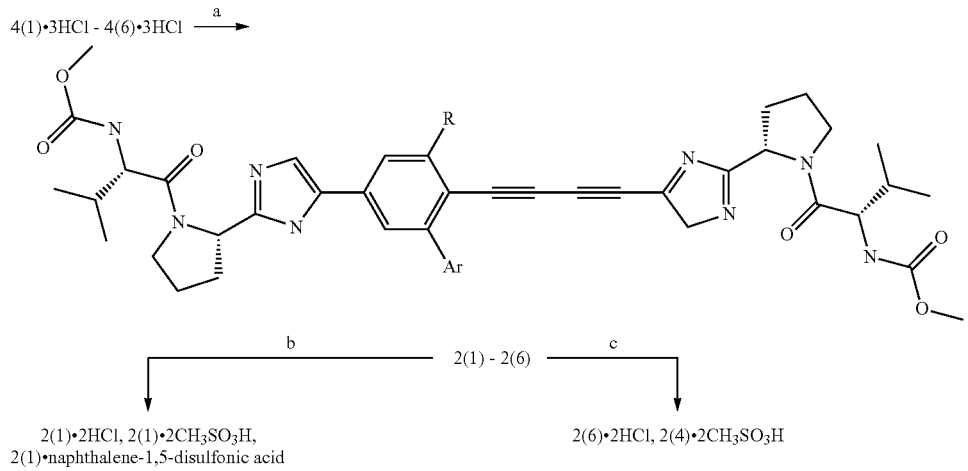

where R=H (4(1)-4(4)).3HCl, (2(1)-2(4)).2HCl, (2(1), 2(4)).2CH$_3$SO$_3$H, 2(1).naphthalene-1,5-disulfonic acid); F (4(17).3HCl, 2(5).2HCl); Me (4(18).3HCl, 2(6).2HCl). Ar=Ph (4(1).4HCl, 2(1).2HCl, 2(1).2CH$_3$SO$_3$H, 2(1).naphthalene-1,5-disulfonic acid, 2(5).2HCl, 2(6).2HCl), 3-tert-Bu-Ph (4(2).4HCl, 2(2).2HCl), 3-Ph-Ph (4(1).4HCl, 2(3).2HCl), 2-naphthyl (4(1).4HCl, 2(4).2HCl, 2(4).2CH$_3$SO$_3$H). Reagents and conditions: (a) Moc-L-Val-OH, HATU, DMF, DIPEA, 4° C. (b) Acetone, HCl, dioxane; acetone, CH$_3$SO$_3$H, dioxane; or ethanol, naphthaline-1,5-disulphonic acid. (c) Acetone, HCl, dioxane; acetone, CH$_3$SO$_3$H, dioxane.

{(S)-2-Methyl-1-[(S)-2-(5-{3-(methyl-phenyl-amino)-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester tetrahydrochloride (4(22).4HCl),

[(S)-2-Methyl-1-((S)-2-{5-[4-((S)-2-pyrrolidin-2-yl-3H-imidazol-4-yl)-[1,1';2',1"]terphenyl-4'-yl]-1H-imidazol-2-yl}-pyrrolidine-1-carbonyl)-propyl]-carbamic acid methyl ester trihydrochloride (4(23).3HCl),

[(S)-2-Methyl-1-((S)-2-{5-[2-phenoxy-4'-((S)-2-pyrrolidin-2-yl-3H-imidazol-4-yl)-biphenyl-4-yl]-1H-imidazol-2-yl}-pyrrolidine-1-carbonyl)-propyl]-carbamic acid methyl ester trihydrochloride (4(24).3HCl),

[(S)-2-Methyl-1-((S)-2-{5-[2-phenylsulfanyl-4'-((S)-2-pyrrolidin-2-yl-3H-imidazol-4-yl)-biphenyl-4-yl]-1H-imidazol-2-yl}-pyrrolidine-1-carbonyl)-propyl]-carbamic acid methyl ester trihydrochloride (4(25).3HCl),

[(S)-2-Methyl-1-((S)-2-{5-[2-(methyl-phenyl-amino)-4'-((S)-2-pyrrolidin-2-yl-3H-imidazol-4-yl)-biphenyl-4-yl]-

Methyl [(S)-1-((S)-2-{5-[4-(4-{2-[(S)-1-((R)-2-methoxycarbonylamino-2-phenyl-acetyl)-pyrrolidin-2-yl]-3H-imidazol-4-yl}-buta-1,3-diynyl)-phenyl]-1H-imidazol-2-yl}-pyrrolidine-1-carbonyl)-2-methyl-propyl]-carbamates hydrochlorides ((2(7)-2(21)).nHCl) were obtained by the acylation of intermediates (4(7)-4(18), 4(20)-4(22)).nHCl Moc-(R)-phenylglycine (Scheme 2).

Scheme 2

(4(7)-4(18), 4(20)-4(22))·nHCl →<sup>a</sup>

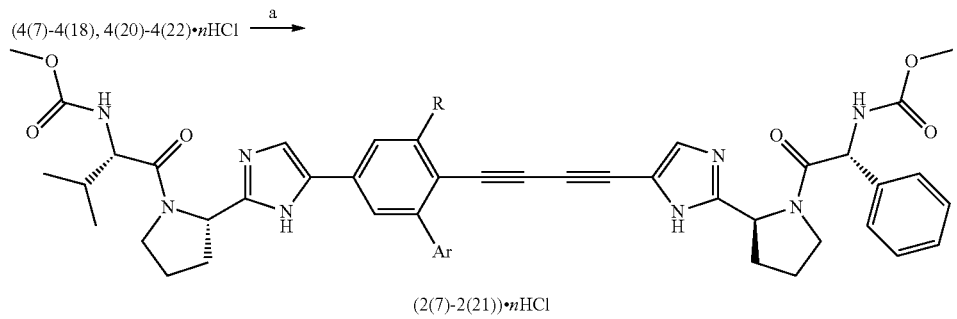

(2(7)-2(21))·nHCl where Ar=Ph (4(7).3HCl, 4(17).3HCl, 4(18).3HCl, 2(7).2HCl, 2(17).2HCl, 2(18).2HCl); 2-Me-Ph (4(8).3HCl), 2(8).2HCl); 2-F-Ph (4(9).3HCl), 2(9).2HCl); 3-t-Bu-Ph (4(10).3HCl, 2(10).2HCl); 4-t-Bu-Ph (4(11).3HCl, 2(11).2HCl); 3-Ph-Ph (4(12).3HCl, 2(12).2HCl); 4-Ph-Ph (4(13).3HCl, 2(13).2HCl); 4-Me$_2$N-Ph (4(14).4HCl, 2(14).3HCl); 4-(4-methylpiperazin-1-yl)-Ph (4(15).5HCl, 2(15).4HCl); 3-Py (4(16).4HCl, 2(16).2HCl); PhO (4(20), 2(19).2HCl); PhS (4(21), 2(20).2HCl); PhMeN (4(22), 2(21).2HCl). R=H ((4(7)-4(16), 4(19)-4(22)).nHCl), F (4(17).3HCl), Me (4(18).3HCl). Reagents and conditions: (a) Moc-(R)-PhGly-OH, HATU, DMF, DIPEA, −20° C.

Similarly, methyl ((S)-1-{(S)-2-[5-(4'-{2-[(S)-1-((R)-2-methoxy carbonylamino-2-phenyl-acetyl)-pyrrolidin-2-yl]-3H-imidazol-4-yl}-biphenyl-4-yl)-1H-imidazol-2-yl]-pyrrolidine-1-carbonyl}-2-methyl-propyl)-carbamates hydrochlorides ((2(22)-2(27)).nHCl) and methyl {(S)-1-[(S)-2-(5-{6-[(2-{(S)-1-[(S)-2-(methoxycarbonylamino)-2-phenylacetyl]pyrrolidin-2-yl}-1H-imidazol-5-yl)buta-1,3-diynyl]biphenyl-3-yl}-1H-imidazol-2-yl)pyrrolidine-1-carbonyl]-2-methylpropyl}-carbamate dihydrochloride (2(28).2HCl) were obtained. In this case, intermediates (4(25)-4(30)).nHCl (Scheme 3) and 4(7).3HCl (Scheme 4) were used.

Scheme 3

(4(25)-4(30))·nHCl →<sup>a</sup>

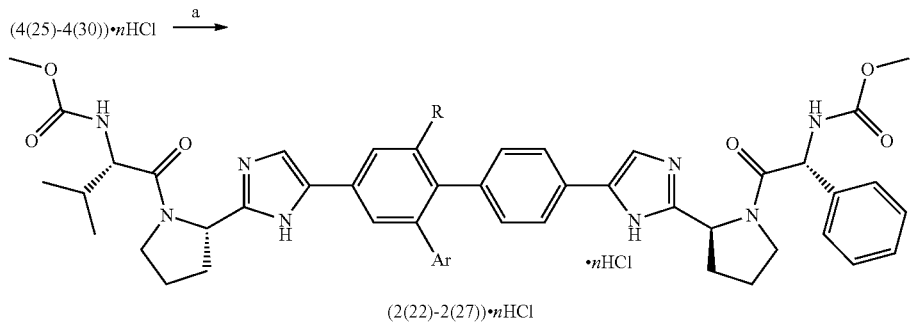

(2(22)-2(27))·nHCl where Ar=Ph (4(7).3HCl, 4(29) 3HCl, 4(30).3HCl, 2(22). 2HCl, 2(26).2HCl, 2(27).2HCl); PhO (4(26), 2(23).2HCl); PhS (4(27), 2(24).2HCl); PhMeN (4(27), 2(25).2HCl). R=H ((4(25)-4(28)).nHCl, (2(22)-2(25)).nHCl; F (4(29).3HCl, 2(26).2HCl), Me (4(30).3HCl, 2(27).2HCl). Reagents and conditions: (a) Moc-(R)-PhGly-OH, HATU, DMF, DIPEA, −20° C.

Scheme 4

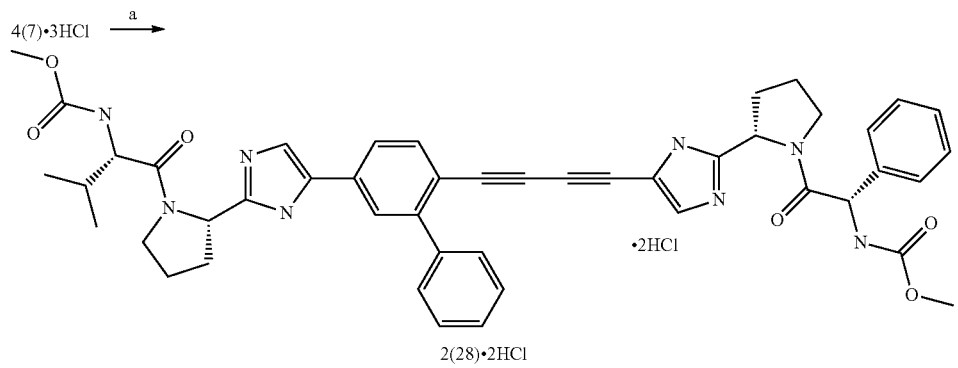

Reagents and conditions: (a) Moc-(R)-PhGly-OH, HATU, DMF, DIPEA, −20° C.

30  Methyl {(S)-1-[(S)-2-(5-{5-[(2-{(S)-1-[(S)-2-(methoxy-carbonylamino)-2-phenylacetyl]pyrrolidin-2-yl}-1H-imidazol-5-yl)biphenyl-2-yl]buta-1,3-diynyl}-1H-imidazol-2-yl)pyrrolidine-1-carbonyl]-2-methylpropyl}-carbamate dihydrochloride (2(29).2HCl) and methyl {(S)-1-[(S)-2-(5-
35  {5-[(2-{(S)-1-[(R)-2-(methoxycarbonylamino)-2-phenylacetyl]pyrrolidin-2-yl}-1H-imidazol-5-yl)biphenyl-2-yl]buta-1,3-diynyl}-1H-imidazol-2-yl)pyrrolidine-1-carbonyl]-2-methylpropyl}-carbamate dihydrochloride (2(30).2HCl) were obtained (Scheme 5) by acylation of intermediate 4(9).3HCl by Moc-(S)- and Moc-(R)-phenylglicine, respectively.

Scheme 5

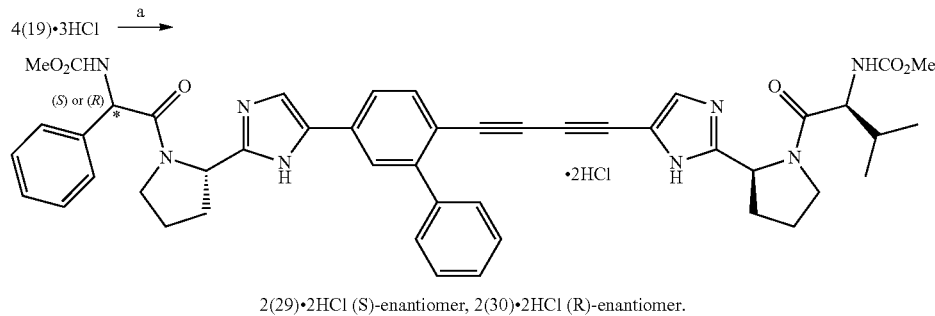

2(29)•2HCl (S)-enantiomer, 2(30)•2HCl (R)-enantiomer.

Reagents and conditions: (a) Moc-(S)-PhGly-OH for 2(20).2HCl and Moc-(R)-PhGly-OH for 2(21).2HCl, HATU, DMF, DIPEA, −20° C.

Methyl [(S)-1-((S)-2-{5-[(4-{2-[(S)-1-((S)-2-methoxycarbonylamino-3-methylbutyryl)pyrrolidin-2-yl]-1H-imidazol-5-yl}-2-[(S)-1-phenylethoxy]phenyl)buta-1,3-diynyl]-1H-imidazol-2-yl}pyrrolidine-1-carbonyl)-2-methylpropyl]-carbamate 2(31) were obtained by reaction of iodide 3(25) and methyl {(S)-1-[(S)-2-(5-buta-1,3-diynyl-1H-imidazol-2-yl)-pyrrolidine-1-carbonyl]-2-methyl-propyl}-carbamate (Scheme 6).

Scheme 6

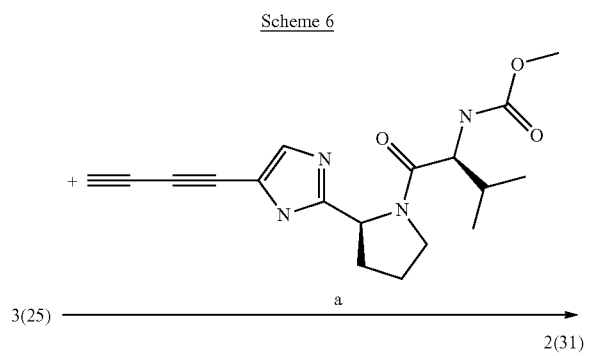

Reagents and conditions: (a) Pd(PPh$_3$)$_4$, CuI, DMF, Et$_3$N, 45° C.

The intermediates 3 and 4 were obtained using schemes 7-23 presented below.

tert-Butyl (S)-2-[5-(3-aryl-4-iodo-phenyl)-1H-imidazol-2-yl]-pyrrolidine-1-carboxylates (3(1)-3(6)) were obtained by starting from N-(4-acetyl-2-bromophenyl) acetamide (10) and phenylboronic acid (11) in Scheme 7.

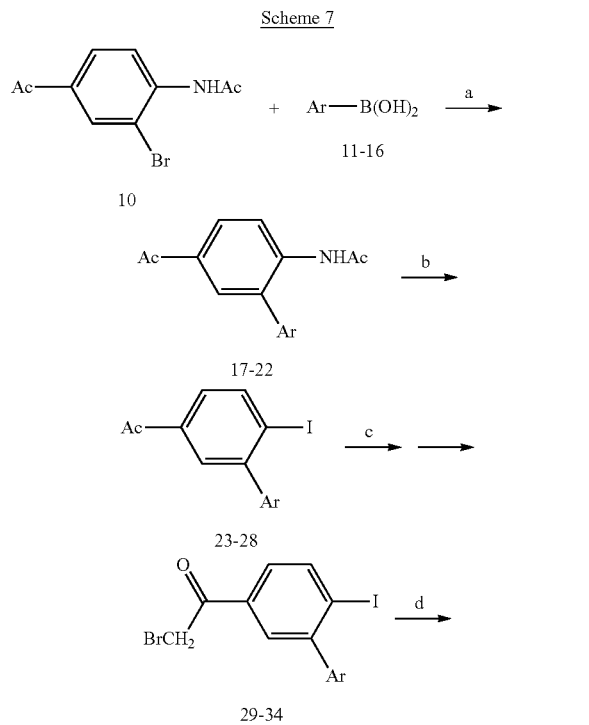

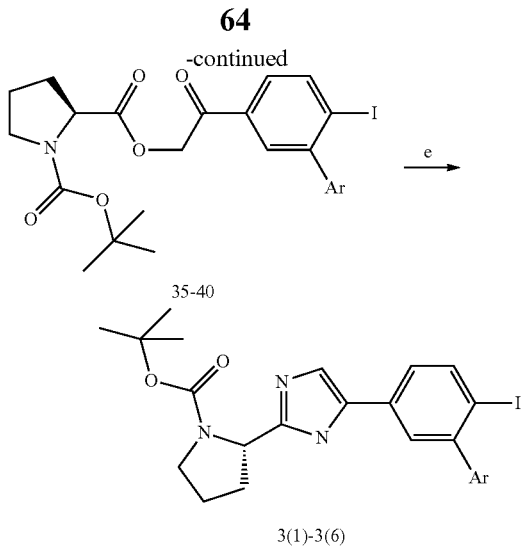

where Ar=Ph (11, 17, 23, 29, 35, 3(1)), 4-Me-Ph (12, 18, 24, 30, 36, 3(2)), 3-tert-Bu-Ph (13, 19, 25, 31, 37, 3(3)), 4-F-Ph (14, 20, 26, 32, 38, 3(4)), 3-Ph-Ph (15, 21, 27, 33, 39, 3(5)), and 2-naphthyl (16, 22, 28, 34, 40, 3(6)). Reagents and conditions: (a) Pd(PPh$_3$)$_2$Cl$_2$, Na$_2$CO$_3$, EtOH, H$_2$O, 80° C.; (b) i—HCl, reflux, 5 h, ii—HCl, NaNO$_2$, KI; (c) Br$_2$, AcOH; (d) Boc-L-proline, DIPEA, MeCN; (e) NH$_4$OAc, PhMe, 100° C.;

Methyl ((S)-1-{(S)-2-[5-(3-aryl-4-iodo-phenyl)-1H-imidazol-2-yl]-pyrrolidine-1-carbonyl}-2-methyl-propyl)-carbamates 3(7)-3(16) were obtained by starting from 2-bromo-1-(3-bromo-4-nitro-phenyl)-ethanone (41) and (S)-2-[2-(3-bromo-4-nitrophenyl)-2-oxoethyl] 1-tert-butyl pyrrolidine-1,2-dicarboxylate (42) in Scheme 8. Compound 42 ($^1$H NMR (CDCl$_3$, 400 MHz) δ 8.26 (s, 1H), 7.97 (m, 1H), 7.92 (m, 1H), 5.34 (m, 2H), 4.45 (m, 1H), 3.52 (m, 2H), 2.30 (m, 2H), 2.05 (m, 1H), 1.96 (m, 1H), 1.46, 1.47 (2 s, 9H)) was synthesized according to the procedure given above for compounds 35-40 and according to S. Pasaribu and L. Williams [*Austr. J. Chem.* (1975), 28(5), 1023-1030].

Scheme 8

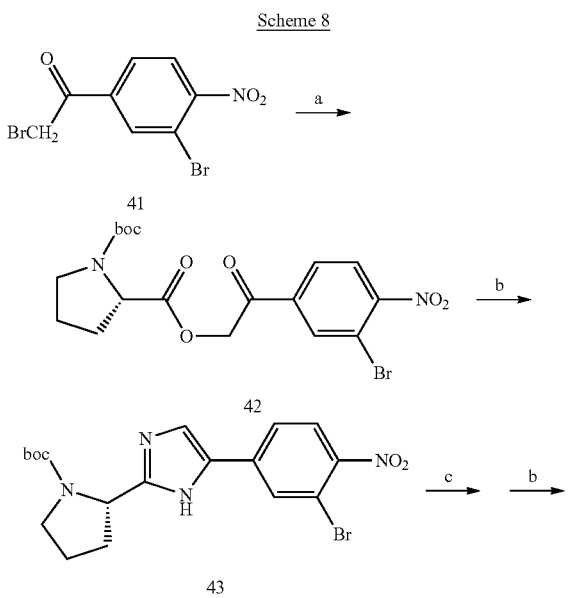

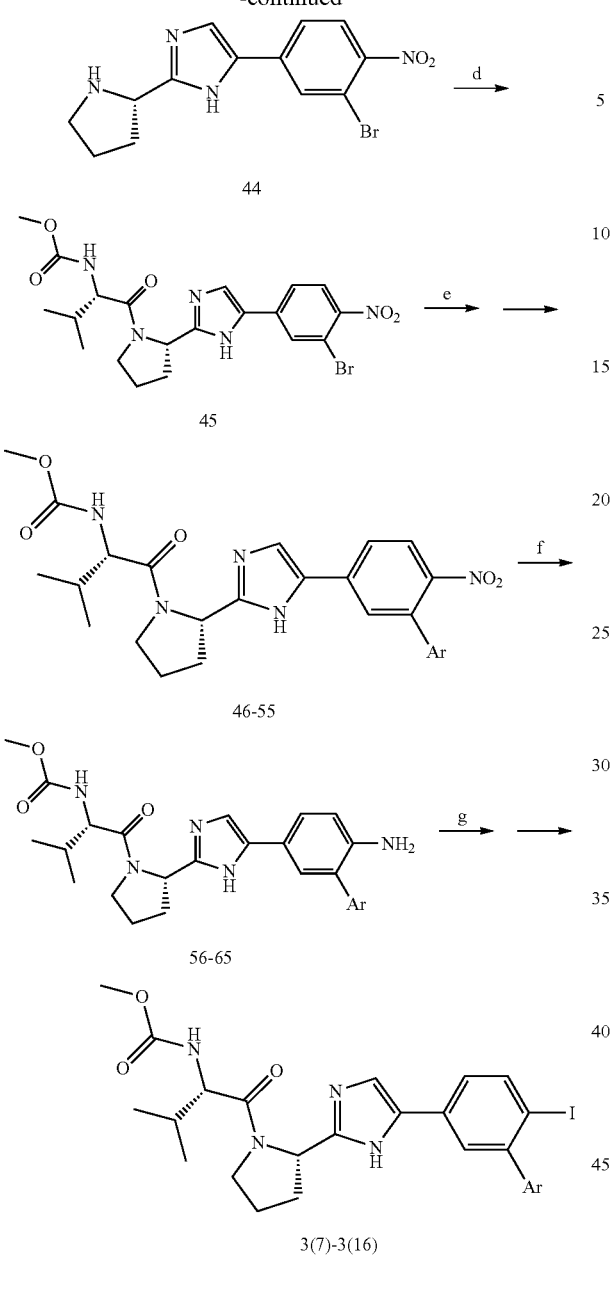
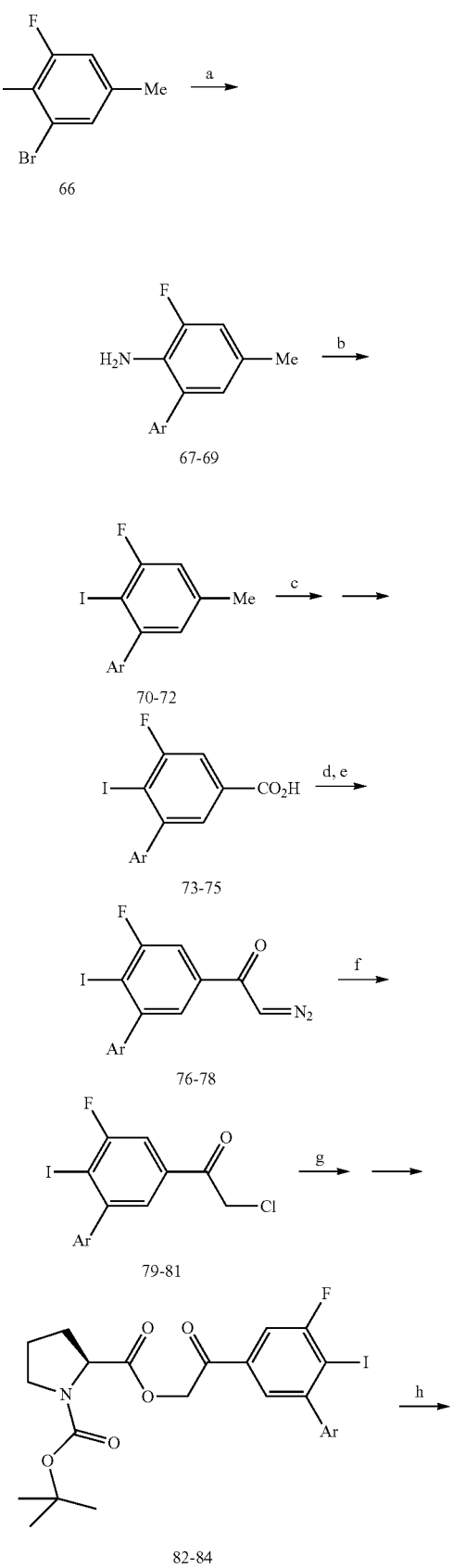

Scheme 9.

where Ar=Ph (46, 56, 3(7)), 2-F-Ph (47, 57, 3(8)), 2-Me-Ph (48, 58, 3(9)), 3-tert-Bu-Ph (49, 59, 3(10)), 4-t-Bu-Ph (50, 60, 3(11)), 3-Ph-Ph (51, 61, 3(12)), 4-Ph-Ph (52, 62, 3(13)), 4-Me$_2$N-Ph (53, 63, 3(14)), 4-(4-methylpiperazin-1-yl)-Ph (54, 64, 3(15)), and 3-Py (55, 65, 3(16)). Reagents and conditions: (a) Boc-L-proline, DIPEA, MeCN; (b) NH$_4$OAc, PhMe, 100° C.; (c) HCl, dioxane; (d) Moc-L-Val-OH, HATU, DMF, DIPEA, 4° C.; (e) ArB(OH)$_2$, Pd(PPh$_3$)$_2$Cl$_2$, Na$_2$CO$_3$, EtOH, H$_2$O, 65° C.; (f) H$_2$, Pd/C, EtOH; (g) TsOH.H$_2$O, NaNO$_2$, KI, MeCN, H$_2$O.

The synthesis of (S)-tert-butyl 2-[5-(5-fluoro-6-iodobiphenyl-3-yl)-1H-imidazol-2-yl]pyrrolidine-1-carboxylate (3(15)-3(17)) was carried out according to Scheme 9 starting from 2-bromo-6-fluoro-4-methylaniline (66) [WO 2007036715] and phenylboronic acid.

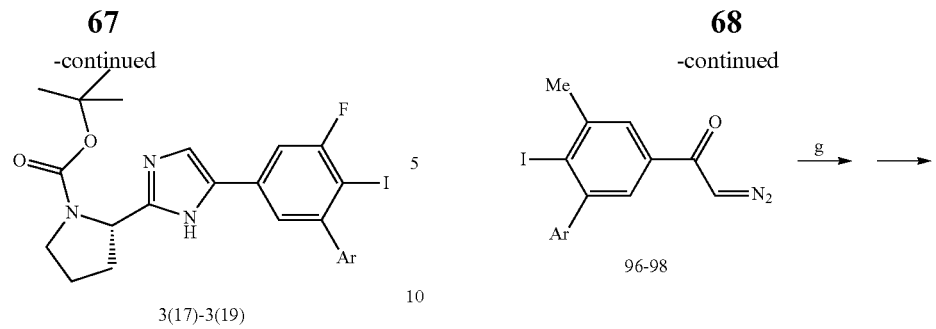

3(17)-3(19)

where Ar is Ph (67, 70, 73, 76, 79, 82, 3(17)), 4-Me-Ph (68, 71, 74, 77, 80, 83, 3(18)), 4-F-Ph (69, 72, 75, 78, 81, 84, 3(19)). Reagents and conditions: (a) PhB(OH)$_2$, Na$_2$CO$_3$, Pd(PPh$_3$)$_2$Cl$_2$, EtOH, H$_2$O, 80° C.; (b) TsOH.H$_2$O, NaNO$_2$, KI, t-BuOH, H$_2$O; (c) KMnO$_4$, Py, H$_2$O, 4 h, 70-80° C.; (d) (COCl)$_2$, DCM; (e) MeCN, TMS-diazomethane, 15 h, 4° C.; (f) HCl, EtOAc; (g) Boc-L-proline, DIPEA, MeCN; (h) NH$_4$OAc, PhMe, 100° C.

Methyl (S)-tert-butyl 2-[5-(6-iodo-5-methylbiphenyl-3-yl)-1H-imidazol-2-yl]pyrrolidine-1-carboxylates (3(20)-3(22)) were obtained by starting from methyl 4-amino-5-methylbenzoate (85) in Scheme 10.

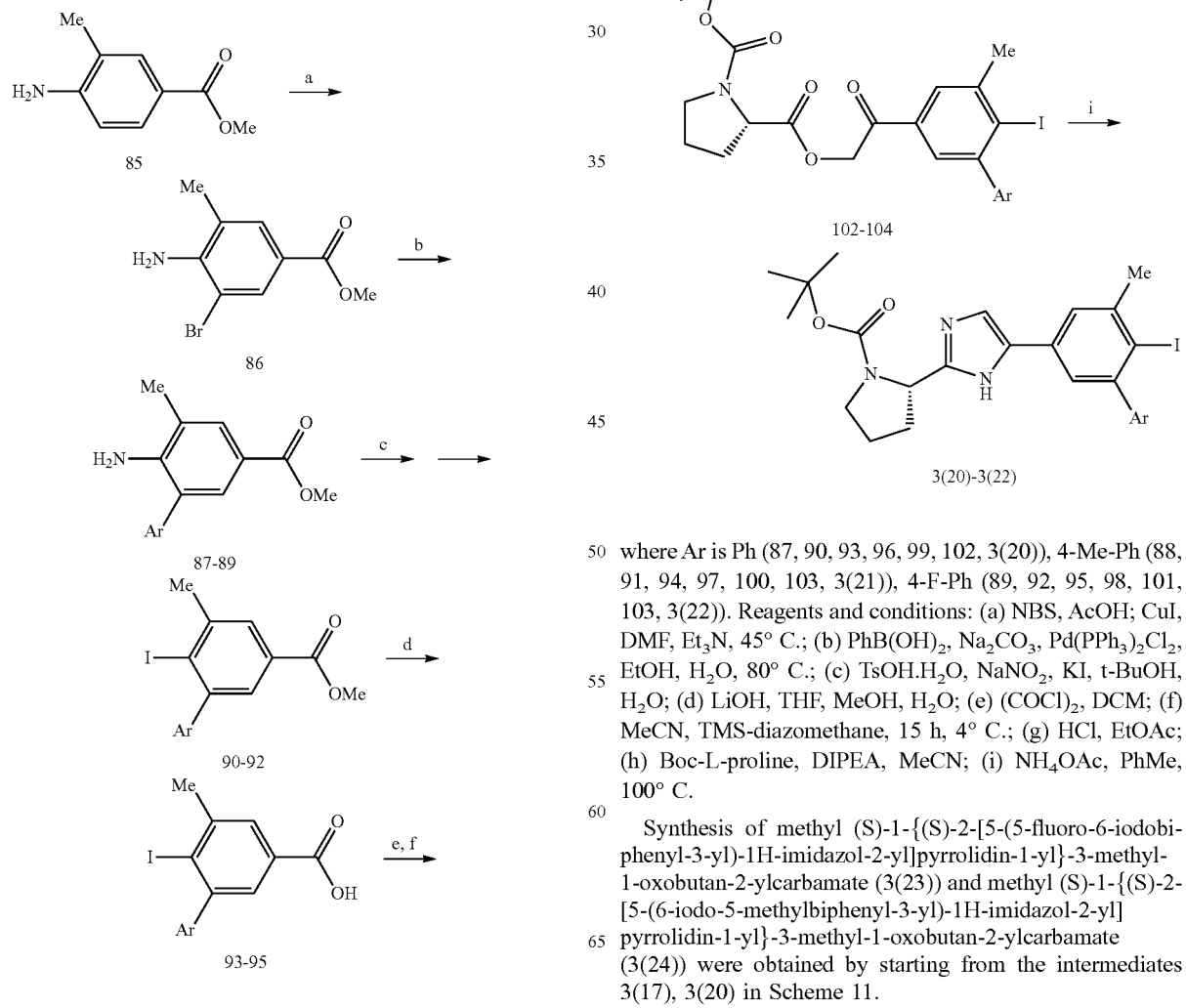

Scheme 10

3(20)-3(22)

where Ar is Ph (87, 90, 93, 96, 99, 102, 3(20)), 4-Me-Ph (88, 91, 94, 97, 100, 103, 3(21)), 4-F-Ph (89, 92, 95, 98, 101, 103, 3(22)). Reagents and conditions: (a) NBS, AcOH; CuI, DMF, Et$_3$N, 45° C.; (b) PhB(OH)$_2$, Na$_2$CO$_3$, Pd(PPh$_3$)$_2$Cl$_2$, EtOH, H$_2$O, 80° C.; (c) TsOH.H$_2$O, NaNO$_2$, KI, t-BuOH, H$_2$O; (d) LiOH, THF, MeOH, H$_2$O; (e) (COCl)$_2$, DCM; (f) MeCN, TMS-diazomethane, 15 h, 4° C.; (g) HCl, EtOAc; (h) Boc-L-proline, DIPEA, MeCN; (i) NH$_4$OAc, PhMe, 100° C.

Synthesis of methyl (S)-1-{(S)-2-[5-(5-fluoro-6-iodobiphenyl-3-yl)-1H-imidazol-2-yl]pyrrolidin-1-yl}-3-methyl-1-oxobutan-2-ylcarbamate (3(23)) and methyl (S)-1-{(S)-2-[5-(6-iodo-5-methylbiphenyl-3-yl)-1H-imidazol-2-yl]pyrrolidin-1-yl}-3-methyl-1-oxobutan-2-ylcarbamate (3(24)) were obtained by starting from the intermediates 3(17), 3(20) in Scheme 11.

Scheme 11

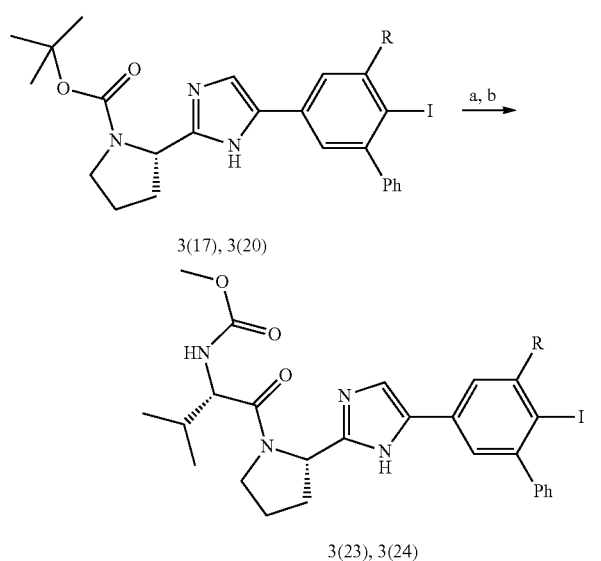

where R is F (3(17), 3(23)) and Me (3(20), 3(24)). Reagents and conditions: (a) HCl, dioxane; (b) Moc-L-Val-OH, HATU, DMF, DIPEA, 4° C.

Methyl (S)-1-((S)-2-{5-[4-iodo-3-(S)-1-phenylethoxy) phenyl]-1H-imidazol-2-yl}pyrrolidin-1-yl)-3-methyl-1-oxobutan-2-ylcarbamate (3(25)) were obtained by starting from 4-bromo-2-fluoro-1-nitro-benzene (105) in Scheme 12.

Scheme 12

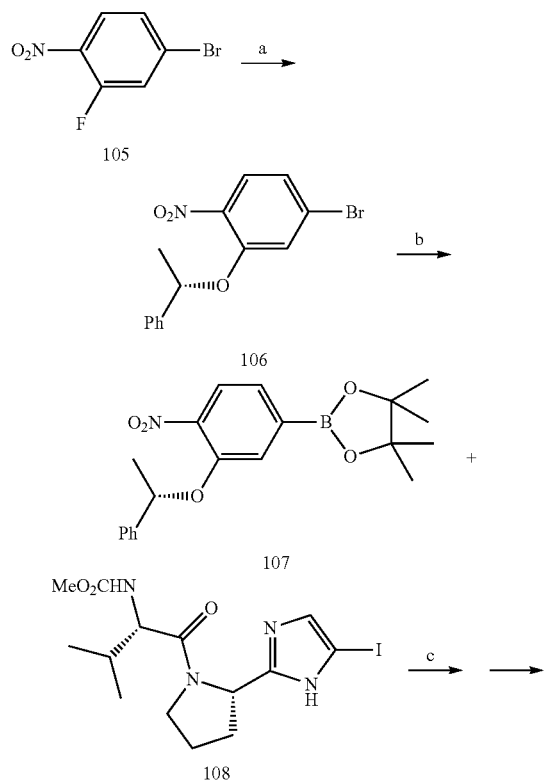

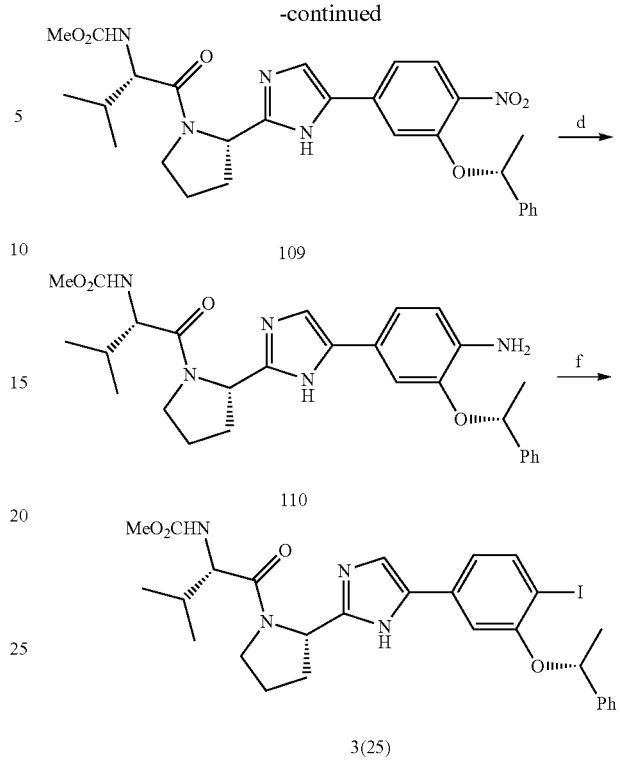

Reagents and conditions: (a) NaH, (S)-1-phenylethanol, DMSO; (b) B$_2$pin$_2$, Pd(dppf)Cl$_2$, KOAc, dioxane, 80° C.; (c) Pd(PPh$_3$)$_2$Cl$_2$, Na$_2$CO$_3$, EtOH, H$_2$O, 70° C.; (d) Na$_2$S$_2$O$_4$, Et$_3$N, EtOH, 80° C.; (e) TsOH.H$_2$O, NaNO$_2$, KI, MeCN, H$_2$O; (f) methyl (S)-3-methyl-1-oxo-1-{(S)-2-[5-(buta-1,3-diynyl)-1H-imidazol-2-yl]pyrrolidin-1-yl}butan-2-ylcarbamate (67), Pd(PPh$_3$)$_4$, CuI, DMF, Et$_3$N, 45° C.

Methyl ((S)-1-{(S)-2-[5-(4-iodo-3-phenoxy-phenyl)-1H-imidazol-2-yl]-pyrrolidine-1-carbonyl}-2-methyl-propyl)-carbamate (3(26)) was also obtained starting from 4-bromo-2-fluoro-1-nitro-benzene (105) in Scheme 13.

Scheme 13

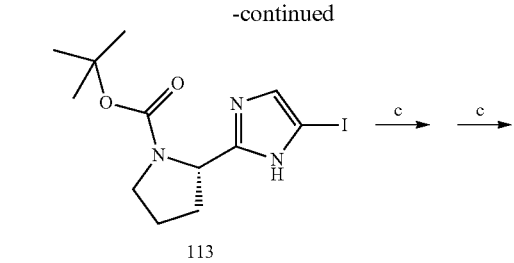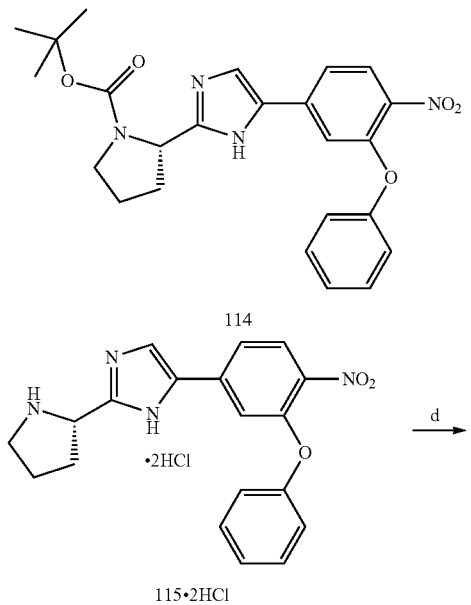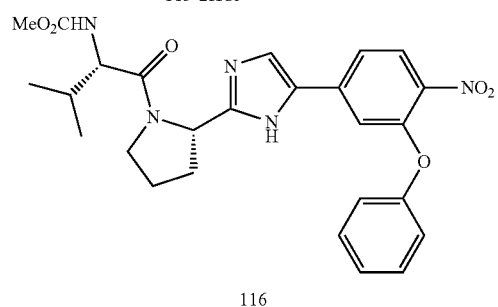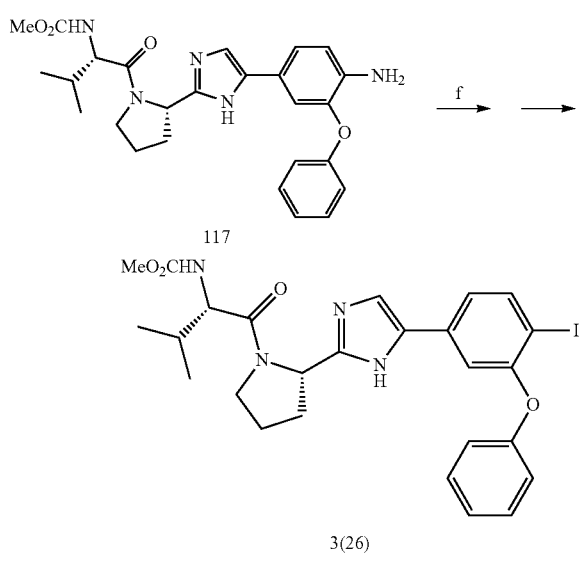

Reagents and conditions: (a) PhOH, K$_2$CO$_3$, DMF, 75° C., 3 h; (b) B$_2$Pin$_2$, Pd(PPh$_3$)$_4$, KOAc, dioxane, 90° C., 15 h; (c) Pd(PPh$_3$)$_4$, Na$_2$CO$_3$, dioxane-H$_2$O, 90° C., 15 h, (d) 2M HCl in dioxane, 2 h, rt, then Moc-L-valine, DIPEA, TBTU, MeCN, (e) H$_2$, 10% Pd(C), MeOH, 4 h, rt, (f) p-TsOH, MeCN, 10° C., then NaNO$_2$, KI, H$_2$O, 3 h, rt.

5-(4-Iodo-3-phenylsulfanyl-phenyl)-2-(S)-pyrrolidin-2-yl-1H-imidazoles (3(27)-3(29)) were obtained by starting from 1-(4-aminophenyl)ethanone (118) according to Scheme 14.

Scheme 14

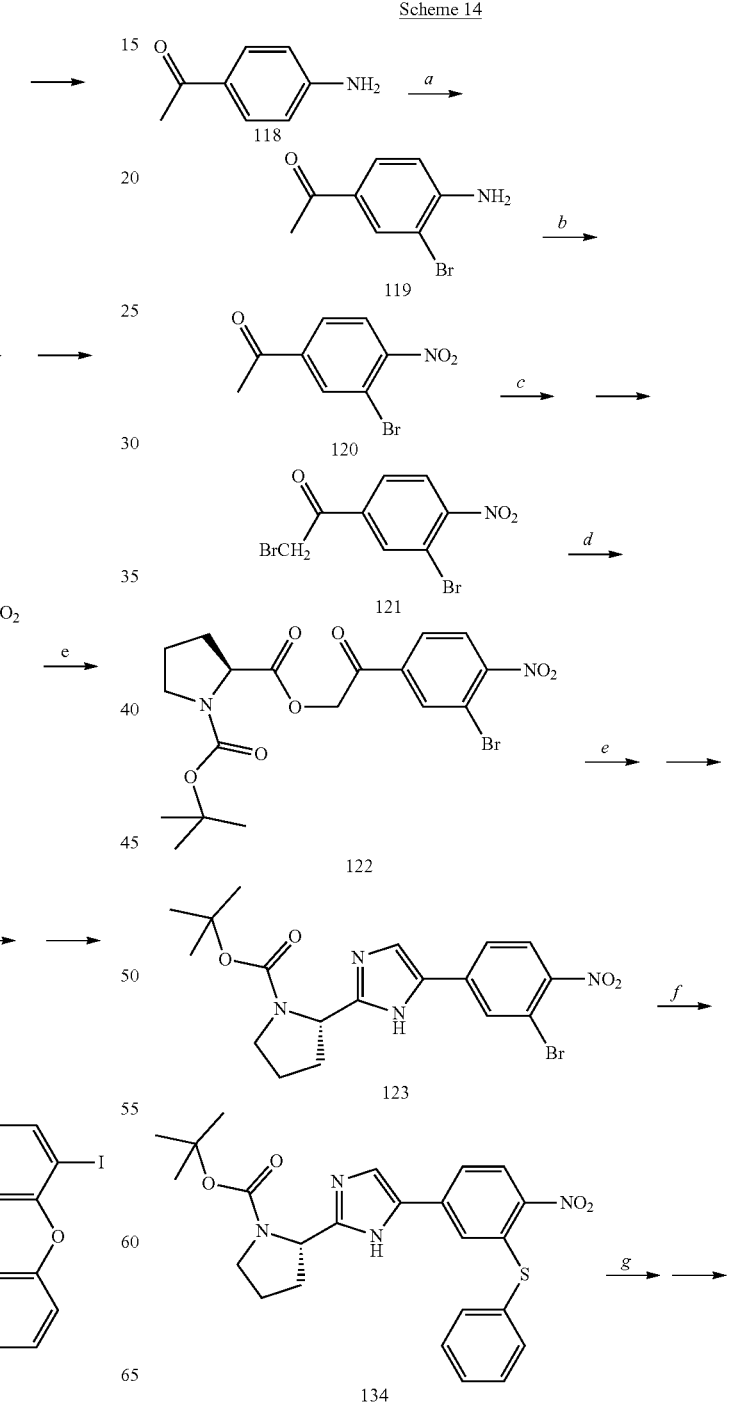

Scheme 15

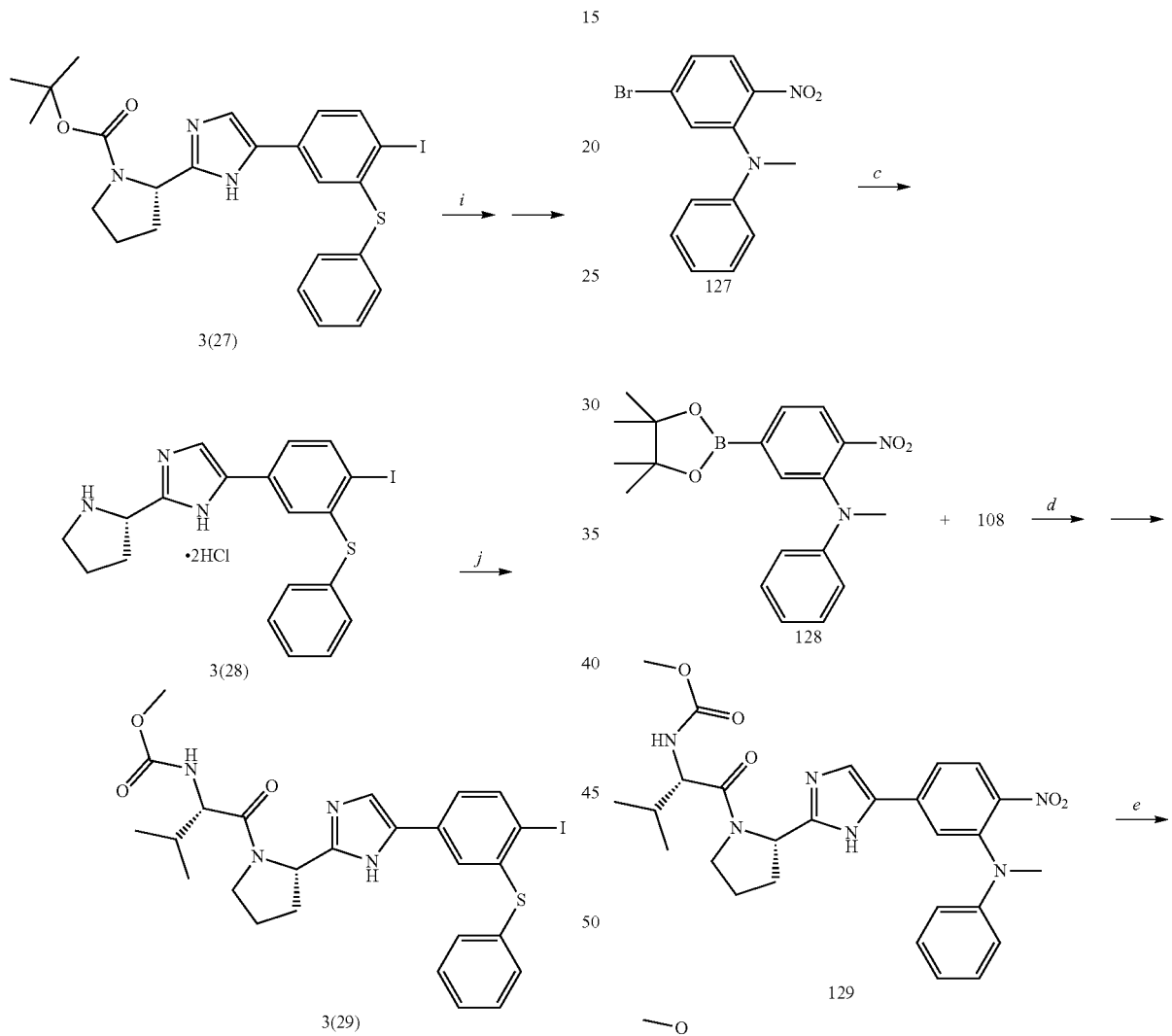

Reagents and conditions: (a) NBS, NH₄OAc, MeCN, RT, 10 min; (b) m-CPBA, toluene, reflux, 6 h; (c) Br₂, dioxane, 10° C. to RT, 1 h; (d) Boc-L-proline, DIPEA, MeCN, 15 h, RT; (e) NH₄OAc, PhMe, 110° C., 48 h; (f) PhSH, EtOH, 60° C., 48 h; (g) SnCl₂×2H₂O, EtOH, RT, ON; (h) p-TsOH, MeCN, then NaNO₂, KI, H₂O, 2 h, RT; (i) 4M HCl in dioxane, 2 h, RT; (j) Moc-L-valine, DIPEA, TBTU, DMF, 3 h, rt.

Methyl [(S)-1-((S)-2-{5-[4-iodo-3-(methyl-phenyl-amino)-phenyl]-1H-imidazol-2-yl}-pyrrolidine-1-carbonyl)-2-methyl-propyl]-carbamate (3(30)) were obtained by starting from 4-bromo-2-fluoro-1-nitro-benzene (105) in Scheme 15.

-continued

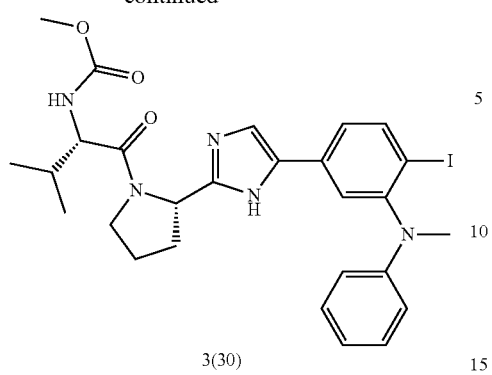

3(30)

Reagents and conditions: (a) PhNH$_2$, K$_2$CO$_3$, NMP, 50° C., 48 h; (b) CH$_3$I, DMF, 0° C., 2 h; (c), B$_2$Pin$_2$, KOAc, Pd(dppf)Cl$_2$, 80° C., 20 h; (d) Na$_2$CO$_3$, Pd(PPh$_3$)$_4$, dioxane-H$_2$O, 90° C., 20 h; (e) H$_2$, Pd/C, MeOH, 3 h, RT; (f) p-TsOH, MeCN, KI, H$_2$O, then NaNO$_2$, H$_2$O, 20 h, RT.

tert-Butyl (S)-2-(5-{6-[(4-trimethylsilyl)buta-1,3-diynyl]biphenyl-3-yl}-1H-imidazol-2-yl)pyrrolidine-1-carboxylates (3(31)-3(34)) were obtained by starting from 1,4-bis(trimethylsilyl)buta-1,3-diyne (131) using intermediates 3(1), 3(3), 3(5), and 3(6) in Scheme 16.

Scheme 16

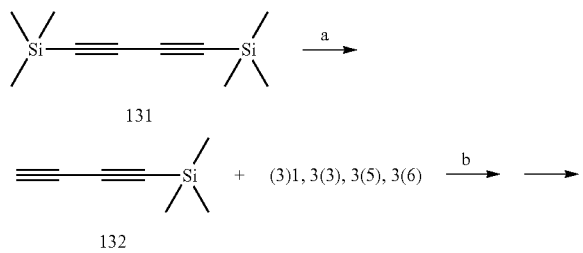

-continued

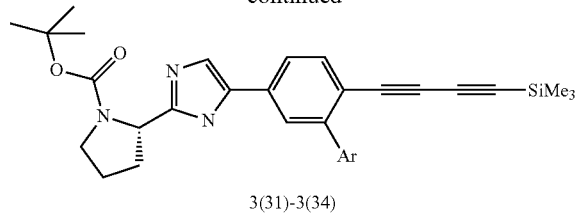

3(31)-3(34)

where Ar=Ph (3(1), 3(31)), 3-tert-Bu-Ph (3(3), 3(32)), 3-Ph-Ph (3(5), 3(33)), 2-naphthyl (3(6), 3(34)). Reagents and conditions: (a) ether, argon, MeLi.LiBr, r.t., 15 h; (b) Pd(PPh$_3$)$_4$, CuI, THF, Et$_3$N, 45° C.

tert-Butyl (S)-2-(5-[6-(buta-1,3-diynyl)biphenyl-3-yl]1H-imidazol-2-yl)pyrrolidine-1-carboxylates (3(35)-3(38)) were obtained by removing the protection of the trimethyl silyl intermediates 3(31)-3(34) (Scheme 17).

Scheme 17

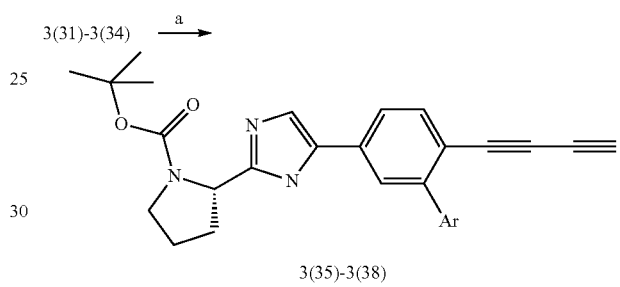

3(35)-3(38)

where Ar=Ph (3(31), 3(35)), 3-tert-Bu-Ph (3(32), 3(36)), 3-Ph-Ph (3(33), 3(37)), 2-naphthyl (3(34), 3(38)). Reagents and conditions: (a) K$_2$CO$_3$, THF, MeOH.

(S)-2-{5-[(4-{2-[(S)-Pyrrolidin-2-yl]-1H-imidazol-5-yl}-(2-arylphenyl)buta-1,3-diynyl]-1H-imidazol-2-yl}pyrrolidine tetrahydrochlorides (4(1).4HCl))-4(4).4HCl) were obtained by reacting compounds 3(35)-3(38) and 113 with subsequent removal of Boc protecting groups from reaction products 133-136 (Scheme 18).

Scheme 18

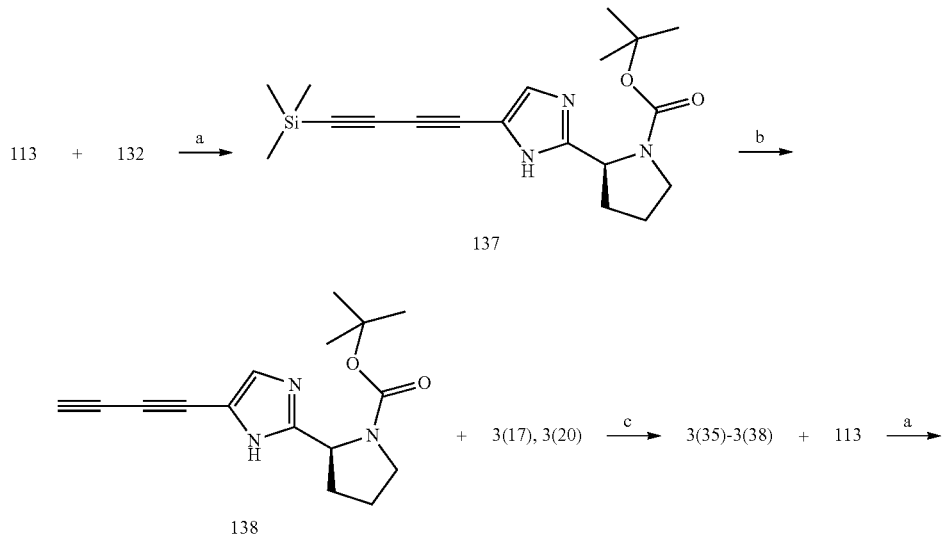

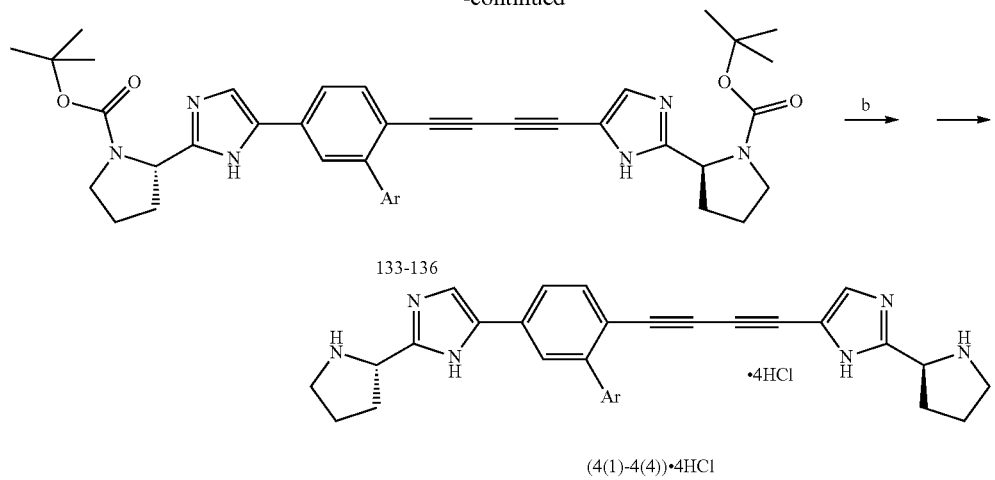

Ar=Ph (3(35), 133, 4(1).4HCl), 3-tert-Bu-Ph (3(36), 134, 4(2).4HCl), 3-Ph-Ph (3(37), 135, 4(3).4HCl), 2-naphthyl (3(38), 136, 4(4).4HCl). Reagents and conditions: (a) Pd(PPh$_3$)$_4$, CuI, THF, Et$_3$N, 40° C.; (b) HCl, dioxane.

(S)-2-(5-{5-Fluoro- (4(5).4HCl) and (S)-2-(5-{5-methyl-6-[4-((S)-2-pyrrolidin-2-yl-3H-imidazol-4-yl)-buta-1,3-diynyl]-biphenyl-3-yl}-1H-imidazol-2-yl)-pyrrolidine tetra-hydrochlorides (4(6).4HCl) were obtained by reacting diacetylene 138 and intermediates 3 (17), 3 (20) followed by removing Boc protecting groups from the reaction products 139, 140 (Scheme 19).

Scheme 19

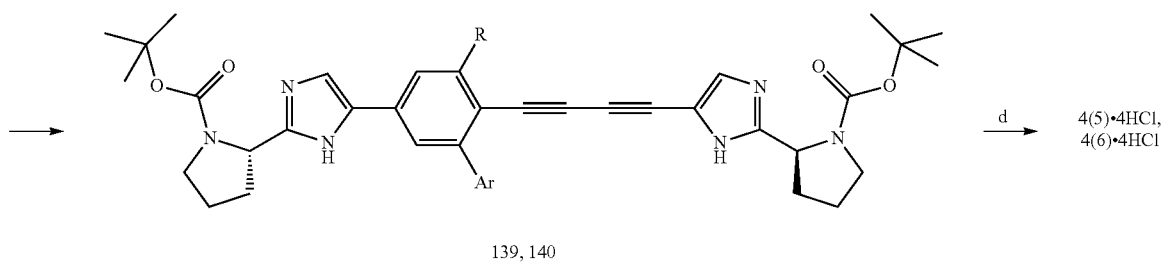

where R=F (139, 4(5)), Me (140, 4(6)). Reagents and conditions: (a) Pd(PPh$_3$)$_4$, CuI, THF, Et$_3$N, 45° C.; (b) K$_2$CO$_3$, THF, MeOH; (c) Pd(PPh$_3$)$_4$, CuI, THF, Et$_3$N, 40° C.; (d) HCl, dioxane.

The synthesis of methyl {(S)-1-[(S)-2-(5-{3-aryl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-2-methyl-propyl}-carbamate hydrochlorides (4(7).nHCl-4(18).nHCl) was carried out according to Scheme 20 by reacting diacetylene 138 with iodides 3(7)-3(16), 3(23), 3(24) followed by removing Boc protecting groups from reaction products 141-152.

Scheme 20

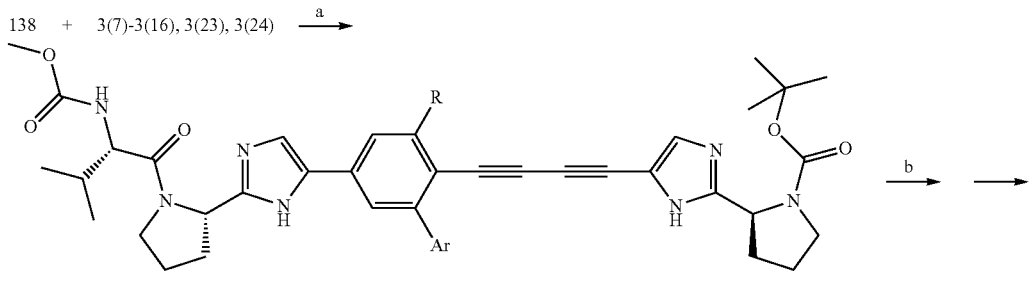

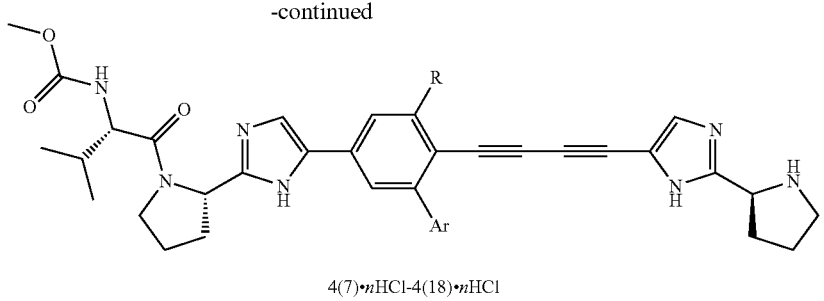

4(7)·nHCl-4(18)·nHCl where Ar=Ph (3(7), 3(23), 3(24), 139, 151, 152, 4(7).3HCl, 4(17).3HCl, 4(18).3HCl), 2-Me-Ph (3(9), 140, 4(8).3HCl), 2-F-Ph (3(8), 141, 4(9).3HCl), 3-t-Bu-Ph (3(10), 142, 4(10).3HCl), 4-t-Bu-Ph (3(11), 143, 4(11).3HCl), 3-Ph-Ph (3(12), 144, 4(12).3HCl), 4-Ph-Ph (3(13), 145, 4(13).3HCl), 4-Me$_2$N-Ph (3(14), 146, 4(14).4HCl), 4-(4-methylpiperazin-1-yl)-Ph (3(15), 147, 4(15).5HCl), 3-Py (3(16), 148, 4(16).4HCl). R=H (141-150, (4(7)-4(16)).nHCl), F (151, 4(17).3HCl), Me (152, 4(18).3HCl). Reagents and conditions: (a) Pd(PPh$_3$)$_4$, CuI, THF, Et$_3$N, 40° C.; (b) HCl, dioxane.

Methyl {(S)-2-methyl-1-[(S)-2-(5-{4-[5-((S)-2-pyrrolidin-2-yl-3H-imidazol-4-yl)-biphenyl-2-yl]-buta-1,3-diynyl}-1H-imidazol-2-yl)-pyrrolidine-1-carbonyl]-propyl}-carbamate trihydrochloride (4(19).3HCl) was obtained according to Scheme 21, which involves the synthesis of methyl (S)-3-methyl-1-oxo-1-((S)-2-[5-(buta-1,3-diynyl)-1H-imidazol-2-yl]pyrrolidin-1-yl)butan-2-ylcarbamate (155) starting from tert-butyl (S)-2-[5-(4-trimethylsilanyl-buta-1,3-diynyl)-1H-imidazol-2-yl]-pyrrolidine-1-carboxylate (137), reacting diacetylene 155 with the iodide 3(1) followed by removing the Boc protecting groups of reaction product 156.

Scheme 21

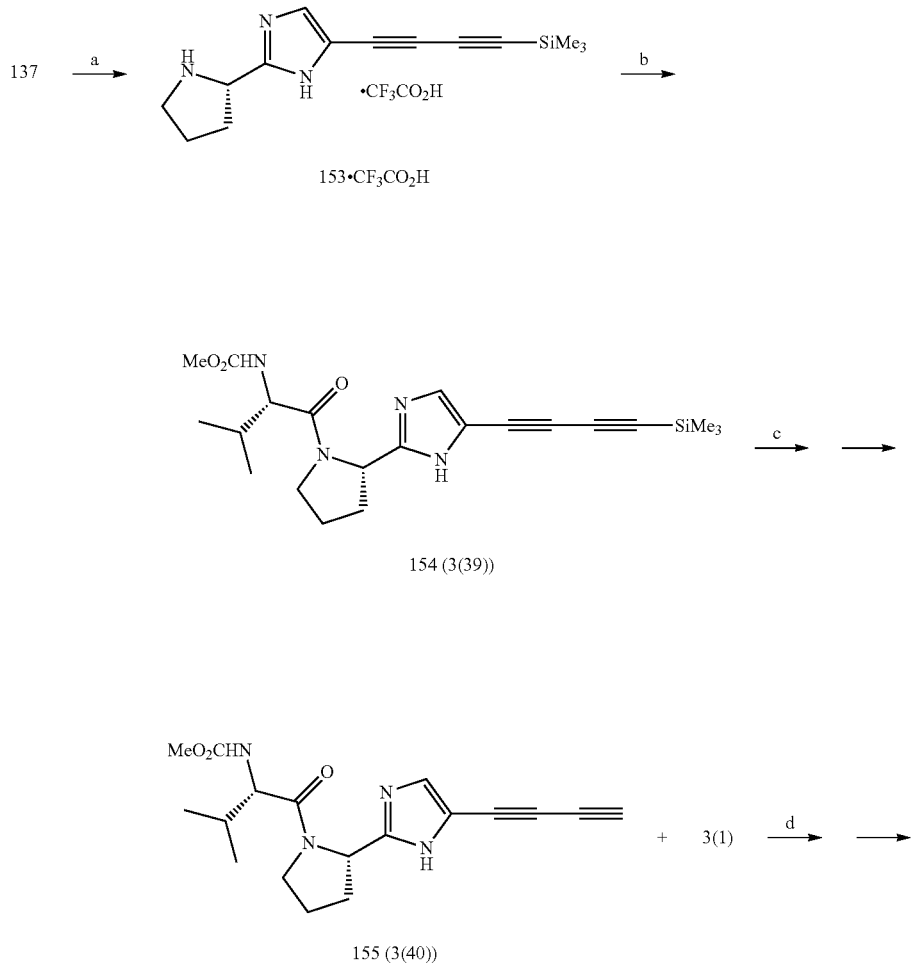

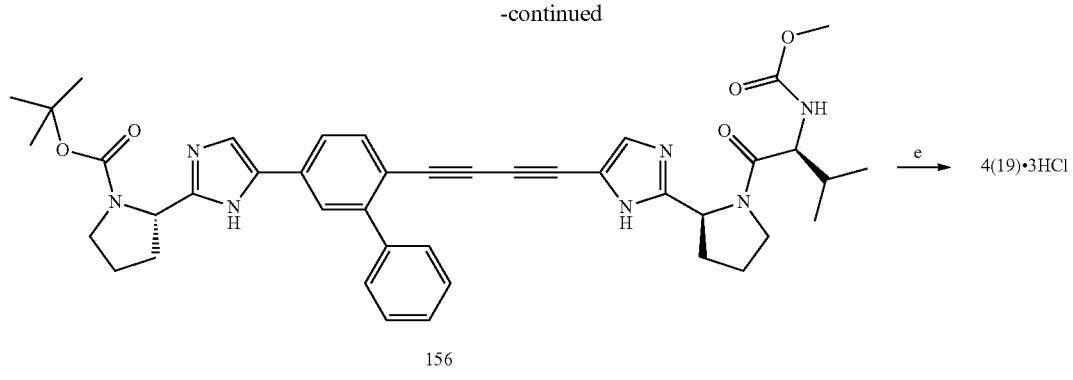

156

Reagents and conditions: (a) Pd(PPh₃)₄, CuI, THF, Et₃N, 45° C.; (b) Moc-L-valine, DIPEA, TBTU, DMF, 3 h, rt; (c) K₂CO₃, THF, MeOH; (d) Pd(PPh₃)₄, CuI, THF, Et₃N, 40° C.; (e) HCl, dioxane.

Substituted methyl {(S)-1-[(S)-2-(5-{4-[4-((S)-2-pyrrolidin-2-yl-3H-imidazol-4-yl)-buta-1,3-diynyl]-phenyl}-1H-imidazol-2-yl)-pyrrolidine-1-carbonyl]-2-methyl-propyl}-carbamate hydrochlorides ((4(20)-4(22)).nHCl) were also obtained by reacting the iodides 3(23), 3(24), 3(26), 3(29), and 3(30) with diacetylene 138 followed by removing Boc protecting groups from reaction products 157-159 (Scheme 22).

Scheme 22

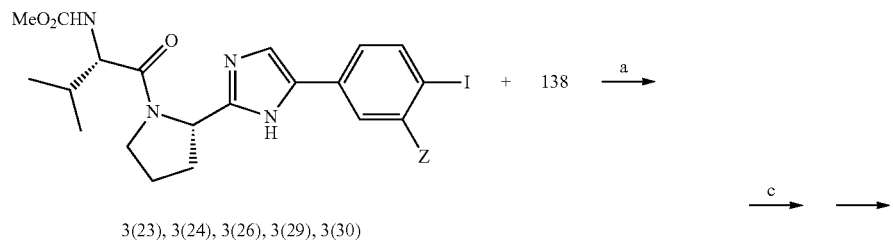

3(23), 3(24), 3(26), 3(29), 3(30)

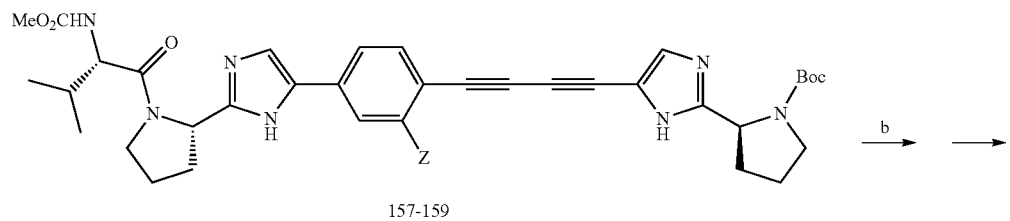

157-159

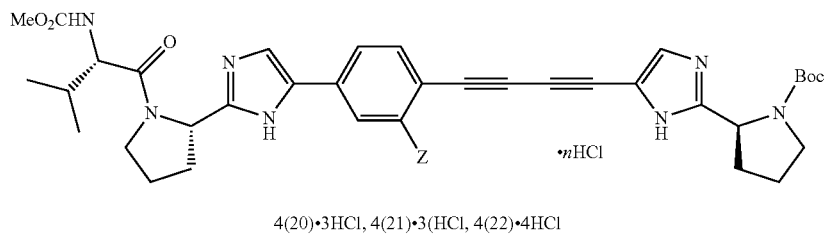

4(20)·3HCl, 4(21)·3(HCl, 4(22)·4HCl where Z=PhO (3(26), 4(20).3HCl, 157); PhS (3(29), 4(21). 3HCl, 158); PhNH (3(30), 4(22).4HCl, 159). Reagents and conditions: (a) Pd(PPh₃)₄, CuI, THF, Et₃N, 40° C.; (b) HCl, dioxane.

The synthesis of substituted methyl [(S)-2-methyl-1-((S)-2-{5-[4'-((S)-2-pyrrolidin-2-yl-3H-imidazol-4-yl)-biphenyl-4-yl]-1H-imidazol-2-yl}-pyrrolidine-1-carbonyl)-propyl]-carbamate hydrochlorides (4(23).3HCl, 4(24).3HCl, 4(25).3HCl, 4(26).4HCl) was performed (Scheme 23) using a reaction between iodides 3(7), 3(23), 3(24), 3(26), 3(29), 3(30) and tert-butyl (S)-2-{5-[4-(4,4,5,5-tetramethyl-[1,3,2]-dioxaboran-2-yl)-phenyl]-imidazol-2-yl}-pyrrolidine-1-carboxyle (162). The resulting products of this reaction were transformed by removing the Boc protective group into the target intermediates 4(23).3HCl, 4(24).3HCl, 4(25).3HCl, 4(26).4HCl.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, or indenyl.

The term "heteroaryl," as used herein, refers to a mono- or polycyclic aromatic radical having one or more ring atom selected from S, O and N; and the remaining ring atoms are carbon. Heteroaryl includes, but is not limited to, pyridinyl, pyrazinyl, pyrimidinyl, quinolinyl, isoquinolinyl, benzimidazolyl, benzooxazolyl, or quinoxalinyl.

Scheme 23

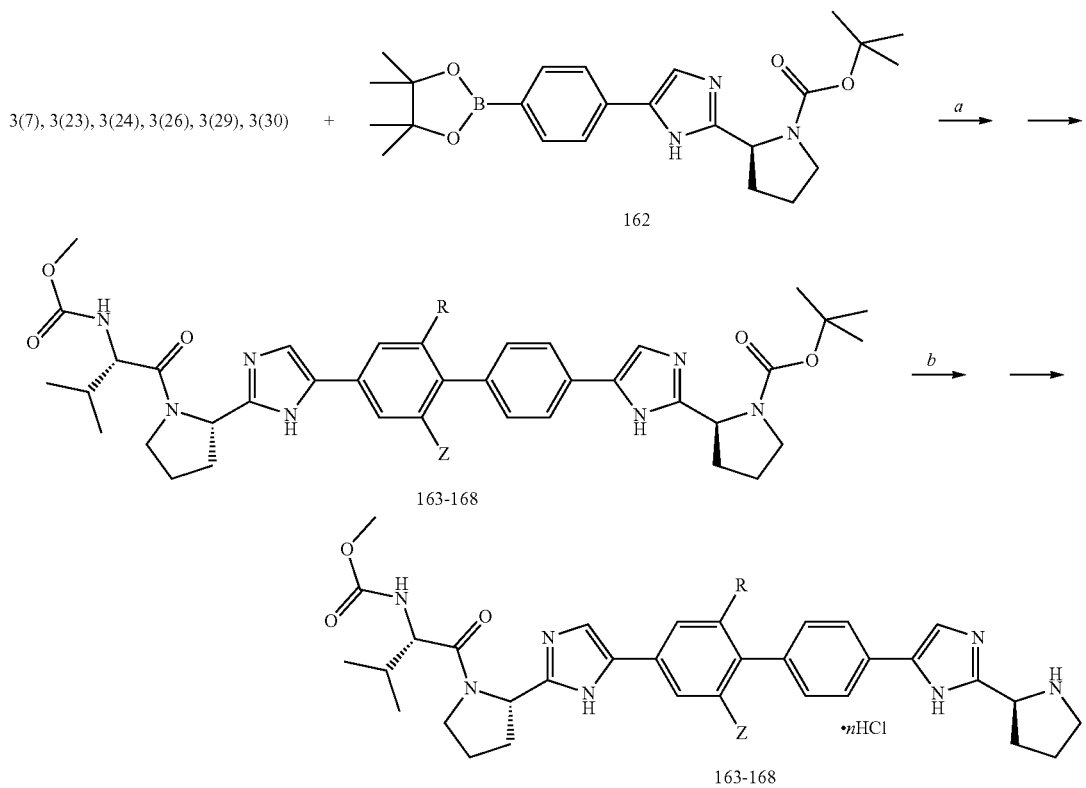

where

| Compounds numbers | R | Z |
|---|---|---|
| 3(7) → 161 → 4(23)•3HCl | H | Ph |
| 3(23) → 165 → 4(27)•3HCl | F | Ph |
| 3(24) → 166 → 4(28)•3HCl | CH₃ | Ph |
| 3(26) → 162 → 4(24)•3HCl | H | PhO |
| 3(29) → 163 → 4(25)•3HCl | H | PhS |
| 3(30) → 164 → 4(26)•4HCl | H | PhHN |

Reagents and conditions: (a) PhS (3(27), 163, 4(26).3HCl); Pd(PPh₃)₄, NaHCO₃, dioxane-H₂O, 15 h, 90° C.; (b) 2M HCl in dioxane, 2 h, r.

In accordance with the invention, any of the aryls, substituted aryls, heteroaryls and substituted heteroaryls described herein can be any aromatic group. Aromatic groups can be substituted or unsubstituted.

The term "$C_1$-$C_6$ alkyl" as used herein, refers to saturated, straight- or branched-chain hydrocarbon radicals containing from one to six carbon atoms. The examples of $C_1$-$C_6$ alkyl radicals include, but are not limited to, methyl, ethyl, propyl, isopropyl, n-butyl, and tert-butyl. "Lower alkyl" refers to an unbranched or branched alkyl chain comprising 1-4 carbon atoms.

The term "$C_1$-$C_6$ alkyloxy" as used herein, refers to alkyl-O-group where "alkyl" listed in this section. The examples of $C_1$-$C_6$ alkyloxy radicals include, but are not limited to, methoxy, ethoxy, propoxy, iso-propoxy, butoxy.

The term "$C_3$-$C_6$ cycloalkyl" as used herein, refers to carbocyclic ring system containing from 3 to six carbon atoms. The examples of $C_3$-$C_6$ cycloalkyl radicals include, but are not limited to, cyclopropyl, cyclobutyl, cyclopentyl, cyclohexyl.

The term "optionally substituted" means the group referred to can be substituted at one or more positions by any one or any combination of the radicals.

"Active component" (drug substance) refers to a physiologically active compound of synthetic or other (biotechnological, vegetable, animal, microbicidal, and so on) origins exhibiting a pharmacological activity, which is an active ingredient of the pharmaceutical composition employed in production.

"Medicament" is a compound (or a mixture of compounds as a pharmaceutical composition) and a preparation of medicaments in the form of tablets, capules, injections, ointments, and other ready forms intended for restoration, improvement, or modification of physiological functions in humans and animals and for the treatment and prophylaxis of diseases, for diagnostics, anesthesia, contraception, cosmetology, and so on.

"Therapeutic cocktail" represents a simultaneously administered combination of two or more medicaments exhibiting a different mechanism of pharmacological action and directed to various biotargets taking part in the disease process.

"Pharmaceutical composition" means a composition comprising a compound of general formula 2 and at least one component selected from a group consisting of pharmaceutically acceptable and pharmacologically compatible fillers, solvents, diluents, carriers, auxiliaries, distributors and exipients, delivery agents, such as preservatives, stabilizers, fillers, disintegrators, moisteners, emulsifiers, suspending agents, thickeners, sweeteners, flavouring agents, aromatizing agents, antibacterial agents, fungicides, lubricants, and prolonged delivery controllers, choice and suitable proportions of which depend on the nature and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant, and mixtures thereof.

Protection against microorganisms can be provided by various antibacterial and antifungal agents, such as, for example, parabens, chlorobutanole, sorbic acid, and similar compounds. Composition may also comprise isotonic agents, such as, for example, sugar, sodium chloride, and similar compounds. The prolonged effect of a composition may be achieved by agents slowing down the absorption of the active ingredient, for example, aluminum monostearate or gelatine. Examples of suitable carriers, solvents, diluents, and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. The examples of disintegrators and distributors are starch, alginic acid and its salts, and silicates.

The examples of suitable lubricants are magnesium stearate, sodium lauryl sulfate, talc, and high molecular weight polyethylene glycol. A pharmaceutical composition for peroral, sublingval, transdermal, intramuscular, intravenous, subcutaneous, and local or rectal administration of the active ingredient, alone or in combination with another active compound, may be administered to humans and animals in standard administration form, or in a mixture with traditional pharmaceutical carriers. Suitable standard administration forms include peroral forms such as tablets, gelatin capsules, pills, powders, granules, chewing gums, and peroral solutions or suspensions; sublingval and transbuccal administration forms; aerosols; implants; local, transdermal, subcutaneous, intramuscular, intravenous, intranasal or intraocular forms, and rectal administration forms.

"Pharmaceutically acceptable salt" means relatively non-toxic, both organic and inorganic, salts of acids and bases disclosed in this invention. The salts could be prepared in situ in the processes of synthesis, isolation, or purification of compounds or they could be prepared specially. Pharmaceutically acceptable salts may be prepared from inorganic or organic acids. Examples of suitable inorganic acids include, but are not limited to, hydrochloric, hydrobromic, nitric, carbonic, sulfuric, and phosphoric acids. The examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, algenic acid, hydroxybutyric acid, galactarate, galacturonate, adipate, alginate, bisulfate, butyrate, camphorate, camphorsulfonate, cyclopentanepropionate, dodecyl sulfate, glycoheptanoate, glycerophosphate, hemisulfate, heptanoate, hexanoate, nicotinate, 2-naphthalesulfonate, 1,5-naphthalendisulfonate, oxalate, palmoate, pectinate, persulfate, 3-phenylpropionate, picrate, pivalate, thiocyanate, tosylate, and undecanoate. The compounds or salts of the present invention may exist in the form of solvates, such as with water (i.e., hydrates), or with organic solvents (e.g., with methanol, ethanol or acetonitrile to form methanolate, ethanolate or acetonitrilate, respectively). A detailed description of the properties of such salts is given in: Berge S. M., et al. "Pharmaceutical Salts" J. Pharm. Sci., 1977, 66, 1-19.

The compounds or salts of the present invention may also be used in the form of prodrugs.

The compounds of the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free" it is meant that at least 80% of the compound in a composition is the described stereoisomer; preferably, at least 90% of the compound in a composition is the described stereoisomer; and, more preferably, at least 95%, 96%, 97%, 98%, or 99% of the compound in a composition is the described stereoisomer. Where the stereochemistry of a chiral carbon is not specified in the chemical structure of a compound, the chemical structure is intended to encompass compounds containing either stereoisomer of the chiral center. Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographic separation of the diastereomers and regeneration of the individual enantiomers, and enzymatic resolution.

Stereospecific synthesis typically involves the use of appropriate optically pure (enantiomerically pure) or substantially optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in a solution and loaded onto the column containing a chiral stationary phase. Enantiomers can then be separated by HPLC. The resolution of enantiomers can also be improved by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or a covalent bond with the chiral auxiliary. Non-limiting examples of suitable chiral auxiliaries include chirally pure amino acids, organic carboxylic acids, or organosulfonic acids. Once the diastereomers are separated by chromatography, individual enantiomers can be regenerated. Frequently, the chiral auxiliary can be recovered and used again.

Enzymes such as esterases, phosphatases, or lipases can be useful for the resolution of derivatives of enantiomers in an enantiomeric mixture. For example, an ester derivative of a carboxyl group in the compounds to be separated can be treated with an enzyme, which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treating the carboxylic acid with a suitable optically pure base, such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

In addition, where a compound exists in various tautomeric forms, a recited compound is not limited to any one specific tautomer, but rather is intended to encompass all tautomeric forms. The compounds of the invention may exist in different stable conformational forms, which may be separable. Torsional asymmetry due to restricted rotations about an asymmetric single bond, for example, because of steric hindrance or ring strain, may permit separation of different conformers. The invention encompasses each conformational isomer of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms.

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. If a linking element in a depicted structure is a bond, then the element left to the linking element is joined directly to the element right to the linking element via a covalent bond. If two or more adjacent linking elements in a depicted structure are bonds, then the element left to these linking elements is joined directly to the element right to these linking elements via a covalent bond.

When a chemical formula is used to describe a moiety, the dash(es) indicates the portion of the moiety that has the free valence(s). If a moiety is described as being "optionally substituted", the moiety may be either substituted or unsubstituted. If a moiety is described as being optionally substituted with up to a particular number of non-hydrogen radicals, said moiety may be either unsubstituted, or substituted by up to that particular number of non-hydrogen radicals, or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions.

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g., a reduction in viral load.

The term "prodrug" refers to derivatives of the compounds of the invention which have chemically or metabolically cleavable groups and become, by solvolysis or under physiological conditions, the compounds of the invention, which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., Desing of products, pp. 7-9, 21-24, Elsevier, Amsterdam 1985). Prodrugs include acid derivatives well known to practitioners in the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to a physical association of a compound of this invention with one or more solvent molecules, whether organic or inorganic. This physical association often includes hydrogen bonding. In certain instances, the solvate will be capable of isolation, for example, when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "N-protecting group" or "N-protected" refers to those groups capable of protecting an amino group against undesirable reactions. Commonly used N-protecting groups are described in Greene and Wuts, Protecting groups in chemical synthesis ($3^{rd}$ ed., John Wiley & Sons, NY (1999)). Non-limiting examples of N-protecting groups include acyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The present disclosure will now be described in connection with certain embodiments, which are not intended to limit its scope. On the contrary, the present disclosure covers all alternatives, modifications, and equivalents as can be included within the scope of the claims. Thus, the following examples, which include specific 10 embodiments, will illustrate one practice of the present disclosure, it being understood that the examples are for the purposes of illustration of certain embodiments and are presented to provide what is believed to be the most useful and readily understood description of its procedures and conceptual aspects.

EXAMPLES

Example 1 (Scheme 7)

Synthesis of tert-butyl (S)-2-[5-(3-aryl-4-iodo-phenyl)-1H-imidazol-2-yl]-pyrrolidine-1-carboxylate (3(1)-3(6))

A mixture of N-(4-acetyl-2-bromophenyl)acetamide (10) (2.56 g, 10 mmol), phenylboronic acid (11) (1.463 g, 12 mmol), $Na_2CO_3$ (3.18 g, 30 mmol) and bis(triphenylphosphine)palladium(II) dichloride (0.35 g, 0.5 mmol) in 25 mL of ethanol and 5 mL of water was stirred under Ar at 80° C. for 15 h. After the reaction was completed (LC-MS check), the cooled mixture was rotovapped from ethanol, diluted with water and extracted with DCM. Column chromatography on silica gel (hexane:EtOAc 3:2) afforded the product.

The yield of N-(5-acetylbiphenyl-2-yl)acetamide (17) is 2.28 g (90%). $^1$H NMR (DMSO-$d_6$, 400 MHz) δ 9.34 (s, 1H), 7.93 (dd, $J_1$=8.4 Hz, $J_2$=2.0 Hz, 1H), 7.83 (d, J=2.0 Hz, 1H), 7.79 (d, J=8.4 Hz, 1H), 7.49 (m, 2H), 7.43 (m, 3H), 2.59 (s, 3H), 1.94 (s, 3H). Similarly, N-(5-acetyl-4'-methylbiphenyl-2-yl)-acetamide (18), LC-MS (ESI) 268 (M+H)$^+$; N-(5-acetyl-3'-tert-butyl-biphenyl-2-yl)-acetamide (19), LC-MS (ESI) 310 (M+H)$^+$; N-(5-acetyl-4'-fluoro-biphenyl-2-yl)-acetamide (20), LC-MS (ESI) 272 (M+H)$^+$; N-(5-acetyl-[1,1';3',1"]terphenyl-2-yl)-acetamide (21), LC-MS (ESI) 330 (M+H)$^+$; and N-[4-acetyl-2-(naphthalen-2-yl)phenyl]acetamide (22), $^1$H NMR (DMSO-$d_6$, 400 MHz) δ 9.40 (s, 1H), 7.99 (m, 6H), 7.88 (d, J=9.6 Hz, 1H), 7.56 (m, 3H), 2.61 (s, 3H), 1.94 (s, 3H) were synthesized.

A mixture of 17 (2.28 g, 9 mmol) and 45 mL of hydrochloric acid was refluxed for 5 h, then cooled down and rotovapped. The residue was treated with 10 mL of water and 0.783 mL (9 mmol) of hydrochloric acid, cooled to −5-0° C., and diazotated with 652 mg (9.45 mmol) of $NaNO_2$ in 4 mL of water. After stirring for 0.5 h at −5-0° C., 35 mL of 10% KI solution was added, and the stirring continued for 1 h at 0° C. and 1 h at rt. The mixture was diluted with a 5% $NaHCO_3$ solution, clarified with $Na_2S_2O_3$, and extracted with benzene. After drying and rotovapping, the residue was subjected to column chromatography on silica gel (hexane:$CHCl_3$ 1:2) to afford 1.48 g (51%) of iodide 1-(6-iodobiphenyl-3-yl)ethanone (23). $^1$H NMR (DMSO-$d_6$, 400 MHz) δ 8.16 (d, J=8.4 Hz, 1H), 7.80 (d, J=2.0 Hz, 1H), 7.64 (dd, $J_1$=8.4 Hz, $J_2$=2.0 Hz, 1H), 7.49 (m, 2H), 7.44 (m, 1H), 7.37 (m, 2H), 2.58 (s, 3H). Similarly, 1-(4'-methyl-6-iodo-biphenyl-3-yl)-ethanone (24), LC-MS (ESI) 337 (M+H)$^+$; 1-(3'-tert-butyl-6-iodo-biphenyl-3-yl)-ethanone (25), LC-MS (ESI) 379 (M+H)$^+$; 1-(4'-fluoro-6-iodo-biphenyl-3-yl)-ethanone (26), LC-MS (ESI) 341 (M+H)$^+$; 1-(6-iodo-[1,1';3',1"]terphenyl-3-yl)-ethanone (27), LC-MS (ESI) 399 (M+H)$^+$; and 1-[4-iodo-3-(naphthalen-2-yl)phenyl]ethanone (28), $^1$H NMR (DMSO-$d_6$, 400 MHz) δ 8.20 (d, J=8.4 Hz, 1H), 8.01 (m, 3H), 7.92 (m, 2H), 7.69 (dd, $J_1$=8.4 Hz, $J_2$=2.0 Hz, 1H), 7.59 (m, 2H), 7.44 (dd, $J_1$=8.4 Hz, $J_2$=1.6 Hz, 1H), 2.61 (s, 3H) were synthesized.

To a stirred solution of 23 (0.805 g, 2.5 mmol) in 10 mL of AcOH, 0.1 mL of 33% HBr in AcOH was added and then, dropwise, a solution of 0.135 mL (2.625 mmol) of $Br_2$ in 3 mL of AcOH at 10-15° C. After 2 h of stirring, the mixture was rotovapped and the residue was recrystallized from isopropanol to afford 0.772 g (77%) of 2-bromo-1-(6-iodo-biphenyl-3-yl)ethanone (29). $^1$H NMR ($CDCl_3$, 400 MHz) δ 8.13 (d, J=8.4 Hz, 1H), 7.88 (d, J=2.0 Hz, 1H), 7.63 (dd, $J_1$=8.4 Hz, $J_2$=2.0 Hz, 1H), 7.47 (m, 3H), 7.36 (m, 2H), 4.42 (s, 2H). Similarly, 2-bromo-1-(4'-methyl-6-iodo-biphenyl-3-yl)-ethanone (30), LC-MS (ESI) 416 (M+H)$^+$; 2-bromo-1-(3'-tert-butyl-6-iodo-biphenyl-3-yl)-ethanone (31), LC-MS (ESI) 458 (M+H)$^+$; 2-bromo-1-(4'-fluoro-6-iodo-biphenyl-3-yl)-ethanone (32), LC-MS (ESI) 420 (M+H)$^+$; 2-bromo-1-(6-iodo-[1,1';3',1"]terphenyl-3-yl)-ethanone (33), LC-MS (ESI) 478 (M+H)$^+$; and 2-bromo-1-[4-iodo-3-(naphthalen-2-yl)phenyl]ethanone (34), $^1$H NMR ($CDCl_3$, 400 MHz) δ 8.17 (d, J=8.4 Hz, 1H), 7.98 (d, J=2.0 Hz, 1H), 7.93 (m, 3H), 7.83 (s, 1H), 7.67 (dd, J, =8.4 Hz, $J_2$=2.4 Hz, 1H), 7.57 (m, 2H), 7.50 (dd, $J_1$=8.4 Hz, $J_2$=2.0 Hz, 1H), 4.44 (s, 2H) were synthesized.

To a mixture of 2-bromo-1-(6-iodobiphenyl-3-yl)ethanone (29) (0.772 g, 1.92 mmol) and Boc-L-proline (0.435 g, 2.02 mmol) in 20 mL of MeCN, DIPEA (0.352 mL, 2.02 mmol) was added, and the mixture was stirred at rt for 4 h, then rotovapped, dissolved in DCM, washed with water, dried over Na$_2$SO$_4$, rotovapped, and subjected to column chromatography on silica gel (hexane:EtOAc from 7:1 to 4:1) to give 0.938 g (91%) of tert-butyl (S)-2-[2-(6-iodobiphenyl-3-yl)-2-oxoethyl] pyrrolidine-1,2-dicarboxylate (35). $^1$H NMR (CDCl$_3$, 400 MHz) δ 8.12 (dd, J$_1$=8.0 Hz, J$_2$=4.0 Hz, 1H), 7.79 (d, J=2.4 Hz, 1H), 7.54 (td, J$_1$=8.0 Hz, J$_2$=2.4 Hz, 1H), 7.46 (m, 3H), 7.34 (m, 2H), 5.34 (m, 2H), 4.45 (m, 1H), 3.58 (m, 1H), 3.44 (m, 1H), 2.32 (m, 2H), 2.07 (m, 1H), 1.94 (m, 1H), 1.44, 1.47 (2 s, 9H). Similarly, tert-butyl (S)-2-[2-(4'-methyl-6-iodo-biphenyl-3-yl)-2-oxoethyl]pyrrolidine-1,2-dicarboxylate (36), LC-MS (ESI) 550 (M+H)$^+$; tert-butyl (S)-2-[2-(3'-tert-butyl-6-iodo-biphenyl-3-yl)-2-oxo-ethyl]pyrrolidine-1,2-dicarboxylate (37), LC-MS (ESI) 592 (M+H)$^+$; tert-butyl (S)-2-[2-(4'-fluoro-6-iodo-biphenyl-3-yl)-2-oxo-ethyl]pyrrolidine-1,2-dicarboxylate (38), LC-MS (ESI) 554 (M+H)$^+$; (S)-1-tert-butyl 2-[2-(6-iodo-[1,1',3',1"]terphenyl-3-yl)-2-oxo-ethyl]pyrrolidine-1,2-dicarboxylate (39), LC-MS (ESI) 612 (M+H)$^+$; and tert-butyl (S)-2-{2-[4-iodo-3-(naphthalen-2-yl)phenyl]-2-oxoethyl}pyrrolidine-1,2-dicarboxylate (40), $^1$H NMR (CDCl$_3$, 400 MHz) δ 8.16 (dd, J$_1$=8.0 Hz, J$_2$=4.0 Hz, 1H), 7.93 (m, 3H), 7.89 (d, J=2.0 Hz, 1H), 7.81 (s, 1H), 7.58 (m, 3H), 7.48 (d, J=8.0 Hz, 1H), 5.36 (m, 2H), 4.46 (m, 1H), 3.59 (m, 1H), 3.45 (m, 1H), 2.33 (m, 2H), 2.07 (m, 1H), 1.94 (m, 1H), 1.44, 1.48 (2 s, 9H) were synthesized.

A mixture of ester 27 (0.938 g, 1.75 mmol) and ammonium acetate (0.675 g, 8.76 mmol) in 10 mL of toluene was stirred at 100° C. for 15 h. The cooled mixture was diluted with water, extracted with toluene, dried over Na$_2$SO$_4$, rotovapped, and subjected to column chromatography on silica gel (CHCl$_3$:Me$_2$CO 19:1) to afford 0.685 g (76%) of (S)-2-[5-(6-iodo-biphenyl-3-yl)-1H-imidazol-2-yl]-pyrrolidine-1-carboxylic acid tert-butyl ester (3(1)), LC-MS (ESI) 516 (M+H)$^+$. $^1$H NMR (DMSO-d$_6$, 400 MHz) δ 12.00 (m, 1H), 7.89 (d, J=8.4 Hz, 1H), 7.68 (s, 1H), 7.60 (brs, 1H), 7.45 (m, 4H), 7.34 (m, 2H), 4.77 (m, 1H), 3.51 (brs, 1H), 3.34 (m, 1H), 2.17 (m, 1H), 1.89 (m, 3H), 1.15, 1.39 (2 s, 9H). Similarly, (S)-2-[5-(6-iodo-4'-methyl-biphenyl-3-yl)-1H-imidazol-2-yl]-pyrrolidine-1-carboxylic acid tert-butyl ester (3(2)), LC-MS (ESI) 529 (M+H)$^+$, (S)-2-[5-(3'-tert-butyl-6-iodo-biphenyl-3-yl)-1H-imidazol-2-yl]-pyrrolidine-1-carboxylic acid tert-butyl ester (3(3)), LC-MS (ESI) 572 (M+H)$^+$, (S)-2-[5-(4'-fluoro-6-iodo-biphenyl-3-yl)-1H-imidazol-2-yl]-pyrrolidine-1-carboxylic acid tert-butyl ester (3(4)), LC-MS (ESI) 534 (M+H)$^+$, (S)-2-[5-(6-iodo-[1,1';3',1"]terphenyl-3-yl)-1H-imidazol-2-yl]-pyrrolidine-1-carboxylic acid tert-butyl ester (3(5)), LC-MS (ESI) 592 (M+H)$^+$; and (S)-2-[5-(4-iodo-3-naphthalen-2-yl-phenyl)-1H-imidazol-2-yl]-pyrrolidine-1-carboxylic acid tert-butyl ester (3(6)), LC-MS (ESI) 566 (M+H)$^+$, $^1$H NMR (DMSO-d$_6$, 400 MHz) δ 12.01 (m, 1H), 7.99 (m, 3H), 7.93 (d, J=8.4 Hz, 1H), 7.89 (s, 1H), 7.80 (d, J=1.6 Hz, 1H), 7.56 (m, 5H), 4.77 (m, 1H), 3.51 (m, 1H), 3.34 (m, 1H), 2.18 (m, 1H), 1.89 (m, 3H), 1.16, 1.39 (2 s, 9H) were synthesized.

Example 2 (Scheme 8)

Synthesis of methyl ((S)-1-{(S)-2-[5-(3-aryl-4-iodophenyl)-1H-imidazol-2-yl]-pyrrolidine-1-carbonyl}-2-methyl-propyl)-carbamates 3(7)-3(16)

The procedure given above for compounds 35-40 (Example 1) and in the paper by S. Pasaribu and L. Williams [*Austr. J. Chem.* (1975), 28(5), 1023-1030] was applied for the synthesis of (S)-2-[2-(3-bromo-4-nitrophenyl)-2-oxoethyl] 1-tert-butyl pyrrolidine-1,2-dicarboxylate (42). $^1$H NMR (CDCl$_3$, 400 MHz) δ 8.26 (s, 1H), 7.97 (m, 1H), 7.92 (m, 1H), 5.34 (m, 2H), 4.45 (m, 1H), 3.52 (m, 2H), 2.30 (m, 2H), 2.05 (m, 1H), 1.96 (m, 1H), 1.46, 1.47 (2 s, 9H).

The procedure given above for compounds 3(1)-3(6) (Example 1) was used for the synthesis of (S)-tert-butyl 2-[5-(3-bromo-4-nitrophenyl)-1H-imidazol-2-yl]pyrrolidine-1-carboxylate (43). LC-MS (ESI) 438 (M+H)$^+$. $^1$H NMR (DMSO-d$_6$, 400 MHz) δ 12.25 (m, 1H), 8.21 (s, 1H), 8.03 (d, J=8.4 Hz, 1H), 7.93 (d, J=8.4 Hz, 1H), 7.88 (m, 1H), 4.80 (m, 1H), 3.54 (m, 1H), 3.37 (m, 1H), 2.24 (m, 1H), 1.92 (m, 3H), 1.14, 1.40 (2 s, 9H).

To a solution of 43 0.24 mmol in 3.5 mL of dioxane, 3.5 mL of 4 M HCl solution in dioxane was added, and the mixture was stirred for 15 h, then rotovapped to obtain of (S)-5-(3-bromo-4-nitrophenyl)-2-(pyrrolidin-2-yl)-1H-imidazole dihydrochloride (44). LC-MS (ESI) 473 (M+H)$^+$.LC-MS (ESI) 337, 339 (M+H)$^+$. $^1$H NMR (DMSO-d$_6$, 400 MHz) δ 10.37 (s, 1H), 9.47 (d, J=1.2 Hz, 1H), 8.19 (s, 1H), 8.11 (d, J=8.4 Hz, 1H), 8.06 (dd, J$_1$=8.4 Hz, J$_2$=1.2 Hz, 1H), 4.88 (s, 1H), 3.37 (m, 2H), 2.42 (m, 1H), 2.32 (m, 1H), 2.15 (m, 1H), 2.01 (m, 1H).

To a solution of compound 44 (0.24 mmol) in 5 mL of DMF, N-Moc-L-valine (91 mg, 0.52 mmol), HATU (225 mg, 0.59 mmol), and DIPEA (0.412 mL, 2.36 mmol) were added, and the mixture was stirred in a fridge for 4 h. The mixture was then diluted with DCM, washed with a 5% citric acid solution, dried over Na$_2$SO$_4$, rotovapped, and subjected to HPLC to afford methyl (S)-1-{(S)-2-[5-(3-bromo-4-nitrophenyl)-1H-imidazol-2-yl]pyrrolidin-1-yl}-3-methyl-1-oxobutan-2-ylcarbamate (45). LC-MS (ESI) 494, 496 (M+H)$^+$. $^1$H NMR (DMSO-d$_6$, 400 MHz) δ 12.55 (s, 0.02H), 12.36 (s, 0.08H), 12.14 (s, 0.9H), 8.21 (s, 0.1H), 8.18 (s, 0.8H), 8.15 (s, 0.1H), 8.08 (d, J=8.8 Hz, 0.08H), 8.02 (d, J=8.8 Hz, 0.92H), 7.87 (m, 2H), 7.23 (d, J=8.0 Hz, 0.87H), 6.84 (m, 0.13H), 5.22 (m, 0.08H), 5.06 (m, 0.92H), 4.07 (t, J=8.4 Hz, 1H), 3.80 (m, 1H), 3.53 (s, 3H), 2.13 (m, 2H), 1.96 (m, 3H), 0.85, 0.91 (2 d, J=6.8 Hz, 6H).

The synthetic procedure given above for compounds 17-22 (Example 1) was used for the synthesis of compounds 46-55: methyl (S)-1-{(S)-2-[5-(6-nitrobiphenyl-3-yl)-1H-imidazol-2-yl]pyrrolidin-1-yl}-3-methyl-1-oxobutan-2-ylcarbamate (46), LC-MS (ESI) 492 (M+H)$^+$; methyl (S)-1-{(S)-2-[5-(3'-fluoro-6-nitrobiphenyl-3-yl)-1H-imidazol-2-yl]pyrrolidin-1-yl}-3-methyl-1-oxobutan-2-ylcarbamate (47), LC-MS (ESI) 510 (M+H)$^+$; methyl (S)-1-{(S)-2-[5-(3'-methyl-6-nitrobiphenyl-3-yl)-1H-imidazol-2-yl]pyrrolidin-1-yl}-3-methyl-1-oxobutan-2-ylcarbamate (48), LC-MS (ESI) 506 (M+H)$^+$; methyl (S)-1-{(S)-2-[5-(3'-tert-butyl-6-nitrobiphenyl-3-yl)-1H-imidazol-2-yl]pyrrolidin-1-yl}-3-methyl-1-oxobutan-2-ylcarbamate (49), LC-MS (ESI) 548 (M+H)$^+$; methyl (S)-1-{(S)-2-[5-(4'-tert-butyl-6-nitrobiphenyl-3-yl)-1H-imidazol-2-yl]pyrrolidin-1-yl}-3-methyl-1-oxobutan-2-ylcarbamate (50), LC-MS (ESI) 548 (M+H)$^+$; methyl (S)-1-{(S)-2-[5-(6-nitro-1,1':3',1"-terphenyl-3-yl)-1H-imidazol-2-yl]pyrrolidin-1-yl}-3-methyl-1-oxobutan-2-ylcarbamate (51), LC-MS (ESI) 568 (M+H)$^+$; methyl (S)-1-{(S)-2-[5-(6-nitro-1,1'4',1"-terphenyl-3-yl)-1H-imidazol-2-yl]pyrrolidin-1-yl}-3-methyl-1-oxobutan-2-ylcarbamate (52), LC-MS (ESI) 568 (M+H)$^+$; methyl (S)-1-((S)-2-{5-[4'-(dimethylamino)-6-nitrobiphenyl-3-yl]-1H-imidazol-2-yl}pyrrolidin-1-yl)-3-methyl-1-oxobutan-2-ylcarbamate (53), LC-MS (ESI) 535 (M+H)$^+$; methyl (S)-1-(S)-2-{5-[4'-(4-methylpiperazin-1-yl)-6-nitrobiphenyl-3-yl]-1H-imidazol-2-yl}pyrrolidin-1-yl)-3-methyl-1-oxobutan-2-ylcarbamate (54), LC-MS (ESI) 590 (M+H)$^+$; methyl (S)-3-methyl-1-((S)-2-{5-[4-nitro-3-(pyridin-3-yl)phenyl]-1H-imidazol-2-yl}pyrrolidin-1-yl)-1-oxobutan-2-ylcarbamate (55), LC-MS (ESI) 493 (M+H)$^+$.

To a solution of nitro-derivative 46-55 (0.7 mmol) in 40 mL of ethanol, Pd/C (40 mg, 10%) was added under Ar, the flask was blown with hydrogen, and the mixture was intensively stirred under hydrogen for 4 h (LC-MS control for complete reduction). The mixture was filtered through Celite and rotovapped. The residue 56-65 was dissolved in 2 mL of acetonitrile, and a solution of TsOH H$_2$O (0.571 g, 2.1 mmol) in 4 mL of MeCN was added. The mixture was cooled to 5-10° C., and a solution of NaNO$_2$ (97 mg, 1.4 mmol) and KI (0.29 g, 1.75 mmol) in 0.9 mL of water was added dropwise. The mixture was stirred for 1 h at rt, then diluted with a 5% NaHCO$_3$ solution, clarified with Na$_2$S$_2$O$_3$, and extracted with benzene. After drying and rotovapping, the residue was subjected to column chromatography on silica gel (toluene:EtOAc from 7:1 to 2:1) to afford methyl (S)-3-methyl-1-{(S)-2-[5-(3-aryl-4-iodophenyl)-1H-imidazol-2-yl]pyrrolidin-1-yl}-1-oxobutan-2-ylcarbamates 3(7)-3 (16). ((S)-1-{(S)-2-[5-(6-Iodo-biphenyl-3-yl)-1H-imidazol-2-yl]-pyrrolidine-1-carbonyl}-2-methyl-propyl)-carbamic acid methyl ester (3(7)), LC-MS (ESI) 629 (M+H)$^+$; ((S)-1-{(S)-2-[5-(2'-fluoro-6-iodo-biphenyl-3-yl)-1H-imidazol-2-yl]-pyrrolidine-1-carbonyl}-2-methyl-propyl)-carbamic acid methyl ester (3(8)), LC-MS (ESI) 629 (M+H)$^+$; methyl ((S)-1-{(S)-2-[5-(6-iodo-2'-methyl-biphenyl-3-yl)-1H-imidazol-2-yl]-pyrrolidine-1-carbonyl}-2-methyl-propyl)-carbamic acid methyl ester (3(9)), LC-MS (ESI) 629 (M+H)$^+$; ((S)-1-{(S)-2-[5-(3'-tert-butyl-6-iodo-biphenyl-3-yl)-1H-imidazol-2-yl]-pyrrolidine-1-carbonyl}-2-methyl-propyl)-carbamic acid methyl ester (3(10)), LC-MS (ESI) 629 (M+H)$^+$; ((S)-1-{(S)-2-[5-(4'-tert-butyl-6-iodo-biphenyl-3-yl)-1H-imidazol-2-yl]-pyrrolidine-1-carbonyl}-2-methyl-propyl)-carbamic acid methyl ester (3(11)), LC-MS (ESI) 629 (M+H)$^+$; ((S)-1-{(S)-2-[5-(6-iodo-[1,1';3',1"]terphenyl-3-yl)-1H-imidazol-2-yl]-pyrrolidine-1-carbonyl}-2-methyl-propyl)-carbamic acid methyl ester (3(12)), LC-MS (ESI) 649 (M+H)$^+$; ((S)-1-{(S)-2-[5-(6-iodo-[1,1';4',1"]terphenyl-3-yl)-1H-imidazol-2-yl]-pyrrolidine-1-carbonyl}-2-methyl-propyl)-carbamic acid methyl ester (3(13)), LC-MS (ESI) 649 (M+H)$^+$; ((S)-1-{(S)-2-[5-(4'-dimethylamino-6-iodo-biphenyl-3-yl)-1H-imidazol-2-yl]-pyrrolidine-1-carbonyl}-2-methyl-propyl)-carbamic acid methyl ester (3(14)), LC-MS (ESI) 616 (M+H)$^+$; [(S)-1-((S)-2-{5-[6-iodo-4'-(4-methyl-piperazin-1-yl)-biphenyl-3-yl]-1H-imidazol-2-yl}-pyrrolidine-1-carbonyl)-2-methyl-propyl]-carbamic acid methyl ester (3(15)), LC-MS (ESI) 671 (M+H)$^+$; and ((S)-1-{(S)-2-[5-(4-iodo-3-pyridin-3-yl-phenyl)-1H-imidazol-2-yl]-pyrrolidine-1-carbonyl}-2-methyl-propyl)-carbamic acid methyl ester (3(16)), LC-MS (ESI) 574 (M+H)$^+$.

Example 3 (Scheme 9)

Synthesis of (S)-tert-butyl 2-[5-(5-fluoro-6-iodobiphenyl-3-yl)-1H-imidazol-2-yl]pyrrolidine-1-carboxylate (3(15)-3(17))

A mixture of 2-bromo-6-fluoro-4-methylaniline (66) [WO 2007036715] (7.28 g, 35.7 mmol), phenylboronic acid (5.53 g, 45.4 mmol), Na$_2$CO$_3$ (11.4 g, 107 mmol), bis(triphenylphosphine)palladium(II) dichloride (1.255 g, 1.8 mmol) in 100 mL of ethanol, and 25 mL of water was stirred under Ar at 80° C. for 15 h. After the reaction was completed (LC-MS check), the cooled mixture was rotovapped from ethanol, diluted with water, and extracted with DCM. Column chromatography on silica gel (hexane:EtOAc 19:1) afforded 3-fluoro-5-methylbiphenyl-2-amine (67). $^1$H NMR (DMSO-d$_6$, 400 MHz) δ 7.44 (m, 4H), 7.36 (m, 1H), 6.88 (d, J=12.0 Hz, 1H), 6.70 (s, 1H), 4.43 (s, 2H), 2.20 (s, 3H).

To a solution of 67 (5.0 g, 24.8 mmoL) and TsOH H$_2$O (14.18 g, 74.5 mmol) in 100 mL of tert-BuOH, a solution of NaNO$_2$ (3.43 g, 49.7 mmol) and KI (10.31 g, 62.1 mmol) in 15 mL of water was added dropwise at 10-15° C. The mixture was stirred at rt for 1 h, diluted with a 5% NaHCO$_3$ solution, clarified with Na$_2$S$_2$O$_3$, and extracted with benzene. After drying and rotovapping, the residue was passed through a silica gel layer (hexane) to afford 3-fluoro-2-iodo-5-methylbiphenyl (70). $^1$H NMR (DMSO-d$_6$, 400 MHz) δ 7.44 (m, 3H), 7.31 (m, 2H), 7.11 (d, J=9.2 Hz, 1H), 7.01 (s, 1H), 2.33 (s, 3H).

To a stirred mixture of 70 (4.9 g, 15.7 mmol), 10 mL of pyridine and 20 mL of water, 10 g of KMnO$_4$ was added portionwise at 70-80° C., and the mixture was refluxed for 4 h. The mixture was cooled to 70-80° C., filtered through celite and celite was washed with hot water. The warm filtrate was basified with Na$_2$CO$_3$, extracted with toluene, and acidified with hydrochloric acid. The precipitated acid was filtered, washed with water, and dried in vacuum to yield 2.89 g of 5-fluoro-6-iodobiphenyl-3-carboxylic acid (73). $^1$H NMR (DMSO-d$_6$, 400 MHz) δ 13.47 (s, 1H), 7.65 (dd, J$_1$=8.0 Hz, J$_2$=1.6 Hz, 1H), 7.61 (d, J=1.6 Hz, 1H), 7.48 (m, 3H), 7.37 (m, 2H).

To a suspension of 73 (2.89 g, 8.45 mmol) in 20 mL of DCM, oxalyl chloride (1.3 mL, 15.4 mmol) and 1 drop of DMF were added. The mixture was stirred for 3 h, then rotovapped. The residue was dissolved in 40 mL of MeCN, and TMS-diazomethane (4.65 mL, 2 M in hexane, 9.3 mmol) was added at 0° C. The mixture was stirred for 15 h at 4° C., rotovapped, and subjected to column chromatography on silica gel (toluene) to afford 2.26 g of 2-diazo-1-(5-fluoro-6-iodobiphenyl-3-yl)ethanone (76). $^1$H NMR (DMSO-d$_6$, 400 MHz) δ 7.67 (dd, J$_1$=8.4 Hz, J$_2$=1.6 Hz, 1H), 7.59 (d, J=1.6 Hz, 1H), 7.49 (m, 3H), 7.38 (m, 2H), 7.19 (s, 1H).

To a solution of 76 (2.26 g, 6.2 mmol) in 100 mL of EtOAc, 8 mL of 4 M HCl in EtOAc was added at 0° C. The mixture was stirred for 2 h at rt, rotovapped, and subjected to column chromatography on silica gel (hexane:toluene 1:1) to afford 1.8 g of 2-chloro-1-(5-fluoro-6-iodobiphenyl-3-yl)ethanone (79). $^1$H NMR (CDCl$_3$, 400 MHz) δ 7.66 (d, J=2.0 Hz, 1H), 7.61 (dd, J$_1$=8.0 Hz, J$_2$=2.0 Hz, 1H), 7.49 (m, 3H), 7.35 (m, 2H), 4.65 (s, 2H).

The synthetic procedure given above for compounds 35-40 (Example 1) was used for the synthesis of 1-tert-butyl (S)-2-[2-(5-fluoro-6-iodobiphenyl-3-yl)-2-oxoethyl] pyrrolidine-1,2-dicarboxylate (82) using 79. Compound 82 has LC-MS (ESI) 554 (M+H)$^+$, $^1$H NMR (CDCl$_3$, 400 MHz) δ 7.59 (s, 1H), 7.55 (m, 1H), 7.48 (m, 3H), 7.34 (m, 2H), 5.32 (m, 2H), 4.45 (m, 1H), 3.59 (m, 1H), 3.45 (m, 1H), 2.31 (m, 2H), 2.06 (m, 1H), 1.94 (m, 1H), 1.44, 1.47 (2 s, 9H).

The synthetic procedure given above for compounds 3(1)-3(6) (Example 1) was used for synthesis of ((S)-1-{(S)-2-[5-(4-iodo-3-pyridin-3-yl-phenyl)-1H-imidazol-2-yl]-pyrrolidine-1-carbonyl}-2-methyl-propyl)-carbamic acid methyl ester (3(17)) with using of 82. Compound 3(17) has LC-MS (ESI) 534 (M+H)$^+$.

Similarly, (S)-2-[5-(5-fluoro-6-iodo-4'-methyl-biphenyl-3-yl)-1H-imidazol-2-yl]-pyrrolidine-1-carboxylic acid tert-butyl ester (3(18)), LC-MS (ESI) 548 (M+H)$^+$ and (S)-2-[5-(5,4'-difluoro-6-iodo-biphenyl-3-yl)-1H-imidazol-2-yl]-pyrrolidine-1-carboxylic acid tert-butyl ester (3(19)), LC-MS (ESI) 552 (M+H)$^+$ were synthesized.

Example 4 (Scheme 10)

Synthesis of methyl (S)-tert-butyl 2-[5-(6-iodo-5-methylbiphenyl-3-yl)-1H-imidazol-2-yl]pyrrolidine-1-carboxylate (3(20)-3(22))

To a stirred solution of methyl 4-amino-5-methylbenzoate (85) (2.48 g, 15 mmol) in 25 mL of AcOH, NBS (3.0 g, 17 mmol) was added portionwise, the mixture was stirred for 1 h, diluted with water, extracted with DCM, washed with a saturated NaHCO$_3$ solution, dried over Na$_2$SO$_4$, and rotovapped to yield 3.66 g of methyl 4-amino-3-bromo-5-methylbenzoate (86). $^1$H NMR (CDCl$_3$, 400 MHz) δ 8.03 (s, 1H), 7.71 (s, 1H), 4.50 (brs, 2H), 3.87 (s, 3H), 2.25 (s, 3H).

The synthetic procedure given above for compounds 17-22 (Example 1) was applied while using compound 86 for the synthesis of methyl 6-amino-5-methylbiphenyl-3-carboxylate (87), $^1$H NMR (DMSO-d$_6$, 400 MHz) δ 7.61 (d, J=1.2 Hz, 1H), 7.47 (m, 3H), 7.39 (m, 3H), 5.20 (s, 2H), 3.75 (s, 3H), 2.18 (s, 3H).

The synthetic procedure given above for compounds 3(7)-3(16) (Example 2) was applied while using compound 87 for the synthesis of methyl 6-iodo-5-methylbiphenyl-3-carboxylate (90). $^1$H NMR (DMSO-d$_6$, 400 MHz) δ 7.86 (d, J=1.2 Hz, 1H), 7.54 (d, J=1.2 Hz, 1H), 7.45 (m, 3H), 7.30 (m, 2H), 3.84 (s, 3H), 2.56 (s, 3H).

To a solution of ester 90 (3.3 g, 9.37 mmol) in 30 mL of THF and 30 mL of MeOH, a solution of LiOH H$_2$O (0.786 g, 18.74 mmol) was added, and the mixture was stirred for 15 h. The solution was rotovapped, dissolved in 50 mL of water, and acidified with 1.7 mL of hydrochloric acid. After 2 h, the resulting precipitate was filtered, washed with water, and dried in vacuum to yield 3.16 g of 6-iodo-5-methylbiphenyl-3-carboxylic acid (93), $^1$H NMR (DMSO-d$_6$, 400 MHz) δ 13.15 (s, 1H), 7.85 (d, J=1.2 Hz, 1H), 7.53 (d, J=1.2 Hz, 1H), 7.45 (m, 3H), 7.30 (m, 2H), 2.55 (s, 3H).

Further, by analogy with Example 3, 2-diazo-1-(6-iodo-5-methylbiphenyl-3-yl)ethanone (96), $^1$H NMR (DMSO-d$_6$, 400 MHz) δ 7.78 (s, 1H), 7.46 (m, 4H), 7.31 (m, 2H), 7.09 (s, 1H), 2.55 (s, 3H); 2-chloro-1-(6-iodo-5-methylbiphenyl-3-yl)ethanone (99), $^1$H NMR (CDCl$_3$, 400 MHz) δ 7.79 (m, 1H), 7.62 (m, 1H), 7.46 (m, 3H), 7.31 (m, 2H), 4.67 (s, 2H), 2.65 (s, 3H); tert-butyl (S)-2-[2-(6-iodo-5-methylbiphenyl-3-yl)-2-oxoethyl] pyrrolidine-1,2-dicarboxylate (102), LC-MS (ESI) 550 (M+H)$^+$. $^1$H NMR (CDCl$_3$, 400 MHz) δ 7.73 (m, 1H), 7.56 (s, 1H), 7.45 (m, 3H), 7.30 (m, 2H), 5.34 (m, 2H), 4.45 (m, 1H), 3.59 (m, 1H), 3.44 (m, 1H), 2.63 (s, 3H), 2.32 (m, 2H), 2.07 (m, 1H), 1.94 (m, 1H), 1.44, 1.47 (2 s, 9H); and (S)-2-[5-(6-iodo-5-methyl-biphenyl-3-yl)-1H-imidazol-2-yl]-pyrrolidine-1-carboxylic acid tert-butyl ester (3(20)), LC-MS (ESI) 530 (M+H)$^+$ were derived.

Similarly, (S)-2-[5-(6-iodo-5,4'-dimethyl-biphenyl-3-yl)-1H-imidazol-2-yl]-pyrrolidine-1-carboxylic acid tert-butyl ester (3(21)), LC-MS (ESI) 544 (M+H)$^+$ and (S)-2-[5-(4'-fluoro-6-iodo-5-methyl-biphenyl-3-yl)-1H-imidazol-2-yl]-pyrrolidine-1-carboxylic acid tert-butyl ester (3(22)), LC-MS (ESI) 548 (M+H)$^+$ were synthesized.

Example 5 (Scheme 11)

Synthesis of ((S)-1-{(S)-2-[5-(5-fluoro-6-iodo-biphenyl-3-yl)-1H-imidazol-2-yl]-pyrrolidine-1-carbonyl}-2-methyl-propyl)-carbamic acid methyl ester (3(23)) and ((S)-1-{(S)-2-[5-(5-fluoro-6-iodo-biphenyl-3-yl)-1H-imidazol-2-yl]-pyrrolidine-1-carbonyl}-2-methyl-propyl)-carbamic acid methyl ester (3(24))

Intermediates 3(23) with LC-MS (ESI) 591 (M+H)$^+$ and 3(24) with LC-MS (ESI) 587 (M+H)$^+$ were prepared from compounds 3(17) and 3(207) using the procedure described in Example 2 for the synthesis of compound 45 from 43.

Example 6 (Scheme 12)

Synthesis of [(S)-1-((S)-2-{5-[4-iodo-3-((R)-1-phenyl-ethoxy)-phenyl]-1H-imidazol-2-yl}-pyrrolidine-1-carbonyl)-2-methyl-propyl]-carbamic acid methyl ester (3(25))

A mixture of NaH (0.552 g, 13.8 mmol, 60% in oil, washed with hexane) and 20 mL of dry DMSO was stirred at 70° C. for 1 h. Then, (S)-1-phenylethanol (1.67 mL, 13.8 mmol) was added, and the mixture was stirred at 70° C. for 15 min. After cooling, 4-bromo-2-fluoro-1-nitrobenzene (105) [M. Schlosser et al, *Eur. J. Org. Chem.*, 13, 2956-2969, 2006] (2.64 g, 12 mmol) was added, and the mixture was stirred for 15 h at rt. The mixture was neutralized with 1 mL of AcOH, diluted with water, and extracted with benzene. Column chromatography on silica gel (hexane:benzene 3:1) afforded 2.76 g of (S)-4-bromo-1-nitro-2-(1-phenylethoxy)benzene (106), $^1$H NMR (CDCl$_3$, 400 MHz) δ 7.69 (d, J=9.2 Hz, 1H), 7.41 (m, 4H), 7.33 (m, 1H), 7.10 (m, 1H), 5.44 (q, J=6.4 Hz, 1H), 1.71 (d, J=6.4 Hz, 3H).

A mixture of (S)-4-bromo-1-nitro-2-(1-phenylethoxy)benzene (106) (0.674 g, 2.09 mmol), bis(pinacolato)diboron (0.638 g, 2.51 mmol), KOAc (0.616 g, 6.27 mmol) and Pd(dppf)Cl$_2$ (0.153 g, 0.21 mmol) in 8 mL of dioxane was stirred under Ar at 80° C. for 2 h. The mixture was rotovapped, dissolved in benzene, filtered through 1 cm layer of silica gel, and rotovapped. The resulting (S)-4,4,5,5-tetramethyl-2-[4-nitro-3-(1-phenylethoxy)phenyl]-1,3,2-dioxaborolane (107) was used directly for the next step.

A mixture of compound 107 thus obtained, methyl (S)-1-[(S)-2-(S)-iodo-1H-imidazol-2-yl)pyrrolidin-1-yl]-3-methyl-1-oxobutan-2-ylcarbamate (108) (0.878 g, 2.09 mmol), Na$_2$CO$_3$ (0.665 g, 6.27 mmol), and Pd(PPh$_3$)$_2$Cl$_2$ (73 mg, 0.105 mmol) in 20 mL of ethanol and 5 mL of water was stirred under Ar at 70° C. for 15 h. The cooled mixture was rotovapped from ethanol, diluted with water, and extracted with DCM. Column chromatography on silica gel (hexane:EtOAc 1:3) afforded 0.405 g of methyl (S)-1-((S)-2-{5-[4-nitro-3-((S)-1-phenylethoxy)phenyl]-1H-imidazol-2-yl}pyrrolidin-1-yl)-3-methyl-1-oxobutan-2-ylcarbamate (109). LC-MS (ESI) 536 (M+H)$^+$.

To a solution of compound 109 (0.397 g, 0.74 mmol) in 10 mL of ethanol, Na$_2$S$_2$O$_4$ (0.452 g, 2.6 mmol) and Et$_3$N (0.62 mL, 4.4 mmol) were added. The mixture was stirred for 2 h at 80° C., then rotovapped, 10 mL of water and 5 mL of AcOH were added, and the mixture was stirred at 60° C. for a further 1 h. The cooled mixture was basified with a saturated NaHCO$_3$ solution, extracted with DCM, dried over Na$_2$SO$_4$, and rotovapped to afford 0.304 g of methyl (S)-1-((S)-2-{5-[4-amino-3-((S)-1-phenylethoxy)phenyl]-1H-imidazol-2-yl}pyrrolidin-1-yl)-3-methyl-1-oxobutan-2-ylcarbamate (110), LC-MS (ESI) 506 (M+H)$^+$.

To a solution of TsOH.H$_2$O (0.343 g, 1.8 mmol) in 2 mL of MeCN cooled in a freezer, a cooled solution of compound 110 (0.304 g, 0.6 mmol) in 2.5 mL of MeCN was added. To this solution, a solution of NaNO$_2$ (83 mg, 1.2 mmol) and KI (0.249 g, 1.5 mmol) in 0.55 mL of water cooled to 0° C. was added, and the mixture was stirred for 15 h in a fridge, then diluted with a 5% NaHCO$_3$ solution, clarified with Na$_2$S$_2$O$_3$, and extracted with benzene. After drying and rotovapping, the residue was subjected to column chromatography on silica gel (hexane:EtOAc 1:3) to afford 0.152 g of [(S)-1-((S)-2-{5-[4-iodo-3-((R)-1-phenyl-ethoxy)-phenyl]-1H- imidazol-2-yl}-pyrrolidine-1-carbonyl)-2-methyl-propyl]-carbamic acid methyl ester (3(25)), LC-MS (ESI) 617 (M+H)$^+$.

Example 7 (Scheme 13)

Synthesis of ((S)-1-{(S)-2-[5-(4-iodo-3-phenoxy-phenyl)-1H-imidazol-2-yl]-pyrrolidine-1-carbonyl}-2-methyl-propyl)-carbamic acid methyl ester (3(26))

A mixture of 4-bromo-2-fluoro-1-nitrobenzene (105) (7.0 g, 31.8 mmol), phenol (3.1 g, 33.4 mmol), K$_2$CO$_3$ (4.8 g, 35.0 mmol) in 50 mL DMF was stirred at 75° C. for 3 h. The mixture was concentrated in vacuo, and the residue was partitioned between EtOAc and water. The organic layer was washed successively with 2N aqueous NaOH, 2N aqueous HCl, saturated aqueous NaHCO$_3$, and brine, dried over Na$_2$SO$_4$, and concentrated to give 4-bromo-1-nitro-2-phenoxybenzene (111) as orange crystals (8.4 g, 90%). $^1$H-NMR (CDCl$_3$, 400 MHz): 8.05 (d, J=8.6 Hz, 1H), 7.58 (d, J=8.6 Hz, 1H), 7.46 (dd, J$_1$=J$_2$=7.8 Hz, 1H), 7.25-7.30 (m, 2H), 7.08 (d, J=7.8 Hz, 2H).

A mixture of 111 (15.8 g, 53.7 mmol, KOAc (13.2 g, 0.13 mol), bis(pinacolato)diboron (27.3 g, 107.4 mmol), and 1,4-dioxane (150 mL) was degassed under N$_2$/vacuum purge. Then, Pd(PPh$_3$)$_4$ (1.6 g, 1.4 mmol) was added, and the reaction was heated at 100° C. for 18 h. The reaction was then cooled to ambient temperature and concentrated under reduced pressure. The mixture was partitioned between water (100 mL) and DCM (100 mL), then filtered to remove any solid, and washed with additional DCM (200 mL). The layers were separated, and the organic layer was washed with brine, dried over Na$_2$SO$_4$, filtered, and concentrated. The crude material was purified by silica gel chromatography using hexane/DCM (stepwise gradient, 9:1 to 4:1 to 2:1). Obtained 4,4,5,5-tetramethyl-2-(4-nitro-3-phenoxy-phenyl)-1,3,2-dioxaborolane (112), $^1$H-NMR (DMSO-d$_6$, 400 MHz): 8.04 (d, J=8.0 Hz, 1H), 7.57 (d, J=8.0 Hz, 1H), 7.42-7.48 (m, 2H), 7.22-7.27 (m, 2H), 7.12 (d, J=8.2 Hz, 2H), 1.26 (s, 12H).

A mixture of 112 (13 g, 38.1 mmol), 4-tert-butyl (S)-2-(5-iodo-1H-imidazol-2-yl)-pyrrolidine-1-carboxylate (113) (14.5 g, 40.0 mmol), and Na$_2$CO$_3$ (12.1 g, 114.3 mmol in 50 mL of H$_2$O) in 200 ml dioxane was stirred under N$_2$ for 15 min, then Pd(PPh$_3$)$_4$ (1.3 g, 1.2 mmol) was added, and the reaction mixture was stirred at 90° C. for 15 h. The mixture was concentrated in vacuo, and the residue was partitioned between EtOAc and water. The organic layer was washed with water and brine, dried over Na$_2$SO$_4$, and concentrated. The crude product was purified by column chromatography on silica gel using hexane/ethyl acetate as eluent to afford tert-butyl (S)-2-[5-(4-nitro-3-phenoxyphenyl)-1H-imidazol-2-yl]pyrrolidine-1-carboxylate (114) (6.4 g, 37%), $^1$H-NMR (DMSO-d$_6$, 400 MHz): 12.20-12.10 (m, 1H), 8.07 (d, J=8.6 Hz, 1H), 7.78 (br.s, 1H), 7.72 (dd, J$_1$=8.6 Hz, J$_2$=1.7 Hz, 1H), 7.50 (d, J=1.7 Hz, 1H), 7.43-7.37 (m, 2H), 7.21-7.16 (m, 1H), 7.06 (d, J=8.0 Hz, 1H), 4.80-4.70 (m, 1H), 3.52-3.44 (m, 1H), 3.35-3.32 (m, 1H), 2.25-2.10 (m, 1H), 1.92-1.78 (m, 3H), 1.38, 1.12 (2×s, 9H).

The compound was obtained by adding an excess of 4M HCl in dioxane to a solution of 114 in dioxane, and the reaction mixture was stirred at ambient temperature for 2 h. The resulting reaction mixture was evaporated to afford 5-(4-nitro-3-phenoxyphenyl)-2-[(S)-pyrrolidin-2-yl]-1H-imidazole dihydrochloride (115.2HCl) (6.0 g, 99%), $^1$H-NMR (DMSO-d$_6$, 400 MHz): 10.08 (br.s, 1H), 9.28 (br.s, 1H), 8.15 (d, J=8.5 Hz, 1H), 8.06 (s, 1H), 7.83 (d, J=8.5 Hz, 1H), 7.64 (s, 1H), 7.40-7.45 (m, 2H), 7.17-7.22 (m, 1H), 7.06 (d, J=8.2 Hz, 2H), 4.77 (br.s, 2H), 3.28 (br.s, 2H), 2.32-2.41 (m, 1H), 2.15-2.24 (m, 1H), 2.05-2.13 (m, 1H), 1.94-2.02 (m, 1H).

Dihydrochloride 115.2HCl (6.2 g, 14.6 mmol) was dissolved in 50 mL MeCN, then DIPEA (8.9 ml, 43.8 mmol) was added, and the mixture was cooled down to 0° C., after which a moc-Val (3.1 g, 17.5 mmol) and TBTU (5.6 g, 17.5 mmol) were added. The reaction mixture was stirred for 3 h at 0° C., and then was concentrated, dissolved in DCM, and washed with aq NaHCO$_3$, citric acid, H$_2$O, and brine, dried over Na$_2$SO$_4$, and concentrated. The residue was purified by column chromatography on silica gel using CCl$_4$/CH$_2$Cl$_2$-ethyl acetate, CH$_2$Cl$_2$-MeOH as eluent to give methyl (S)-2-methyl-1-{(S)-2-[5-(4-nitro-3-phenoxy-phenyl)-1H-imidazol-2-yl]-pyrrolidine-1-carbonyl}-propyl)-carbamate (116) (7.0 g, 94%), $^1$H-NMR (DMSO-d$_6$, 400 MHz): 12.10 (s, 1H), 8.08 (d, J=8.6 Hz, 1H), 7.78 (d, J=1.7 Hz, 1H), 7.68 (dd, J$_1$=8.6 Hz, J$_2$=1.7 Hz, 1H), 7.48 (d, J=1.7 Hz, 1H), 7.43-7.38 (m, 2H), 7.22-7.18 (m, 1H), 7.05-7.01 (m, 3H), 5.02-4.99 (m, 1H), 4.02-3.98 (m, 1H), 3.80-3.68 (m, 2H), 3.52 (s, 3H), 3.35-3.32 (m, 1H), 2.25-1.80 (m, 4H), 0.80-0.74 (m, 6H).

To compound 116 dissolved in 500 mL of MeOH, 700 mg 10% Pd/C was added, and hydrogen gas was bubbled through the reaction mixture for 4 h at ambient temperature. After the reaction was completed (TLC check), the reaction mixture was filtered through Celite and the filtrate was evaporated. The crude residue was purified by column chromatography on silica gel using CH$_2$Cl$_2$-ethyl acetate/CH$_2$Cl$_2$-MeOH as eluent, to afford methyl ((S)-1-{(S)-2-[5-(4-amino-3-phenoxy-phenyl)-1H-imidazol-2-yl]-pyrrolidine-1-carbonyl}-2-methyl-propyl)-carbamate (117) (4.9 g, 74%), $^1$H-NMR (DMSO-d$_6$, 400 MHz): 11.80-11.50 (m, 1H), 7.33-7.28 (m, 3H), 7.26-7.22 (m, 1H), 7.20-7.15 (m, 2H), 7.05-6.99 (m, 1H), 6.93-6.87 (m, 3H), 6.80-6.74 (m, 2H), 5.02-4.97 (m, 1H), 4.85-4.78 (m, 1H), 4.05-3.95 (m, 1H), 3.78-3.70 (m, 2H), 3.52 (s, 3H), 2.10-2.03 (m, 1H), 1.95-1.83 (m, 3H), 0.80-0.74 (m, 6H).

Compound 117 (2.0 g, 4.1 mmol) and p-TsOH (3.2 g, 16.5 mmol) were mixed in 20 ml MeCN, the solution was cooled to 10° C. and a solution of NaNO$_2$ (0.58 g, 8.2 mmol) and KI (2.1 g, 12.3 mmol) in 20 ml H$_2$O was added dropwise, N$_2$ evolved, and the mixture turned iodine-dark. The reaction mixture was stirred for 3 h at RT, then aq. Na$_2$SO$_3$ and aq. NaHCO$_3$ were added to the mixture to quench the run, and the mixture was extracted with ethyl acetate (2×2.0 mL). The extract was washed with water (3×0.30 mL) and dried over anhydrous sodium sulfate. The crude residue was purified by column chromatography on silica gel eluting with CCl$_4$/CH$_2$Cl$_2$-ethyl acetate/CH$_2$Cl$_2$-MeOH as eluent to afford ((S)-1-{(S)-2-[5-(4-iodo-3-phenoxy-phenyl)-1H-imidazol-2-yl]-pyrrolidine-1-carbonyl}-2-methyl-propyl)-carbamic acid methyl ester (3(26)) (1.7 g, 69%), $^1$H-NMR (DMSO-d$_6$, 400 MHz): 11.85 (s, 1H), 7.82 (d, J=8.0 Hz, 1H), 7.54 (d, J=1.9 Hz, 1H), 7.42-7.32 (m, 4H), 7.23 (d, J=8.6 Hz, 1H), 7.13-7.08 (m, 1H), 6.93-6.89 (m, 2H), 5.02-4.97 (m, 1H), 4.02-3.98 (m, 1H), 3.78-3.68 (m, 2H), 3.52 (s, 3H), 2.12-2.00 (m, 2H), 1.95-1.80 (m, 3H), 0.80-0.74 (m, 6H).

Example 8 (Scheme 14)

Synthesis of 5-(4-iodo-3-phenylsulfanyl-phenyl)-2-(S)-pyrrolidin-2-yl-1H-imidazoles (3(27)-3(29))

To a solution of 1-(4-aminophenyl)ethanone (118) (10 g, 74 mmol) in MeCN (100 mL), ammonium acetate was added (0.548 g, 7.4 mmol) following by addition of N-bromosuccinimide (13.3 g, 75 mmol) portionwise at ambient temperature. The reaction mixture was stirred for 10 min at ambient temperature. The reaction was quenched with aq $Na_2SO_3$, MeCN was partially evaporated, the residue was diluted with water and extracted with EtOAc, the combined organic extracts were dried with $Na_2SO_4$ and evaporated. The residue was purified by column chromatography on silica gel eluting with 1-20% EtOAc in hexane to give 1-(4-amino-3-bromophenyl)ethanone (119) (14.1 g, 89%), $^1$H-NMR (CDCl$_3$, 400 MHz): 8.05 (d, J=1.8 Hz, 1H), 7.72 (dd, J$_1$=1.8 Hz, J$_2$=8.4 Hz, 1H), 6.75 (d, J=8.4 Hz, 1H), 4.61 (br.s, 2H), 2.50 (s, 3H).

Mixture of compound (119) (9 g, 42 mmol) and m-CPBA (51.8 g of 70 wt %, 210 mmol) were dissolved in toluene (100 mL) and heated under reflux for 6 h. After the mixture cooled to room temperature, the solid formed was filtered and washed with ether. The filtrate was washed with sodium hydroxide (10%). After evaporation of the solvent, the residue was purified by column chromatography on silica gel eluting with 1-20% EtOAc in hexane giving 1-(4-nitro-3-bromophenyl)ethanone (120) (3.7 g, 36%), $^1$H-NMR (CDCl$_3$, 400 MHz): 8.29 (d, J=1.8 Hz, 1H), 8.01 (dd, J$_1$=1.8 Hz, J$_2$=8.4 Hz, 1H), 7.88 (d, J=8.4 Hz, 1H), 2.66 (s, 3H).

To a solution of compound 120 (3.65 g, 14.9 mmol) in dioxane (50 mL), a solution of bromine (2.62, 16.4 mmol) in dioxane (20 mL) was added dropwise at 10° C. The reaction mixture was stirred at ambient temperature for 1 h, and quenched with aq $Na_2SO_3$. Dioxane was partially evaporated, the residue was extracted with EtOAc, and the combined organic extracts were dried with $Na_2SO_4$ and evaporated. The solidified residue was washed with cold i-PrOH and dried giving 2-bromo-1-(4-nitro-3-bromophenyl)ethanone (121) (3.6 g, 75%), $^1$H-NMR (CDCl$_3$, 400 MHz): 8.34 (d, J=1.8 Hz, 1H), 8.06 (dd, J$_1$=1.8 Hz, J$_2$=8.4 Hz, 1H), 7.91 (d, J=8.4 Hz, 1H), 3.71 (s, 2H).

To a solution of compound 121 (3.6 g, 11.1 mmol) and Boc-L-proline (2.64 g, 12.26 mmol) in MeCN (100 mL), DIPEA was added (3.88 mL, 22.3 mmol), and the reaction mixture was stirred at ambient temperature for 15 h. Then, aq NaHCO$_3$ was added to the reaction mixture, the mixture was extracted with EtOAc, and the combined organic extracts were dried with $Na_2SO_4$ and evaporated. The residue was purified by column chromatography on silica gel eluting with 1-3% MeOH in CH$_2$Cl$_2$ to give 1-tert-butyl 2-[2-(3-bromo-4-nitrophenyl)-2-oxoethyl] (S)-pyrrolidine-1,2-dicarboxylate (122) (4.27 g, 84%), $^1$H-NMR (DMSO-d$_6$, 400 MHz): 8.42 (d, J=9.8 Hz, 1H), 8.21-8.11 (m, 2H), 5.70-5.46 (m, 2H), 4.38-4.30 (m, 1H), 3.43-3.27 (m, 2H), 2.36-2.21 (m, 1H), 2.14-2.04 (m, 1H), 1.94-1.81 (m, 2H), 1.39, 1.36 (2×br.s, 9H).

To a solution of compound 122 (4.27 g, 9.3 mmol) in PhMe (50 mL), ammonium acetate was added (10.37 g, 140 mmol), and the mixture was stirred at 110° C. for 48 h. Aq NaHCO$_3$ was added to the reaction mixture, the mixture was extracted with EtOAc, and the combined organic extracts were dried with $Na_2SO_4$ and evaporated. The residue was purified by column chromatography on silica gel eluting with 5-40% EtOAc in hexane to give tert-butyl (S)-2-[5-(3-bromo-4-nitrophenyl)-1H-imidazol-2-yl]pyrrolidine-1-carboxylate (123) (3.0 g, 74%), $^1$H-NMR (DMSO-d$_6$, 400 MHz): 12.3-12.13 (m, 1H), 8.2 (s, 1H), 8.03 (d, J=8.6 Hz, 1H), 7.96-7.82 (m, 2H), 4.88-4.71 (m, 1H), 3.61-3.46 (m, 1H), 3.42-3.32 (m, 1H), 2.33-2.11 (m, 1H), 2.07-1.77 (m, 3H), 1.39, 1.14 (2×br.s, 9H).

To a solution of compound 123 (1.9 g, 3.4 mmol) and PhSH (0.55 mL, 4.4 mmol) in EtOH (20 mL), 10M aq NaOH (0.66 mL, 5.4 mmol) was added, and the mixture was stirred at 60° C. for 48 h. After the mixture was cooled to room temperature, EtOH was evaporated, H$_2$O was added, the mixture was extracted with EtOAc, and the combined organic extracts were dried with $Na_2SO_4$ and evaporated. The residue was purified by column chromatography on silica gel eluting with 5-40% EtOAc in hexane to give tert-butyl (S)-2-{5-[4-nitro-3-(phenylthio)phenyl]-1H-imidazol-2-yl}pyrrolidine-1-carboxylate (124) (1.75 g, 86%), $^1$H-NMR (DMSO-d$_6$, 400 MHz): 12.13-12.03 (m, 1H), 8.21 (d, J=8.6 Hz, 1H), 7.68-7.60 (m, 3H), 7.60-7.54 (m, 3H), 7.53-7.47 (m, 1H), 7.35 (s, 1H), 4.74-4.60 (m, 1H), 3.45-3.23 (m, 2H), 2.19-2.00 (m, 1H), 1.95-1.69 (m, 3H), 1.37, 1.10 (2×br.s, 9H).

To a solution of compound 124 (1.75 g, 3.7 mmol) in EtOH (20 mL), SnCl$_2$×2H$_2$O (4.23 g, 18.5 mmol) was added, and the mixture was stirred at ambient temperature overnight. The mixture was diluted with NH$_4$Cl, filtered through Celite, then extracted with EtOAc, and the combined organic extracts were dried with $Na_2SO_4$ and evaporated. The residue was purified by column chromatography on silica gel eluting with 0-50% EtOAc in DCM to give tert-butyl (S)-2-{5-[4-amino-3-(phenylthio)phenyl]-1H-imidazol-2-yl}pyrrolidine-1-carboxylate (125) (1.6 g, 97%), $^1$H-NMR (DMSO-d$_6$, 400 MHz): 11.95-11.6 (m, 1H), 7.78-7.43 (m, 2H), 7.40-6.95 (m, 6H), 6.90-6.73 (m, 1H), 5.35 (br.s, 2H), 4.85-4.63 (m, 1H), 3.45-3.23 (m, 2H), 2.19-2.00 (m, 1H), 1.95-1.69 (m, 3H), 1.37, 1.10 (2×br.s, 9H).

To a solution of compound 125 (1.6 g, 3.67 mmol) and p-TsOH monohydrate (2.39 g, 14.7 mmol) in MeCN (100 mL), a solution of sodium nitrite (0.74 g, 11.0 mmol) and potassium iodide (2.39 g, 14.7 mmol) in H$_2$O (50 mL) was added dropwise at 10° C. The reaction mixture was stirred at ambient temperature for 2 h, then aq. Na$_2$SO$_3$ and aq. NaHCO$_3$ were added, the mixture was extracted with EtOAc, and the combined organic extracts were dried with Na$_2$SO$_4$ and evaporated. The residue was purified by column chromatography on silica gel eluting with 0-50% EtOAc in DCM to give (S)-2-[5-(4-iodo-3-phenylsulfanyl-phenyl)-1H-imidazol-2-yl]-pyrrolidine-1-carboxylic acid tert-butyl ester (3(27)) (0.8 g, 40%)., $^1$H-NMR (DMSO-d$_6$, 400 MHz): 11.95-11.83 (m, 1H), 7.87 (d, J=8.6 Hz, 1H), 7.65-7.57 (m, 1H), 7.48-6.26 (m, 7H), 4.80-4.65 (m, 1H), 3.54-3.38 (m, 1H), 3.38-3.26 (m, 1H), 2.24-2.03 (m, 1H), 2.01-1.74 (m, 3H), 1.37, 1.11 (2×br.s, 9H).

To a solution of compound 3(27) (0.8 g, 1.46 mmol) in dioxane (7 mL), 4M HCl in dioxane (7 mL) was added, and the mixture was kept at ambient temperature for 2 h. Dioxane was evaporated to dryness, the residual solid was washed with Et$_2$O and dried to give 55-(4-i-3-phenylsulfanyl-phenyl)-2-(S)-pyrrolidin-2-yl-1H-imidazole dihydrochloride (3(28)) (0.76 g, 100%), LC-MS (ESI) (m/z): 447.8 (M+H)$^+$.

To a mixture of compound 3(28).2HCl (0.76 g, 1.46 mmol), Moc-L-valine (0.307 g, 1.75 mmol), and DIPEA (1.02 mL, 5.84 mmol) in DMF (15 mL), TBTU (0.563 g, 1.75 mmol) was added at 10° C. and the reaction mixture was stirred at ambient temperature for 3 h. The mixture was diluted with water, extracted with EtOAc, and the combined organic extracts were dried with Na$_2$SO$_4$ and evaporated. The residual DMF was evaporated at 0.5 mm Hg and 50° C. The residue was purified by column chromatography on silica gel eluting with 0-30% EtOAc in DCM to give methyl ((S)-1-{(S)-2-[5-(4-iodo-3-phenylsulfanyl-phenyl)-1H-imidazol-2-yl]-pyrrolidine-1-carbonyl}-2-methyl-propyl)-carbamic acid methyl ester (3(29)) (0.71 g, 80%), $^1$H-NMR (DMSO-d$_6$, 400 MHz): 11.8 (br.s, 1H), 7.84 (d, J=8.4 Hz, 1H), 7.61 (br.s, 1H), 7.46-7.26 (m, 7H), 7.20-7.13 (m, 1H), 5.03-4.96 (m, 1H), 4.05-3.96 (m, 1H), 3.80-3.64 (m, 2H), 3.57 (s, 3H), 2.14-2.05 (m, 2H), 2.00-1.78 (m, 4H), 0.82-0.71 (m, 6H).

Example 9 (Scheme 15)

Synthesis of [(S)-1-((S)-2-{5-[4-iodo-3-(methyl-phenyl-amino)-phenyl]-1H-imidazol-2-yl}-pyrrolidine-1-carbonyl)-2-methyl-propyl]-carbamic acid methyl ester (3(30))

To a solution of 105 (10 g, 45.5 mmol) and aniline (5.08 g 54.5 mmol) in 100 mL NMP, potassium acetate was added (18.8 g, 136.4 mmol). The reaction mixture was stirred for 48 h at 50° C. The reaction was diluted with 500 ml of water. The formed residue was filtered off, washed with $H_2O$, dried, and washed with an ice-cold mixture of hexane/$Et_2O$ 2:1 to give (5-bromo-2-nitrophenyl)phenylamine (126) (7.63 g, 57%), $^1$H-NMR (DMSO-$d_6$, 400 MHz): 9.47 (s, 1H), 8.05 (d, J=9.2 Hz, 1H), 7.47 (dd, $J_1$=$J_2$=8.0 Hz, 2H), 7.37-7.33 (m, 2H), 7.27 (dd, $J_1$=$J_2$=7.6 Hz, 1H), 7.16 (d, J=2.0 Hz, 1H), 7.02 (dd, $J_1$=8.8 Hz, $J_2$=2.0 Hz), To a solution of 126 (7.63 g, 26 mmol) in 90 ml DMF, NaH was added (1.35 g, 33.8 mmol, 60 percent dispersion in oil) at 0° C., and the mixture was stirred at 0° C. for 0.5 h. MeI (3.7 g, 26 mmol) was added and the mixture was stirred at 0° C. for 2 h. The reaction was quenched by adding a saturated aqueous solution of ammonium chloride and extracted with $Et_2O$. The combined organic layers were washed with $H_2O$, then with brine, and dried over $MgSO_4$, filtered, and the filtrate was concentrated. The residue was purified by chromatography on silica gel (hexane:$CCl_4$:EtOAc, 30:10:1) to give (5-bromo-2-nitrophenyl)methyl(phenyl)amine (127) (7.5 g, 93%), $^1$H-NMR (DMSO-$d_6$, 400 MHz): 7.83 (d, J=8.8 Hz, 1H), 7.75 (d, J=2.0 Hz, 1H), 7.53 (dd, $J_1$=8.8 Hz, $J_2$=2.0 Hz 1H), 7.20 (dd, $J_1$=$J_2$=8.4 Hz, 2H), 6.87 (d, $J_1$=$J_2$=7.21H), 6.76 (d, J=8 Hz, 2H), 3.29 (s, 3H).

To a mixture of 127 (7.2 g, 23 mmol), bis(pinacolato)diboron (5.95 g, 23 mmol), and KOAc (6.9 g, 70 mmol) in 100 mL dioxane, Pd(dppf)$Cl_2$ was added (0.77 g, 0.97 mmol), and the mixture was stirred in inert atmosphere (nitrogen gas) at 80° C. for 20 h. The reaction was diluted with water, extracted with EtOAc, and the combined organic extracts were dried with $Na_2SO_4$ and evaporated. The residue was purified by column chromatography on silica gel eluting with 2-10% EtOAc in hexane to give N-methyl-2-nitro-N-phenyl-5-(4,4,5,5-tetramethyl-1,3,2-dioxaborolan-2-yl)aniline (128) (4.27 g, 52%), $^1$H-NMR (DMSO-$d_6$, 400 MHz): 7.92 (d, J=8.4 Hz, 1H), 7.67-7.65 (m, 2H), 7.17 (dd, J1=J2=8.8 Hz, 2H), 6.80 (d, $J_1$=$J_2$=7.2 Hz, 1H), 6.64 (d, J=8.2 Hz, 2H), 3.23 (s, 3H), 1.31 (s, 12H).

To a mixture of 108 (5.2 g, 12.3 mmol), boronic ester 128 (4.17 g, 11.7 mmol), and $Na_2CO_3$ (3.74 g, 35 mmol) in 50 mL dioxane and 20 mL $H_2O$, Pd(PPh$_3$)$_4$ was added (1.3 g, 0.011 mmol), and the mixture was stirred in inert atmosphere (nitrogen gas) at 90° C. for 20 h. The reaction was diluted with water, extracted with EtOAc, the combined organic extracts were washed with 5% aq $Na_2CO_3$, $H_2O$, brine, dried with $Na_2SO_4$, and evaporated. The residue was purified by column chromatography on silica gel eluting with 1.0-5% MeOH in CHCl$_3$ to give methyl {(S)-1-isopropyl-2-[(S)-2-(5-{3-[methyl(phenyl)amino]-4-nitrophenyl}-1H-imidazol-2-yl)pyrrolidin-1-yl]-2-oxoethyl}carbamate (129) (3.3 g, 53%), LC-MS (ESI) (m/z, relative intensity): 521.7 (100) (M+H)$^+$, 364.5 (20), 295.3 (15). $^1$H-NMR (DMSO-$d_6$, 400 MHz): 12.55-11.94 (m, 1H), 7.95 (d, J=8.4 Hz, 1H), 7.79 (br.s, 1H), 7.74 (d, J=8.8 Hz, 1H), 7.64-7.60 (m, 1H), 7.25 (d, J=7.6 Hz, 1H), 7.15 (dd, $J_1$=$J_2$=8 Hz, 2H), 6.75 (dd, $J_1$=$J_2$=7.2 Hz, 1H), 6.63 (d, J=7.6 Hz, 2H), 5.25-4.99 (m, 1H), 3.92 (s, 1H), 3.77 (br.s, 2H), 3.53 (s, 3H), 3.26 (s, 3H), 2.24-2.03 (m, 2H), 2.01-1.78 (m, 3H), 0.89-0.77 (m, 6H).

To a solution of 129 (3.3 g, 6.34 mmol) in 400 mL of MeOH, 10% Pd/C (0.37 g) was added, and the reaction mixture was stirred overnight in a stream of $H_2$. Then, the reaction mixture was filtered through celite, the filtrate was evaporated to give methyl {(S)-2-[(S)-2-(5-{4-amino-3-[methyl(phenyl)amino]phenyl}-1H-imidazol-2-yl)pyrrolidin-1-yl]-1-isopropyl-2-oxoethyl}carbamate (130) (2.98 g, 95%), LC-MS (ESI) (m/z, relative intensity): 981.3 (50) (2M+H)$^+$, 491.3 (100) (M+H)$^+$, 315.0 (40).

To a solution of compound 130 (2.65 g, 5.4 mmol) and p-TsOH monohydrate (4.11 g, 21.6 mmol) in 33 mL MeCN, a solution of potassium iodide (6.27 g, 37.8 mmol) in 4 mL $H_2O$ was added, then a solution of sodium nitrite (0.746 g, 10.8 mmol) in 4 mL $H_2O$ was added dropwise at 0° C. The reaction mixture was stirred at ambient temperature for 20 h and quenched with aq $Na_2SO_3$. The resulting brown pellet was extracted with EtOAc, the combined organic extracts were washed with 5% aq NaHCO$_3$, $H_2O$ brine, dried with $Na_2SO_4$, and evaporated. The residue was purified by column chromatography on silica gel eluting with 5-30% MeCN in CHCl$_3$ to give [(S)-1-((S)-2-{5-[4-iodo-3-(methyl-phenyl-amino)-phenyl]-1H-imidazol-2-yl}-pyrrolidine-1-carbonyl)-2-methyl-propyl]-carbamic acid methyl ester (3(30)) (1.02 g, 31%), LC-MS (ESI) (m/z, relative intensity): 602.0.3 (100) (M+H)$^+$, 445.0 (20), 428.3 (15), 376.5 (20). $^1$H-NMR (DMSO-$d_6$, 400 MHz): 12.17-11.74 (m, 1H), 7.97-7.84 (m, 1H), 7.54-7.52 (m, 2H), 7.43 (d, J=8 Hz, 1H), 7.22 (d, J=8.8 Hz, 1H), 7.14 (dd, $J_1$=$J_2$=7.6 Hz, 2H), 6.68 (dd, $J_1$=$J_2$=6.8 Hz, 1H), 6.48 (d, J=8 Hz, 2H), 5.2-4.97 (m, 1H), 4.01 (dd, $J_1$=$J_2$=8.4 Hz, 1H), 3.75 (br.s, 2H), 3.52 (s, 3H), 3.15 (s, 3H), 2.18-2.00 (m, 2H), 1.97-1.79 (m, 3H), 0.87-0.75 (m, 6H).

Example 10 (Scheme 16)

Synthesis of (S)-2-(5-{6-[(4-trimethylsilyl)buta-1,3-diynyl]biphenyl-3-yl}-1H-imidazol-2-yl)pyrrolidine-1-carboxylic acid tert-butyl esters (3(31)-3(34))

To a stirred solution of 1,4-bis(trimethylsilyl)buta-1,3-diyne (131) (0.37 g, 1.9 mmol) in 10 mL of diethyl ether, 1.5 mL (2.25 mmol) of 1.5 M methyllithium lithium bromide complex solution in diethyl ether was added under argon. The mixture was stirred at room temperature for 15 h, then cooled in an ice bath, and quenched with 10 mL of saturated NH$_4$Cl solution. The organic layer was washed with brine, dried over Na$_2$SO$_4$ and the solvent was stripped off on rotovap in a weak vacuum. To a solution of (trimethylsilyl)buta-1,3-diyne (132) in 14 mL of THF, iodide 3(1) (0.65 g, 1.26 mmol), 4 mL of TEA, Pd(PPh$_3$)$_4$ (73 mg, 0.063 mmol), and CuI (25 mg, 0.13 mmol) were added, and the mixture was stirred under argon at 45° C. for 15 h. The mixture was filtered through celite, rotovapped, and subjected to column chromatography on SiO$_2$ (chloroform:acetone 19:1) to afford 0.432 g (67%) of (S)-2-{5-[6-(4-trimethylsilanyl-buta-1,3-diynyl)-biphenyl-3-yl]-1H-imidazol-2-yl}-pyrrolidine-1-carboxylic acid tert-butyl ester (3(31)), LC-MS (ESI) 510 (M+H)$^+$.

Similarly, (S)-2-{5-[3'-tert-butyl-6-(4-trimethylsilanyl-buta-1,3-diynyl)-biphenyl-3-yl]-1H-imidazol-2-yl}-pyrrolidine-1-carboxylic acid tert-butyl ester (3(32)), LC-MS (ESI) 566 (M+H)⁺; (S)-2-{5-[6-(4-trimethylsilanyl-buta-1,3-diynyl)-[1,1';3',1"]terphenyl-3-yl]-1H-imidazol-2-yl}-pyrrolidine-1-carboxylic acid tert-butyl ester (3(33)), LC-MS (ESI) 586 (M+H)⁺, and (S)-2-{5-[3-naphthalen-2-yl-4-(4-trimethylsilanyl-buta-1,3-diynyl)-phenyl]-1H-imidazol-2-yl}-pyrrolidine-1-carboxylic acid tert-butyl ester (3(34)), LC-MS (ESI) 560 (M+H)⁺ were synthesized.

Example 11 (Scheme 17)

Synthesis of (S)-2-(5-[6-(buta-1,3-diynyl)biphenyl-3-yl]1H-imidazol-2-yl)pyrrolidine-1-carboxylic acid tert-butyl esters (3(35)-3(38))

To a solution of 3(31) (0.432 g, 0.85 mmol) in 5 mL of THF and 5 mL of methanol was added $K_2CO_3$ (0.352 g, 2.55 mmol) and the mixture was stirred under argon for 2 h, then filtered and rotovapped to give (S)-2-[5-(6-buta-1,3-diynyl-biphenyl-3-yl)-1H-imidazol-2-yl]-pyrrolidine-1-carboxylic acid tert-butyl ester (3(35)), LC-MS (ESI) 438 (M+H)⁺.

Similarly, (S)-2-[5-(6-buta-1,3-diynyl-3'-tert-butyl-biphenyl-3-yl)-1H-imidazol-2-yl]-pyrrolidine-1-carboxylic acid tert-butyl ester 3(36), LC-MS (ESI) 494 (M+H)⁺; (S)-2-[5-(6-buta-1,3-diynyl-[1,1';3',1"]terphenyl-3-yl)-1H-imidazol-2-yl]-pyrrolidine-1-carboxylic acid tert-butyl ester 3(37), LC-MS (ESI) 514 (M+H)⁺; and (S)-2-[5-(4-buta-1,3-diynyl-3-naphthalen-2-yl-phenyl)-1H-imidazol-2-yl]-pyrrolidine-1-carboxylic acid tert-butyl ester 3(38), LC-MS (ESI) 488 (M+H)⁺ were synthesized.

Example 12 (Scheme 18)

Synthesis of (S)-2-{5-[(4-{2-[(S)-pyrrolidin-2-yl]-1H-imidazol-5-yl}-(2-arylphenyl)buta-1,3-diynyl]-1H-imidazol-2-yl}pyrrolidine tetrahydrochlorides (4(1).4HCl)-(4(4).4HCl)

To a solution of 3(35) in 6 mL of THF, tert-butyl (S)-2-(5-iodo-1H-imidazol-2-yl)-pyrrolidine-1-carboxylate (78) (0.307 g, 0.85 mmol), 2 mL of TEA, Pd(PPh₃)₄ (49 mg, 0.043 mmol), and CuI (16 mg, 0.085 mmol) were added, and the mixture was stirred under argon at 40° C. for 15 h. The mixture was diluted with DCM, filtered, washed with saturated NH₄Cl solution, rotovapped and subjected to HPLC to afford 0.159 g (28%) of compound tert-Butyl (S)-2-{5-[(5-{2-[(S)-1-(tert-butoxycarbonyl)pyrrolidin-2-yl]-1H-imidazol-5-yl}biphenyl-2-yl)buta-1,3-diynyl]-1H-imidazol-2-yl}pyrrolidine-1-carboxylate (133), LC-MS (ESI) 673 (M+H)⁺.

Similarly, tert-butyl (S)-2-{5-[(5-{2-[(S)-1-(tert-butoxycarbonyl)pyrrolidin-2-yl]-1H-imidazol-5-yl}-3'-tert-butyl-biphenyl-2-yl)buta-1,3-diynyl]-1H-imidazol-2-yl}pyrrolidine-1-carboxylate (134), LC-MS (ESI) 729 (M+H)⁺, tert-butyl (S)-2-{5-[(5-{2-[(S)-1-(tert-butoxycarbonyl)pyrrolidin-2-yl]-1H-imidazol-5-yl}-[1,1';3',1"]terphenyl-2-yl)buta-1,3-diynyl]-1H-imidazol-2-yl}pyrrolidine-1-carboxylate (135), LC-MS (ESI) 749 (M+H)⁺, and tert-butyl (S)-2-{5-[(4-{2-[(S)-1-(tert-butoxycarbonyl)pyrrolidin-2-yl]-1H-imidazol-5-yl}-2-[naphthalen-2-yl]phenyl)buta-1,3-diynyl]-1H-imidazol-2-yl}pyrrolidine-1-carboxylate (136), LC-MS (ESI) 723 (M+H)⁺ were synthesized.

(S)-2-(5-{6-[4-((S)-2-Pyrrolidin-2-yl-3H-imidazol-4-yl)-buta-1,3-diynyl]-biphenyl-3-yl}-1H-imidazol-2-yl)-pyrrolidine tetrahydrochloride (4(1).4HCl). To a solution of compound 133 (0.159 g, 0.24 mmol) in 3.5 mL of dioxane, 3.5 mL of 4 M HCl solution in dioxane was added, the mixture was stirred for 15 h, and rotovapped to obtain 4(1), LC-MS (ESI) 473 (M+H)⁺.

Similarly, (S)-2-(5-{3'-tert-butyl-6-[4-((S)-2-pyrrolidin-2-yl-3H-imidazol-4-yl)-buta-1,3-diynyl]-biphenyl-3-yl}-1H-imidazol-2-yl)-pyrrolidine tetrahydrochloride (4(2).4HCl), LC-MS (ESI) 529 (M+H)⁺; (S)-2-(5-{6-[4-((S)-2-pyrrolidin-2-yl-3H-imidazol-4-yl)-buta-1,3-diynyl]-[1,1';3',1"]terphenyl-3-yl}-1H-imidazol-2-yl)-pyrrolidine tetrahydrochloride (4(3).4HCl), LC-MS (ESI) 549 (M+H)⁺; and (S)-2-(5-{3-naphthalen-2-yl-4-[4-((S)-2-pyrrolidin-2-yl-3H-imidazol-4-yl)-buta-1,3-diynyl]-phenyl}-1H-imidazol-2-yl)-pyrrolidine tetrahydrochloride (4(4).4HCl), LC-MS (ESI) 523 (M+H)⁺ were synthesized.

Example 13 (Scheme 19)

Synthesis of (S)-2-(5-{5-fluoro-6-[4-((S)-2-pyrrolidin-2-yl-3H-imidazol-4-yl)-buta-1,3-diynyl]-biphenyl-3-yl}-1H-imidazol-2-yl)-pyrrolidine tetrahydrochloride (4(5).4HCl) and (S)-2-(5-{5-methyl-6-[4-((S)-2-pyrrolidin-2-yl-3H-imidazol-4-yl)-buta-1,3-diynyl]-biphenyl-3-yl}-1H-imidazol-2-yl)-pyrrolidine tetrahydrochloride (4(6).4HCl)

tert-Butyl (S)-2-{5-[(5-{2-[(S)-1-(tert-butoxycarbonyl)pyrrolidin-2-yl]-1H-imidazol-5-yl}-3-fluorobiphenyl-2-yl)buta-1,3-diynyl]-1H-imidazol-2-yl}pyrrolidine-1-carboxylate (139), LC-MS (ESI) 691 (M+H)⁺ and tert-butyl (S)-2-{5-[(5-(2-[(S)-1-(tert-butoxycarbonyl)pyrrolidin-2-yl]-1H-imidazol-5-yl-3-methylbiphenyl-2-yl)buta-1,3-diynyl]-1H-imidazol-2-yl}pyrrolidine-1-carboxylate (140), LC-MS (ESI) 687 (M+H)⁺ were prepared starting from compounds 3(17), 3(20), and 139 using the above synthesis protocol for compounds 133-136 (Example 12). Compounds (4(5).4HCl), LC-MS (ESI) 491 (M+H)⁺ (4(6).4HCl), LC-MS (ESI) 486 (M+H)⁺ were obtained by analogy with the synthesis of compounds 4(1).4HCl-4(4).4HCl (Example 12).

Example 14 (Scheme 20)

Synthesis of {(S)-1-[(S)-2-(5-{3-aryl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-2-methyl-propyl}-carbamic acid methyl ester hydrochlorides (4(7).nHCl-4(18).nHCl)

Iodide 3(7)-3(16), 3(23), 3(24) (0.5 mmol), 1 mL of TEA, Pd(PPh₃)₄ (29 mg, 0.025 mmol), and CuI (10 mg, 0.05 mmol) were added to a solution of diyne 138 (in 4 mL of DMF) obtained like described above in Example 12 from compound 137 (0.268 g, 0.75 mmol), and the mixture was stirred under argon at 45° C. for 40 h. The mixture was diluted with DCM, filtered, washed with saturated NH₄Cl solution, rotovapped, and subjected to column chromatography on silica gel (EtOAc) or HPLC to afford tert-Butyl (S)-2-(5-{[2-aryl-4-(2-{(S)-1-[(S)-2-(methoxycarbonylamino)-3-methylbutanoyl]pyrrolidin-2-yl}-1H-imidazol-5-yl)phenyl]buta-1,3-diynyl}-1H-imidazol-2-yl)pyrrolidine-1-carboxylates 141-152 including tert-butyl (S)-2-(5-{[5-(2-{(S)-1-[(S)-2-(methoxycarbonylamino)-3-methylbutanoyl]pyrrolidin-2-yl}-1H-imidazol-5-yl)biphenyl-2-yl]buta-1,3-diynyl}-1H-imidazol-2-yl)pyrrolidine-1-carboxylate (141), LC-MS (ESI) 730 (M+H)⁺; tert-butyl (S)-2-(5-{[3'-methyl-5-(2-{(S)-1-[(S)-2-(methoxycarbonylamino)-3-methylbutanoyl]pyrrolidin-2- yl}-1H-imidazol-5-yl)biphenyl-2-yl]buta-1,3-diynyl}-1H-imidazol-2-yl)pyrrolidine-1-carboxylate (142), LC-MS (ESI) 786 (M+H)$^+$; tert-butyl (S)-2-(5-{[3'-fluoro-5-(2-{(S)-1-[(S)-2-(methoxycarbonylamino)-3-methylbutanoyl]pyrrolidin-2-yl}-1H-imidazol-5-yl)biphenyl-2-yl]buta-1,3-diynyl}-1H-imidazol-2-yl)pyrrolidine-1-carboxylate (143), LC-MS (ESI) 786 (M+H)$^+$; tert-butyl (S)-2-(5-{[3'-tert-butyl-5-(2-{(S)-1-[(S)-2-(methoxycarbonylamino)-3-methylbutanoyl]pyrrolidin-2-yl}-1H-imidazol-5-yl)biphenyl-2-yl]buta-1,3-diynyl}-1H-imidazol-2-yl)pyrrolidine-1-carboxylate (144), LC-MS (ESI) 786 (M+H)$^+$; tert-butyl (S)-2-(5-{[4'-tert-butyl-5-(2-{(S)-1-[(S)-2-(methoxycarbonylamino)-3-methylbutanoyl]pyrrolidin-2-yl}-1H-imidazol-5-yl)biphenyl-2-yl]buta-1,3-diynyl}-1H-imidazol-2-yl)pyrrolidine-1-carboxylate (145), LC-MS (ESI) 786 (M+H)$^+$; tert-butyl (S)-2-(5-{[5-(2-{(S)-1-[(S)-2-(methoxycarbonylamino)-3-methylbutanoyl]pyrrolidin-2-yl}-1H-imidazol-5-yl)-1,1':3',1''-terphenyl-2-yl]buta-1,3-diynyl}-1H-imidazol-2-yl)pyrrolidine-1-carboxylate (146), LC-MS (ESI) 806 (M+H)$^+$; tert-butyl (S)-2-(5-{[5-(2-{(S)-1-[(S)-2-(methoxycarbonylamino)-3-methylbutanoyl]pyrrolidin-2-yl}-1H-imidazol-5-yl)-1,1':4',1''-terphenyl-2-yl]buta-1,3-diynyl}-1H-imidazol-2-yl)pyrrolidine-1-carboxylate (147), LC-MS (ESI) 806 (M+H)$^+$; tert-butyl (S)-2-(5-{[4'-(dimethylamino)-5-(2-{(S)-1-[(S)-2-(methoxycarbonylamino)-3-methylbutanoyl]pyrrolidin-2-yl}-1H-imidazol-5-yl)biphenyl-2-yl]buta-1,3-diynyl}-1H-imidazol-2-yl)pyrrolidine-1-carboxylate (148), LC-MS (ESI) 773 (M+H)$^+$; tert-butyl (S)-2-(5-{[5-(2-{(S)-1-[(S)-2-(methoxycarbonylamino)-3-methylbutanoyl]pyrrolidin-2-yl}-1H-imidazol-5-yl)-4'-(4-methylpiperazin-1-yl)biphenyl-2-yl]buta-1,3-diynyl}-1H-imidazol-2-yl)pyrrolidine-1-carboxylate (149), LC-MS (ESI) 828 (M+H)$^+$; tert-butyl (S)-2-(5-{[4-(2-{(S)-1-[(S)-2-(methoxycarbonylamino)-3-methylbutanoyl]pyrrolidin-2-yl}-1H-imidazol-5-yl)-2-(pyridin-3-yl)phenyl]buta-1,3-diynyl}-1H-imidazol-2-yl)pyrrolidine-1-carboxylate (150), LC-MS (ESI) 731 (M+H)$^+$; tert-butyl (S)-2-{5-[4-(3-fluoro-5-{2-[(S)-1-((S)-2-methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carboxylate (151), LC-MS (ESI) 748 (M+H)$^+$; and tert-butyl (S)-2-{5-[4-(3-methyl-5-{2-[(S)-1-((S)-2-methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carboxylate (152), LC-MS (ESI) 744 (M+H)$^+$.

To a solution of compound 141-152 (0.2 mmol) in 3 mL of dioxane, 3 mL of 4 M HCl solution in dioxane was added, and the mixture was stirred for 3 h, then rotovapped to obtain {(S)-1-[(S)-2-(5-{3-aryl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-2-methyl-propyl}-carbamic acid methyl ester hydrochlorides ((4(7)-4(18)).nHCl), including: {(S)-2-methyl-1-[(S)-2-(5-{6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester trihydrochloride (4(7).3HCl), LC-MS (ESI) 630 (M+H)$^+$; {(S)-2-methyl-1-[(S)-2-(5-{2'-methyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester trihydrochloride (4(8).3HCl), LC-MS (ESI) 644 (M+H)$^+$; {(S)-1-[(S)-2-(5-{2'-fluoro-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(9).3HCl), LC-MS (ESI) 648 (M+H)$^+$; {(S)-1-[(S)-2-(5-{3'-tert-butyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(10).3HCl), LC-MS (ESI) 686 (M+H)$^+$; {(S)-1-[(S)-2-(5-{3'-tert-butyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester trihydrochloride (4(11).3HCl), LC-MS (ESI) 686 (M+H)$^+$; {(S)-2-methyl-1-[(S)-2-(5-{6-[4-((S)-2-pyrrolidin-2-yl-3H-imidazol-4-yl)-buta-1,3-diynyl]-[1,1';3',1'']terphenyl-3-yl}-1H-imidazol-2-yl)-pyrrolidine-1-carbonyl]-propyl}-carbamic acid methyl ester trihydrochloride (4(12).3HCl), LC-MS (ESI) 706 (M+H)$^+$; {(S)-2-methyl-1-[(S)-2-(5-{6-[4-((S)-2-pyrrolidin-2-yl-3H-imidazol-4-yl)-buta-1,3-diynyl]-[1,1';4',1'']terphenyl-3-yl}-1H-imidazol-2-yl)-pyrrolidine-1-carbonyl]-propyl}-carbamic acid methyl ester trihydrochloride (4(13).3HCl), LC-MS (ESI) 706 (M+H)$^+$; {(S)-1-[(S)-2-(5-{4'-dimethylamino-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl ester tetrahydrochloride (4(14).4HCl), LC-MS (ESI) 673 (M+H)$^+$; {(S)-2-methyl-1-[(S)-2-(5-{4'-(4-methyl-piperazin-1-yl)-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester pentahydrochloride (4(15).5HCl), LC-MS (ESI) 728 (M+H)$^+$; {(S)-2-methyl-1-[(S)-2-(5-{3-pyridin-3-yl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester tetrahydrochloride (4(16).4HCl), LC-MS (ESI) 631 (M+H)$^+$; {(S)-1-[(S)-2-(5-{5-fluoro-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-2-methyl-propyl}-carbamic acid methyl estertrihydrochloride (4(17).3HCl), LC-MS (ESI) 648 (M+H)$^+$; and methyl {(S)-2-methyl-1-[(S)-2-(5-{5-methyl-6-[4-((S)-2-pyrrolidin-2-yl-3H-imidazol-4-yl)-buta-1,3-diynyl]-biphenyl-3-yl}-1H-imidazol-2-yl)-pyrrolidine-1-carbonyl]-propyl}-carbamic acid methyl ester trihydrochloride (4(18).3HCl), LC-MS (ESI) 644 (M+H)$^+$.

Example 15 (Scheme 21)

Synthesis of {(S)-2-methyl-1-[(S)-2-(5-{4-[5-((S)-2-pyrrolidin-2-yl-3H-imidazol-4-yl)-biphenyl-2-yl]-buta-1,3-diynyl}-1H-imidazol-2-yl)-pyrrolidine-1-carbonyl]-propyl}-carbamic acid methyl ester trihydrochloride (4(19).3HCl)

To a solution of compound 153 (0.76 g, 2.13 mmol) in 8 mL of DCM, 8 mL of TFA was added, and the mixture was stirred for 4 h, then rotovapped to obtain (S)-2-(pyrrolidin-2-yl)-5-[(trimethylsilyl)buta-1,3-diynyl]-1H-imidazole trifluoroacetate (153.CF$_3$CO$_2$H), LC-MS (ESI) 258 (M+H)$^+$. To a solution of the above in 12 mL of DMF, N-Moc-L-valine (0.41 g, 2.34 mmol), HATU (0.89 g, 2.34 mmol), and TEA (1.48 mL, 10.6 mmol) were added, and the mixture was stirred in a fridge for 4 h. The mixture was diluted with benzene, washed with 5% citric acid solution, dried over Na$_2$SO$_4$, rotovapped, and subjected to column chromatography on SiO$_2$ (eluent hexane:EtOAc 1:3) to afford 0.655 g of (S)-3-methyl-1-oxo-1-((S)-2-{5-[(trimethylsilyl)buta-1,3-diynyl]-1H-imidazol-2-yl}pyrrolidin-1-yl)butan-2-ylcarbamate (154), LC-MS (ESI) 415 (M+H)$^+$. By analogy with the synthesis of diynes 3(35)-3(38) (Example 11), the resulting product 154 was converted into methyl (S)-3-methyl-1-oxo-1-((S)-2-[5-(buta-1,3-diynyl)-1H-imidazol-2-yl]pyrrolidin-1-yl)butan-2-ylcarbamate (155), LC-MS (ESI) 343 (M+H)+, which, by analogy with the synthesis of compounds 133-136 (Example 12), by reaction with 3(1) gave tert-butyl (S)-2-{5-[6-(4-{2-[(S)-1-((S)-2-methoxycarbonylamino-3-methyl-butyryl)-pyrrolidin-2-yl]-3H-imidazol-4-yl}-buta-1,3-diynyl)-biphenyl-3-yl]-1H-imidazol-2-yl}-pyrrolidine-1-carboxylate (156), LC-MS (ESI) 730 (M+H)+. The latter, by analogy with the synthesis of compounds 4(1).4HCl-4(4).4HCl (Example 12), was converted to intermediate 4(19).3HCl, LC-MS (ESI) 630 (M+H)+.

Example 16 (Scheme 22)

Synthesis of substituted {(5)-1-[(S)-2-(5-{4-[4-((S)-2-pyrrolidin-2-yl-3H-imidazol-4-yl)-buta-1,3-diynyl]-phenyl}-1H-imidazol-2-yl)-pyrrolidine-1-carbonyl]-2-methyl-propyl}-carbamic acid methyl ester hydrochlorides ((4(20)-4(22)).nHCl)

Intermediates (4(20)-4(22)).nHCl were prepared according to the protocol described above for intermediates (4(7)-4(18)).nHCl (Example 14) to obtain {(S)-2-Methyl-1-[(S)-2-(5-{3-phenoxy-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester trihydrochloride (4(20).3HCl), LC-MS (ESI) (m/z): 646 (100) (M+H)+; {(S)-2-methyl-1-[(S)-2-(5-{3-phenyl sulfanyl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester trihydrochloride (4(21).3HCl), LC-MS (ESI) (m/z): 662 (M+H)+; and {(S)-2-methyl-1-[(S)-2-(5-{3-(methyl-phenyl-amino)-4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester tetrahydrochloride (4(22).4HCl), LC-MS (ESI) (m/z): 659 (M+H)+.

Example 17 (Scheme 23)

Synthesis of substituted [(S)-2-methyl-1-((S)-2-{5-[4'-((S)-2-pyrrolidin-2-yl-3H-imidazol-4-yl)-biphenyl-4-yl]-1H-imidazol-2-yl}-pyrrolidine-1-carbonyl)-propyl]-carbamic acid methyl ester hydrochlorides (4(23)-4(28).nHCl)

A mixture of iodide 3(7), 3(23), 3(24), 3(26), 3(29), or 3(30) (0.85 mmol), (S)-2-{5-[4-(4,4,5,5-tetramethyl-[1,3,2]-dioxaboran-2-yl)-phenyl]-imidazol-2-yl}-pyrrolidine-1-carboxylic acid tert-butyl ester (162) (0.4 g, 0.89 mmol) in 12 mL of EtOH, and a solution of Na$_2$CO$_3$ in 3 mL of H$_2$O was stirred under N$_2$ for 15 min, then tetrakis triphenylphosphine palladium (50 mg) was added, and the reaction mixture was stirred at 80° C. for 15 h. The mixture was concentrated in vacuo, and the residue was partitioned between EtOAc and water. The organic layer was washed successively with water and brine, dried over Na$_2$SO$_4$, and concentrated to a compound, which was purified by silica gel column chromatography using hexane-ethyl acetate as eluent (0.45 g, 68%) to obtain 163-168 yielding 65-89% including tert-butyl (S)-2-[5-(4'-{2-[(S)-1-((S)-2-methoxycarbonylamino-3-methyl-butyryl)-pyrrolidin-2-yl]-3H-imidazol-4-yl}-[1,1';2',1"]terphenyl-4-yl)-1H-imidazol-2-yl]-pyrrolidine-1-carboxylate (163), LC-MS (ESI) (m/z, relative intensity): 758.2 (60) (M+H)+, 702.3 (70), 658.7 (65), 589.3 (85), 415.5 (100); tert-butyl (S)-2-[5-(4'-{2-[(S)-1-((S)-2-methoxycarbonylamino-3-methyl-butyryl)-pyrrolidin-2-yl]-3H-imidazol-4-yl}-2'-phenoxy-biphenyl-4-yl)-1H-imidazol-2-yl]-pyrrolidine-1-carboxylate (164), $^1$H-NMR (DMSO-d$_6$, 400 MHz): 11.8-11.5 (m, 2H), 7.78-7.60 (m, 3H), 7.55-7.40 (m, 6H), 7.29 (dd, J$_1$=J$_2$=7.6 Hz, 2H), 7.18 (d, J=8.4 Hz, 1H), 7.00 (dd, J$_1$=J$_2$=7.4 Hz, 1H), 6.89 (d, J=7.9 Hz, 2H), 5.05-5.01 (m, 1H), 4.82-4.71 (m, 1H), 4.07-4.00 (m, 2H), 3.79-3.71 (m, 2H), 3.52 (s, 3H), 3.40-3.33 (m, 2H), 2.28-2.08 (m, 2H), 1.95-1.80 (m, 4H), 1.41, 1.15 (2×m, 9H), 1.20-1.15 (m, 2H), 0.81-0.76 (m, 6H); tert-butyl (S)-2-[5-(4'-{2-[(S)-1-((S)-2-methoxycarbonylamino-3-methyl-butyryl)-pyrrolidin-2-yl]-3H-imidazol-4-yl}-2'-phenylsulfanyl-biphenyl-4-yl)-1H-imidazol-2-yl]-pyrrolidine-1-carboxylate (165), LC-MS (ESI) (m/z) 790.5 (M+H)+, $^1$H-NMR (DMSO-d$_6$, 400 MHz): 11.9-11.73 (m, 2H), 7.82-7.66 (m, 4H), 7.52-7.42 (m, 2H), 7.40-7.09 (m, 9H), 5.07-4.98 (m, 1H), 4.90-4.73 (m, 1H), 4.05-3.96 (m, 1H), 3.84-3.66 (m, 2H), 3.60-3.46 (m, 4H), 3.42-3.32 (m, 2H), 2.28-1.78 (m, 8H), 1.40, 1.16 (2×br.s, 9H), 0.84-0.75 (m, 6H); tert-butyl (S)-2-{5-[4'-{2-[(S)-1-((S)-2-methoxycarbonylamino-3-methyl-butyryl)-pyrrolidin-2-yl]-3H-imidazol-4-yl}-2'-(methyl-phenyl-amino)-biphenyl-4-yl]-1H-imidazol-2-yl}-pyrrolidine-1-carboxylate (166), LC-MS (ESI) (m/z, relative intensity) 787.8 (80) (M+H)+, 461.3 (90), 444.0 (75), 392.3 (100), $^1$H-NMR (DMSO-d$_6$, 400 MHz): 12.21-11.70 (m, 2H), 7.77-7.61 (m, 3H), 7.6-7.56 (m, 1H), 7.55-7.48 (m, 1H), 7.44 (d, J=8.4 Hz, 2H), 7.29 (d, J=7.6 Hz, 2H), 7.22 (d, J=8.4 Hz, 1H), 7.11 (dd, J$_1$=J$_2$=7.6 Hz, 2H), 6.67-6.54 (m, 3H), 5.23-4.99 (m, 1H), 4.86-4.7 (m, 1H), 4.02 (dd, J$_1$=J$_2$=8.4 Hz, 1H), 3.84-3.68 (m, 2H), 3.52 (s, 3H), 3.51-3.45 (m, 1H), 3.38-3.33 (m, 1H), 2.90 (s, 3H), 2.27-2.03 (m, 3H), 2.02-1.76 (m, 6H), 1.39, 1.15 (2×br.s, 9H), 0.90-0.74 (m, 6H); tert-butyl (S)-2-[5-(3'-fluoro-5'-{2-[(S)-1-((S)-2-methoxycarbonylamino-3-methyl-butyryl)-pyrrolidin-2-yl]-3H-imidazol-4-yl}-[1,1';2',1"]terphenyl-4"-yl)-1H-imidazol-2-yl]-pyrrolidine-1-carboxylate (167), LC-MS (ESI) (m/z) 776 (M+H)+. and tert-butyl (S)-2-[5-(3'-methyl-5'-{2-[(S)-1-((S)-2-methoxycarbonylamino-3-methyl-butyryl)-pyrrolidin-2-yl]-3H-imidazol-4-yl}-[1,1';2',1"]terphenyl-4"-yl)-1H-imidazol-2-yl]-pyrrolidine-1-carboxylate (168), LC-MS (ESI) (m/z) 772 (M+H)+.

To a solution of compounds 163-168 (5.8 mmol) in 5 ml of dioxane, a solution of 5 ml 4 M HCl in dioxane was added, and the mixture was stirred for 2 h and then evaporated to obtain [(S)-2-methyl-1-((S)-2-{5-[4-((S)-2-pyrrolidin-2-yl-3H-imidazol-4-yl)-[1,1';2',1"]terphenyl-4'-yl]-1H-imidazol-2-yl}-pyrrolidine-1-carbonyl)-propyl]-carbamic acid methyl ester trihydrochloride (4(23).3HCl), LC-MS (ESI) (m/z, relative intensity): 658.8 (100) (M+H)+, 589.3 (40), 484.0 (20), 415.5 (45); [(S)-2-methyl-1-((S)-2-{5-[2-phenoxy-4'-((S)-2-pyrrolidin-2-yl-3H-imidazol-4-yl)-biphenyl-4-yl]-1H-imidazol-2-yl}-pyrrolidine-1-carbonyl)-propyl]-carbamic acid methyl ester trihydrochloride (4(24).3HCl), LC-MS (ESI) (m/z, relative intensity): 674.3 (45) (M+H)+, 605.5 (25), 337.9 (100); [(S)-2-methyl-1-((S)-2-{5-[2-phenylsulfanyl-4'-((S)-2-pyrrolidin-2-yl-3H-imidazol-4-yl)-biphenyl-4-yl]-1H-imidazol-2-yl}-pyrrolidine-1-carbonyl)-propyl]-carbamic acid methyl ester trihydrochloride (4(25).3HCl), LC-MS (ESI) (m/z): 690 (M+H)+; [(S)-2-methyl-1-((S)-2-{5-[2-(methyl-phenyl-amino)-4'-((S)-2-pyrrolidin-2-yl-3H-imidazol-4-yl)-biphenyl-4-yl]-1H-imidazol-2-yl}-pyrrolidine-1-carbonyl)-propyl]-carbamic acid methyl ester tetrahydrochloride (4(26).4HCl), LC-MS (ESI) (m/z, relative intensity): 687.8 (100) (M+H)+, 618.7 (40), 444.8 (55), 428.0 (50); [(S)-{4-((S)-2-[5-6'-fluoro-4-((S)-2-pyrrolidin-2-yl-3H-imidazol-4-yl)-[1,1';2',1"]terphenyl-4'-yl]-1H-imidazol-2-yl}-pyrrolidine-1-carbonyl)-2-methyl-propyl]-carbamic acid methyl ester trihydrochloride (4(27)).3HCl), LC-MS (ESI) (m/z) 672 (M+H)$^+$, and [(S)-2-methyl-1-((S)-2-{5-[6'-methyl-4-((S)-2-pyrrolidin-2-yl-3H-imidazol-4-yl)-[1,1';2',1'']terphenyl-4'-yl]-1H-imidazol-2-yl}-pyrrolidine-1-carbonyl)-propyl]-carbamic acid methyl ester trihydrochloride (4(28)).3HCl), LC-MS (ESI) (m/z) 676 (M+H)$^+$.

Example 18 (Scheme 1)

Synthesis of [(S)-1-((S)-2-{5-[(5-{2-[(S)-1-((S)-2-methoxycarbonylamino-3-methylbutyryl)pyrrolidin-2-yl]-1H-imidazol-5-yl}biphenyl-2-yl)buta-1,3-diynyl]-1H-imidazol-2-yl}pyrrolidine-1-carbonyl)-2-methylpropyl]-carbamic acid methyl ester dihydrochlorides ((2(1)-2(6)).2HCl) and dimesilates (2(1), 2(4)).2CH$_3$SO$_3$H To the solution of (S)-2-{5-[(4-{2-[(S)-pyrrolidin-2-yl]-1H-imidazol-5-yl}-(2-arylphenyl)buta-1,3-diynyl]-1H-imidazol-2-yl}pyrrolidine tetrahydrochlorides (4(1)-4(6)). 3HCl) in 5 mL of DMF, N-Moc-L-valine (91 mg, 0.52 mmol), HATU (225 mg, 0.59 mmol), and DIPEA (0.412 mL, 2.36 mmol) were added, and the mixture was stirred in a fridge for 4 h. The mixture was diluted with DCM, washed with a 5% citric acid solution, dried over Na$_2$SO$_4$, rotovapped, and subjected to HPLC to afford compounds 2(1)-2(6) (yield 61-65%). Dihydrochlorides (2(1)-2(6)). 2HCl were obtained by addition of excess amounts of a 4 M HCl solution in dioxane to a solution of the base in acetone. [(S)-1-((S)-2-{5-[4-(5-{2-[(S)-1-((S)-2-Methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(1).2HCl), LC-MS (ESI) 787 (M+H)$^+$, and dimesilate 2(1).2CH$_3$SO$_3$H, LC-MS (ESI) 787 (M+H)$^+$; [(S)-1-((S)-2-{5-[4-(5-{2-[(S)-1-((S)-2-methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester naphtalene-1,5-disulfonate (2(2). 2HCl), LC-MS (ESI) 844 (M+H)$^+$, [(S)-1-((S)-2-{5-[4-(5-(2-[(S)-1-((S)-2-methoxycarbonylamino-3-methyl-butyryl)-pyrrolidin-2-yl]-3H-imidazol-4-yl]-[1,1';3',1'']terphenyl-2-yl)-buta-1,3-diynyl]-1H-imidazol-2-yl}-pyrrolidine-1-carbonyl)-2-methyl-propyl]-carbamic acid methyl ester dihydrochloride (2(3).2HCl), LC-MS (ESI) 864 (M+H)$^+$, [(S)-1-((S)-2-{5-[4-(5-{2-[(S)-1-((S)-2-methoxycarbonylamino-3-methyl-butyryl)-pyrrolidin-2-yl]-3H-imidazol-4-yl]-[1,1';3',1'']terphenyl-2-yl)-buta-1,3-diynyl]-1H-imidazol-2-yl}-pyrrolidine-1-carbonyl)-2-methyl-propyl]-carbamic acid methyl ester dihydrochloride (2(4).2HCl), LC-MS (ESI) 837 (M+H)$^+$ and dimesilate 2(4).2CH$_3$SO$_3$H, LC-MS (ESI) 837 (M+H)$^+$; [(S)-1-((S)-2-{5-[4-(2-fluoro-4-{2-[(S)-1-((S)-2-methoxycarbonylamino-3-methyl-butyryl)-pyrrolidin-2-yl]-3H-imidazol-4-yl}-phenyl)-buta-1,3-diynyl]-1H-imidazol-2-yl}-pyrrolidine-1-carbonyl)-2-methyl-propyl]-carbamic acid methyl ester dihydrochloride (2(5).2HCl), LC-MS (ESI) 805 (M+H)$^+$, and [(S)-1-((S)-2-{5-[4-(4-{2-[(S)-1-((S)-2-methoxycarbonylamino-3-methyl-butyryl)-pyrrolidin-2-yl]-3H-imidazol-4-yl}-2-methyl-phenyl)-buta-1,3-diynyl]-1H-imidazol-2-yl}-pyrrolidine-1-carbonyl)-2-methyl-propyl]-carbamic acid methyl ester dihydrochloride (2(6).2HCl), LC-MS (ESI) 801 (M+H)$^+$.

Example 19 (Scheme 2)

Synthesis of [(S)-1-((S)-2-{5-[4-(4-{2-[(S)-1-((R)-2-methoxycarbonylamino-2-phenyl-acetyl)-pyrrolidin-2-yl]-3H-imidazol-4-yl}-buta-1,3-diynyl)-phenyl]-1H-imidazol-2-yl}-pyrrolidine-1-carbonyl)-2-methyl-propyl]-carbamic acid methyl ester hydrochlorides ((2(7)-2(21)).nHCl)

To a solution of {(S)-1-[(S)-2-(5-{3-aryl-4-[4-((S)-2-pyrrolidin-2-yl-3H-imidazol-4-yl)-buta-1,3-diynyl]-phenyl}-1H-imidazol-2-yl)-pyrrolidine-1-carbonyl]-2-methyl-propyl}-carbamic acid methyl ester hydrochlorides ((4(7)-4(18), 4(20)-4(22).nHCl) (0.2 mmol) in 3 mL of DMF, N-Moc-(R)-phenylglycine (44 mg, 0.21 mmol) and HATU (91 mg, 0.24 mmol) were added, the mixture was cooled in a freezer to −20° C., than DIPEA (0.174 mL, 1 mmol) was added, and the mixture was stirred for homogeneity and kept in a freezer at −20° C. for 2 h. The mixture was diluted with DCM, washed with 5% citric acid solution, dried over Na$_2$SO$_4$, rotovapped, and subjected to HPLC to afford compound 2(7)-2(21). Hydrochlorides (2(7)-2(21)).nHCl were obtained by addition of excess amounts of a 4 M HCl solution in dioxane to a solution of the base in acetone to obtain [(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(7).2HCl), LC-MS (ESI) 821 (M+H)$^+$; [(S)-1-((S)-2-{5-[6-(4-{2-[(S)-1-((R)-2-methoxycarbonylamino-2-phenyl-acetyl)-pyrrolidin-2-yl]-3H-imidazol-4-yl}-buta-1,3-diynyl)-2'-methyl-biphenyl-3-yl]-1H-imidazol-2-yl}-pyrrolidine-1-carbonyl)-2-methyl-propyl]-carbamic acid methyl ester dihydrochloride (2(8).2HCl), LC-MS (ESI) 877 (M+H)$^+$; [(S)-1-((S)-2-{5-[2'-fluoro-6-(4-2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(9).2HCl), LC-MS (ESI) 877 (M+H)$^+$; [(S)-1-((S)-2-{5-[3'-tert-butyl-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(10).2HCl), LC-MS (ESI) 877 (M+H)$^+$; [(S)-1-((S)-2-{5-[4'-tert-butyl-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(11).2HCl). LC-MS (ESI) 877 (M+H)$^+$; [(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-[1,1';3',1'']terphenyl-3-yl]-1H-imidazol-2-yl}-pyrrolidine-1-carbonyl)-2-methyl-propyl]-carbamic acid methyl ester dihydrochloride (2(12).2HCl); LC-MS (ESI) 897 (M+H)$^+$; [(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-[1,1';4',1'']terphenyl-3-yl]-1H-imidazol-2-yl}-pyrrolidine-1-carbonyl)-2-methyl-propyl]-carbamic acid methyl ester dihydrochloride (2(13).2HCl). LC-MS (ESI) 897 (M+H)$^+$; [(S)-1-((S)-2-{5-[4'-dimethylamino-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester troihydrochloride (2(14).2HCl), LC-MS (ESI) 864 (M+H)+; [(S)-1-((S)-2-{5-[4'-(4-Methyl-piperazin-1-yl)-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester tetrahydrochloride (2(15).2HCl), LC-MS (ESI) 919 (M+H)+; [(S)-1-((S)-2-{5-[4-(4-{2-[(S)-1-((R)-2-methoxycarbonylamino-2-phenyl-acetyl)-pyrrolidin-2-yl]-3H-imidazol-4-yl}-buta-1,3-diynyl)-3-pyridin-3-yl-phenyl]-1H-imidazol-2-yl}-pyrrolidine-1-carbonyl)-2-methyl-propyl]-carbamic acid methyl ester trihydrochloride (2(16). 3HCl), LC-MS (ESI) 822 (M+H)+; [(S)-1-((S)-2-{5-[5-Fluoro-6-(4-{2-[(S)-1-((R)-2-methoxycarbonylamino-2-phenyl-acetyl)-pyrrolidin-2-yl]-3H-imidazol-4-yl}-buta-1, 3-diynyl)-biphenyl-3-yl]-1H-imidazol-2-yl}-pyrrolidine-1-carbonyl)-2-methyl-propyl]-carbamic acid methyl ester dihydrochloride (2(17).2HCl), LC-MS (ESI) 839 (M+H)+; [(S)-1-((S)-2-{5-[5-fluoro-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(18).2HCl), LC-MS (ESI) 835 (M+H)+; [(S)-1-((S)-2-{5-[4-(4-{2-[(S)-1-((R)-2-methoxycarbonylamino-2-phenyl-acetyl)-pyrrolidin-2-yl]-3H-imidazol-4-yl}-buta-1,3-diynyl)-3-phenoxy-phenyl]-1H-imidazol-2-yl}-pyrrolidine-1-carbonyl)-2-methyl-propyl]-carbamic acid methyl ester dihydrochloride (2(19). 2HCl), $^1$H-NMR (DMSO-$d_6$, 400 MHz): 15.2-14.4 (m, 4H), 8.20 (s, 1H), 7.92 (s, 1H), 7.90-7.80 (m, 2H), 7.68-7.58 (m, 2H), 7.42-7.30 (m, 7H), 7.24-7.18 (m, 2H), 7.04 (d, J=7.9 Hz, 2H), 5.48-5.44 (m, 1H), 5.14-5.08 (m, 1H), 4.10-4.05 (m, 2H), 3.95-3.80 (m, 4H), 3.51, 3.52 (2×s, 6H), 3.12-3.07 (m, 1H), 2.38-2.30 (m, 2H), 2.18-2.10 (m, 2H), 2.05-1.90 (m, 3H), 0.78, 0.72 (2×d, J=6.8 Hz, 6H). LC-MS (ESI) (m/z, relative intensity): 837.2 (60) (M+H)+, 419.4 (100); [(S)-1-((S)-2-{5-[4-(4-{2-[(S)-1-((R)-2-methoxycarbonylamino-2-phenyl-acetyl)-pyrrolidin-2-yl]-3H-imidazol-4-yl}-buta-1,3-diynyl)-3-phenoxy-phenyl]-1H-imidazol-2-yl}-pyrrolidine-1-carbonyl)-2-methyl-propyl]-carbamic acid methyl ester dihydrochloride (2(20).2HCl), $^1$H-NMR (DMSO-$d_6$, 400 MHz): 15.2-14.4 (m, 4H), 8.12 (s, 1H), 8.05 (s, 1H), 7.99-7.91 (m, 2H), 7.91-7.83 (m, 1H), 7.72-7.62 (m, 1H), 7.44-7.29 (m, 10H), 7.24 (d, J=8.7 Hz, 1H), 5.52-5.45 (m, 1H), 5.19-5.07 (m, 2H), 4.13-4.05 (m, 1H), 4.00-3.77 (m, 3H), 3.53, 3.52 (2×s, 6H), 3.18-3.05 (m, 1H), 2.39-2.26 (m, 2H), 2.22-1.90 (m, 6H), 1.89-1.76 (m, 1H), 0.79, 0.73 (2×d, J=6.7 Hz, 6H). LC-MS (ESI) (m/z): 853.3 (M+H)+; [(S)-1-((S)-2-{5-[4-(4-{2-[(S)-1-((R)-2-methoxycarbonylamino-2-phenyl-acetyl)-pyrrolidin-2-yl]-3H-imidazol-4-yl}-buta-1,3-diynyl)-3-(methyl-phenyl-amino)-phenyl]-1H-imidazol-2-yl}-pyrrolidine-1-carbonyl)-2-methyl-propyl]-carbamic acid methyl ester trihydrochloride (2(21).2HCl), $^1$H-NMR (DMSO-$d_6$, 400 MHz): 15.6-14.41 (m, 4H), 8.22 (s, 1H), 7.92-7.82 (m, 2H), 7.81-7.71 (m, 2H), 7.65 (d, J=7.6 Hz, 1H), 7.40-7.28 (m, 5H), 7.27-7.16 (m, 3H), 7.15-6.90 (m, 1H), 6.84 (t, J=6.8 Hz, 1H), 6.76 (d, J=8 Hz, 2H), 5.55-5.42 (m, 1H), 5.16-5.10 (m, 1H), 5.09-5.01 (m, 1H), 4.10 (dd, $J_1=J_2$=8.4 Hz, 1H), 3.99-3.89 (m, 1H), 3.87-3.78 (m, 2H), 3.60-3.47 (m, 1H), 3.53 (s, 3H), 3.52 (s, 3H), 3.14-3.04 (m, 1H), 2.41-2.29 (m, 1H), 2.25-1.87 (m, 8H), 1.86-1.75 (m, 1H), 0.80, 0.75 (2×d, J=6.4 Hz, 2×3H), LC-MS (ESI) (m/z, relative intensity): 850.5 (100) (M+H)+, 440.4 (30), 400.1 (30).

Example 20. (Scheme 3)

Synthesis of ((S)-1-{(S)-2-[5-(4'-{2-[(S)-1-((R)-2-methoxycarbonylamino-2-phenyl-acetyl)-pyrrolidin-2-yl]-3H-imidazol-4-yl}-biphenyl-4-yl)-1H-imidazol-2-yl]-pyrrolidine-1-carbonyl}-2-methyl-propyl)-carbamic acid methyl ester hydrochlorides ((2(22)-2 (27)).nHCl) (general procedure)

Inhibitors (2(22)-2(27)).nHCl were prepared from intermediates (4(25))-4(30)).nHCl and Moc-(R)-PhGly-OH similarly to inhibitors (2(7)-2(21)).nHCl described in Example 19. ((S)-1-{(S)-2-[5-(4-{2-[(S)-1-((R)-2-Methoxycarbonylamino-2-phenyl-acetyl)-pyrrolidin-2-yl]-3H-imidazol-4-yl}-[1,1';2',1"]terphenyl-4'-yl)-1H-imidazol-2-yl]-pyrrolidine-1-carbonyl}-2-methyl-propyl)-carbamic acid methyl ester dihydrochloride (2(22).2HCl), $^1$H-NMR (DMSO-$d_6$, 400 MHz): 15.2-14.4 (m, 4H, hydrochloride), 8.20 (s, 1H), 8.08 (s, 1H), 7.98 (d, J=7.2 Hz, Hz, 1H), 7.92 (s, 1H), 7.77 (d, J=8.4 Hz, 1H), 7.64 (d, J=7.5 Hz, 1H), 7.39-7.20 (m, 14H), 5.50 (d, J=8.2 Hz, 1H), 5.23-5.15 (m, 2H), 4.12 (dd, $J_1=J_2$=7.3 Hz, 1H), 4.00-3.92 (m, 2H), 3.88-3.82 (m, 1H), 3.55-3.52 (m, 1H), 3.54 (s, 3H), 3.50 (s, 3H), 3.17-3.11 (m, 1H), 2.43-2.35 (m, 1H), 2.25-2.15 (m, 2H), 2.10-1.95 (m, 4H), 1.90-1.84 (m, 1H), 0.83, 0.77 (2×d, J=6.7 Hz, 2×3H). LC-MS (ESI) (m/z, relative intensity): 849.5 (75) (M+H)+, 453.1 (40), 415.5 (100); ((S)-1-{(S)-2-[5-(4'-{2-[(S)-1-((R)-2-methoxycarbonylamino-2-phenyl-acetyl)-pyrrolidin-2-yl]-3H-imidazol-4-yl}-2-phenoxy-biphenyl-4-yl)-1H-imidazol-2-yl]-pyrrolidine-1-carbonyl}-2-methyl-propyl)-carbamic acid methyl ester dihydrochloride (2(23).2HCl), $^1$H-NMR (DMSO-$d_6$, 400 MHz): 15.30-14.30 (m, 4H), 8.20-8.05 (m, 1H), 7.90-7.70 (m, 2H), 7.70-7.52 (m, 5H), 7.40-7.20 (m, 10H), 7.02 (dd, $J_1=J_2$=7.4 Hz, 1H), 6.91 (d, J=7.8 Hz, 2H), 5.51-5.48 (m, 1H), 5.23-5.20 (m, 1H), 5.18-5.15 (m, 1H), 4.12-4.09 (m, 1H), 3.99-3.90 (m, 2H), 3.83-3.80 (m, 1H), 3.53, 3.50 (2×s, 6H), 3.18-3.12 (m, 1H), 2.40-2.32 (m, 1H), 2.26-2.24 (m, 2H), 2.18-2.13 (m, 2H), 2.05-1.96 (m, 3H), 1.90-1.83 (m, 1H), 0.80, 0.73 (2×d, J=6.8 Hz, 6H). LC-MS (ESI) (m/z, relative intensity): 865.2 (90) (M+H)+, 431.4 (100); ((S)-1-{(S)-2-[5-(4'-{2-[(S)-1-((R)-2-Methoxycarbonylamino-2-phenyl-acetyl)-pyrrolidin-2-yl]-3H-imidazol-4-yl}-2-phenylsulfanyl-biphenyl-4-yl)-1H-imidazol-2-yl]-pyrrolidine-1-carbonyl}-2-methyl-propyl)-carbamic acid methyl ester dihydrochloride (2(24).2HCl), $^1$H-NMR (DMSO-$d_6$, 400 MHz): 15.3-14.3 (m, 4H, hydrochloride), 8.12 (s, 1H), 8.03-7.95 (m, 2H), 7.87 (d, J=8.0 Hz, 1H), 7.74-7.58 (m, 2H), 7.54 (d, J=8.1 Hz, 1H), 7.43-7.15 (m, 10H), 7.08 (d, J=8.0 Hz, 1H), 5.51 (d, J=8.2 Hz, 1H), 5.27-5.18 (m, 1H), 5.16-5.09 (m, 1H), 4.13-4.09 (m, 1H), 4.01-3.78 (m, 3H), 3.54 (s, 3H), 3.51 (s, 3H), 3.22-3.10 (m, 1H), 2.43-2.22 (m, 3H), 2.21-2.08 (m, 2H), 2.10-1.95 (m, 5H), 1.90-1.84 (m, 2H), 0.79, 0.75 (2×d, J=6.8 Hz, 2×3H). LC-MS (ESI) (m/z): 881.5 (M+H)+; [(S)-1-((S)-2-{5-[4'-{2-[(S)-1-((R)-2-methoxycarbonylamino-2-phenyl-acetyl)-pyrrolidin-2-yl]-3H-imidazol-4-yl}-2-(methyl-phenyl-amino)-biphenyl-4-yl]-1H-imidazol-2-yl}-pyrrolidine-1-carbonyl)-2-methyl-propyl]-carbamic acid methyl ester trihydrochloride (2(25).3HCl), $^1$H-NMR (DMSO-$d_6$, 400 MHz): 15.36-14.0 (m, 5H), 8.20-8.12 (m, 1H), 8.07 (s, 1H), 7.91 (d, J=9 Hz, 1H), 7.87-7.79 (m, 3H), 7.73-7.59 (m, 2H), 7.50 (d, J=8 Hz, 2H), 7.41-7.29 (m, 5H), 7.26 (d, J=8.8 Hz, 1H), 7.12 (dd, $J_1=J_2$=7.2 Hz, 2H), 6.65 (dd, $J_1=J_2$=7.2 Hz, 1H), 6.58 (d, J=8 Hz, 2H), 5.53-5.34 (m, 1H), 5.24-5.17 (m, 1H), 5.13 (d, $J_1=J_2$=6.8 Hz, 1H), 4.10 (dd, $J_1=J_2$=8.4 Hz, 1H), 4.00-3.88 (m, 2H), 3.87-3.78 (m, 1H), 3.53 (s, 3H), 3.50 (s, 3H), 3.20-3.09 (m, 1H), 3.00 (s, 3H), 2.41-2.30 (m, 1H), 2.29-2.10 (m, 3H), 2.07-1.93 (m, 4H), 1.92-1.80 (m, 1H), 0.80, 0.75 (2×d, J=6.4 Hz, 2×3H), LC-MS (ESI) (m/z, relative intensity): 878.3 (100) (M+H)$^+$, 444.6 (60), 428.1 (50); ((S)-1-{(S)-2-[5-(6'-fluoro-4-{2-[(S)-1-((R)-2-methoxycarbonylamino-2-phenyl-acetyl)-pyrrolidin-2-yl]-3H-imidazol-4-yl}-[1,1';2',1"]terphenyl-4'-yl)-1H-imidazol-2-yl]-pyrrolidine-1-carbonyl}-2-methyl-propyl)-carbamic acid methyl ester dihydrochloride (2(26).2HCl), LC-MS (ESI) (m/z): 867 (M+H)$^+$; ((S)-1-{(S)-2-[5-(4-{2-[(S)-1-((R)-2-methoxycarbonylamino-2-phenyl-acetyl)-pyrrolidin-2-yl]-3H-imidazol-4-yl}-6'-methyl-[1,1';2',1"]terphenyl-4'-yl)-1H-imidazol-2-yl]-pyrrolidine-1-carbonyl-2-methyl-propyl)-carbamic acid methyl ester dihydrochloride (2(27).2HCl), LC-MS (ESI) (m/z): 863 (M+H)$^+$.

Example 21 (Scheme 4)

Synthesis of {(S)-1-[(S)-2-(5-{6-[(2-{(S)-1-[(S)-2-(methoxycarbonylamino)-2-phenylacetyl]pyrrolidin-2-yl}-1H-imidazol-5-yl)buta-1,3-diynyl]biphenyl-3-yl}-1H-imidazol-2-yl)pyrrolidine-1-carbonyl]-2-methylpropyl}-carbamic acid methyl ester dihydrochloride (2(28).2HCl)

Inhibitor 2(28).2HCl (LC-MS (ESI) 821 (M+H)$^+$) was prepared from the product of 4(7).3HCl and Moc-(S)-Ph-Gly-OH similarly to inhibitors (2(7)-2(21)).nHCl described in Example 19.

Example 22 (Scheme 5)

Synthesis of {(S)-1-[(S)-2-(5-{5-[(2-{(S)-1-[(S)-2-(methoxycarbonylamino)-2-phenylacetyl]pyrrolidin-2-yl}-1H-imidazol-5-yl)biphenyl-2-yl]buta-1,3-diynyl}-1H-imidazol-2-yl)pyrrolidine-1-carbonyl]-2-methylpropyl}-carbamic acid methyl ester dihydrochloride (2(29).2HCl) and {(S)-1-[(S)-2-(5-{5-[(2-{(S)-1-[(R)-2-(methoxycarbonylamino)-2-phenylacetyl]pyrrolidin-2-yl}-1H-imidazol-5-yl)biphenyl-2-yl]buta-1,3-diynyl}-1H-imidazol-2-yl)pyrrolidine-1-carbonyl]-2-methylpropyl}-carbamic acid methyl ester dihydrochloride (2(30).2HCl)

Inhibitors 2(29).2HCl and 2(30).2HCl were prepared from the product of 4(19).3HCl and Moc-(S)-PhGly-OH or Moc-(R)-PhGly-OH or similarly to inhibitors ((2(7)-2(21)).nHCl) described in Example 19. Inhibitors 2(29).2HCl and 2(30).2HCl have LC-MS (ESI) 821 (M+H)$^+$.

Example 23 (Scheme 6)

Synthesis of [(S)-1-((S)-2-{5-[4-(4-{2-[(S)-1-((S)-2-methoxycarbonylamino-3-methyl-butyryl)-pyrrolidin-2-yl]-3H-imidazol-4-yl}-buta-1,3-diynyl)-3-((R)-1-phenyl-ethoxy)-phenyl]-1H-imidazol-2-yl}-pyrrolidine-1-carbonyl)-2-methyl-propyl]-carbamic acid methyl ester dihydrochloride 2(31). Inhibitor 2(31) (LC-MS (ESI) 831 (M+H)$^+$) was prepared using the general procedure given above for compounds 141-152 (Example 14) and was used with compounds 3(25) and 155.

Example 24

Preparation of a pharmaceutical composition in the form of a tablet. Starch (1600 mg), ground lactose (1600 mg), talc (400 mg), and [(S)-1-((S)-2-{5-[6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(7).2HCl) (1000 mg) were mixed together and pressed into a bar. The resulting bar was comminuted into granules and sifted through a sieve to collect granules of 14-16 mesh. The granules thus obtained were shaped into tablets of a suitable form weighing 100-300 mg each.

Example 25

Preparation of a pharmaceutical composition in the form of capsules. [(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(7).2HCl) and lactose powder were carefully mixed in the ratio 2:1. The resultant powdery mixture was packed into gelatin capsules of a suitable size, 100-300 mg in each capsule.

Example 26

Preparation of a pharmaceutical composition in the form of compositions for intramuscular, intraperitoneal, or hypodermic injections. [(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(7).2HCl) (500 mg), chlorobutanol (300 mg), propylene glycol (2 ml), and injectable water (100 ml) were mixed together. The resultant solution was filtered, placed into 1 ml ampoules, and sealed.

Example 27

The HCV replicon assay was used to determine the antiviral activity of compounds of general formula 2 (test compounds). The test cell line used in the HCV Replicon Assay was the human hepatoma cell line Huh7 incorporating the HCV replicons synthesized by an outside vendor.

96-well plates were seeded with cells at a density of 7.5×10$^3$ cells per well in 50 µl of assay media. The compound stock solution was made up freshly in an assay medium (DMEM 1×, Cellgro; cat. #10-013-CV) as a 2× stock. A total of 11 serial 3-fold dilutions of test compounds were prepared from the 2× stock in the assay media ranging from 20 nM-0.2 pM final concentrations. At least 4 hours after seeding the cells, compound treatment was initiated by adding 50 µl of compound dilution to the plates. The final concentrations of compound therefore ranged from 10 nM to 0.1 pM when diluted 1:1 in culture media. The final DMSO concentration was 0.5%. Cells and inhibitors were incubated for 3 days at 37° C./5% CO$_2$. The media was removed from the plates by gentle tapping. The cells were fixed with 100 µl 1:1 acetone:methanol for 1 minute, washed three times with PBS buffer, and then blocked with 150 µl/well 10% Fetal Bovine Serum (FBS) in PBS for 1 hour at room temperature. The cells were then washed three times with PBS buffer and incubated with 100 µl/well anti-hepatitis C core mAb (Affinity BioReagents; cat. # MA1-080, 1 mg/ml stock diluted 1:4,000 in 10% FBS-PBS) for 2 hours at 37° C. Then, the cells were washed three times with PBS and incubated with 100 µl/well HRP-Goat Anti-Mouse antibody (diluted 1:3.500 in 10% FBS-PBS) for 1 hour at 37° C. The cells were then washed three times with PBS and developed with an OPD solution, 100 μl/well (1 OPD tablet+12 ml citrate/phosphate buffer+5 μl 30% $H_2O_2$ per plate), for 30 minutes in the dark at room temperature. The reaction was stopped with 2N $H_2SO_4$ (100 μl/well), and the absorbance was measured at $A_{490}$ X on a Victor³ V 1420 multilabel counter (Perkin Elmer). The $EC_{50}$ values were calculated for test compounds from the resulting best-fit equations determined by Xlfit software (Table 2 and 3).

The cytotoxicity of the test compounds was studied in parallel using the same cell line, Huh7. Cell viability was determined using the ATPLite Kit (Perkin-Elmer, Boston, USA), according to manufacturer's instructions. 96-well black/transparent bottom plates were seeded with cells at a density of $7.5 \times 10^3$ cells per well in 50 μl medium. After 18 hours, compound treatment was initiated by adding 50 μl of compound dilution into the plates. Each compound dilution was tested in triplicates. The cells and inhibitors were then incubated for 96 hours at 37° C./5% $CO_2$. The plates were washed twice with PBS (0.2 ml/well), and then lysed by adding lysis buffer, 0.05 ml/well (all reagents were included with the ATPLite Kit). After rocking for 5 min on a rocking platform, substrate buffer was added (0.05 ml/well). After additional 5-min incubation, the plates were kept in dark for 10 min, and the luminescence was read using TopCount NXT (Packard, Perkin Elmer). $CC_{50}$ values for all test compounds were determined using XLfit 4.1 software (Table 2).

INDUSTRIAL APPLICABILITY

The invention could be used in medicine, veterinary, biochemistry.

The invention claimed is:

1. A compound of general formula 2:

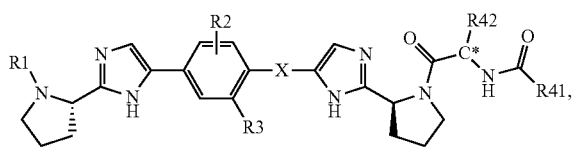

2 or a pharmaceutically acceptable salt, a hydrate, or a crystalline form, wherein:

R1 is
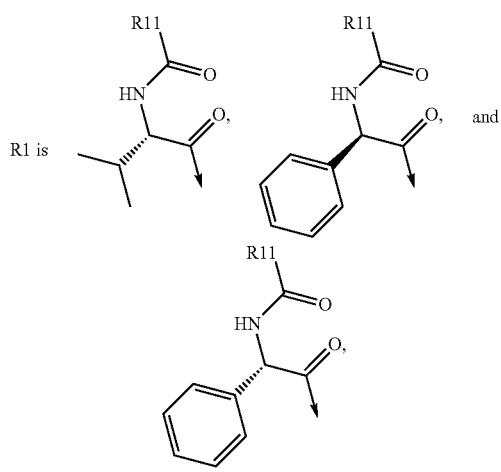
and

R2 is hydrogen, halogen, or $C_1$-$C_4$alkyl;

R3 is an optionally substituted aryl, an optionally substituted aryloxy, an optionally substituted arylsulfanyl, an optionally substituted arylamino, or an optionally substituted nitrogen hetaryl;

R11 and R41 are not necessarily the same, and an optionally substituted $C_1$-$C_6$ alkyl, an optionally substituted $C_3$-$C_6$ cycloalkyl, or an optionally substituted $C_1$-$C_6$ alkyloxy;

R42 is phenyl or isopropyl;

C* is (R) or (S) chiral carbon;

X is buta-1,3-diynylene or 1,4-phenylene; arrows (←) indicate the position of substituents attachment.

2. The compound according to claim 1 selected from the group of compounds 2(1)-2(33):

[(S)-1-((S)-2-{5-[4-(5-{2-((S)-1-((S)-2-Methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(1).2HCl),

[(S)-1-((S)-2-{5-[4-(5-{2-((S)-1-((S)-2-Methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dimesylate (2(1)-2CH_3SO_3H),

[(S)-1-((S)-2-{5-[4-(5-{2-[(S)-1-((S)-2-Methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester naphtalene-1,5-disulfonate (2(1).2CH_3SO_3H),

[(S)-1-((S)-2-{5-[4-(3'-tert-Butyl-5-{2-[(s)-1-((S)-2-methoxycarbonylamino-3-methyl-butyryl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(2).2HCl),

[(S)-1-((S)-2-{5-[4-(5-{2-[(S)-1-((S)-2-Methoxycarbonylamino-3-methyl-butyryl)-pyrrolidin-2-yl]-3H-imidazol-4-yl}-[1,1';3',1'']terphenyl-2-yl)-buta-1,3-diynyl]-1H-imidazol-2-yl}-pyrrolidine-1-carbonyl)-2-methyl-propyl]-carbamic acid methyl ester dihydrochloride (2(3).2HCl),

[(S)-1-((S)-2-{5-[4-(4-{2-[(S)-1-((S)-2-Methoxycarbonylamino-3-methyl-butyryl)-pyrrolidin-2-yl]-3H-imidazol-4-yl}-2-naphthalen-2-yl-phenyl)-buta-1,3-diynyl]-1H-imidazol-2-yl}-pyrrolidine-1-carbonyl)-2-methyl-propyl]-carbamic acid methyl ester dihydrochloride (2(4).2HCl),

[(S)-1-((S)-2-{5-[4-(2-Fluoro-4-{2-[(s)-1-((S)-2-methoxycarbonylamino-3-methyl-butyryl)-pyrrolidin-2-yl]-3H-imidazol-4-yl}-phenyl)-buta-1,3-diynyl]-1H-imidazol-2-yl}-pyrrolidine-1-carbonyl)-2-methyl-propyl]-carbamic acid methyl ester dihydrochloride (2(5).2HCl),

[(S)-1-((S)-2-{5-[4-(4-{2-[(S)-1-((S)-2-Methoxycarbonylamino-3-methyl-butyryl)-pyrrolidin-2-yl]-3H-imidazol-4-yl}-2-methyl-phenyl)-buta-1,3-diynyl]-1H-imidazol-2-yl}-pyrrolidine-1-carbonyl)-2-methyl-propyl]-carbamic acid methyl ester dihydrochloride (2(6).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(7).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-2'-methyl-biphenyl-3-yl]-1H-imidazol-2-yl}-pyrrolidine-1-carbonyl)-2-methyl-propyl]-carbamic acid methyl ester dihydrochloride (2(8).2HCl),

[(S)-1-((S)-2-{5-[2'-Fluoro-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(9).2HCl),

[(S)-1-((S)-2-{5-[3'-tert-Butyl-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(10).2HCl),

[(S)-1-((S)-2-{5-[4'-tert-Butyl-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(11).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-[1,1';3',1"]terphenyl-3-yl]-1H-imidazol-2-yl}-pyrrolidine-1-carbonyl)-2-methyl-propyl]-carbamic acid methyl ester dihydrochloride (2(12).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-[1,1';4',1"]terphenyl-3-yl]-1H-imidazol-2-yl}-pyrrolidine-1-carbonyl)-2-methyl-propyl]-carbamic acid methyl ester dihydrochloride (2(13).2HCl),

[(S)-1-((S)-2-{5-[4'-Dimethylamino-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester troihydrochloride (2(14).3HCl),

[(S)-1-((S)-2-{5-[4'-(4-Methyl-piperazin-1-yl)-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester tetrahydrochloride (2(15).4HCl),

[(S)-1-((S)-2-{5-[4-{2-[(S)-1-((R)-2-Methoxycarbonylamino-2-phenyl-acetyl)-pyrrolidin-2-yl]-3H-imidazol-4-yl}-buta-1,3-diynyl)-3-pyridin-3-yl-phenyl]-1H-imidazol-2-yl}-pyrrolidine-1-carbonyl)-2-methyl-propyl]-carbamic acid methyl ester trihydrochloride (2(16).3HCl),

[(S)-1-((S)-2-{5-[5-Fluoro-6-(4-{2-[(S)-1-((R)-2-methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(17).2HCl),

[(S)-1-((S)-2-{5-[6-(4-{2-[(S)-1-((R)-2-Methoxycarbonylamino-2-phenyl-acetyl)-pyrrolidin-2-yl]-3H-imidazol-4-yl}-buta-1,3-diynyl)-5-methyl-biphenyl-3-yl]-1H-imidazol-2-yl}-pyrrolidine-1-carbonyl)-2-methyl-propyl]-carbamic acid methyl ester dihydrochloride (2(18).2HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-phenoxy-phenyl]-1H-imidazol-2-yl}-pyrrolidine-1-carbonyl)-2-methyl-propyl]-carbamic acid methyl ester dihydrochloride (2(19).2HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-phenylsulfanyl-phenyl]-1H-imidazol-2-yl}-pyrrolidine-1-carbonyl)-2-methyl-propyl]-carbamic acid methyl ester dihydrochloride (2(20).2HCl),

[(S)-1-((S)-2-{5-[4-(4-{2-[(S)-1-((R)-2-Methoxycarbonylamino-2-phenyl-acetyl)-pyrrolidin-2-yl]-3H-imidazol-4-yl}-buta-1,3-diynyl)-3-(methyl-phenyl-amino)-phenyl]-1H-imidazol-2-yl}-pyrrolidine-1-carbonyl)-2-methyl-propyl]-carbamic acid methyl ester trihydrochloride (2(21).3HCl), ((S)-1-{(S)-2-[5-(4-{2-[(S)-1-((R)-2-Methoxycarbonylamino-2-phenyl-acetyl)-pyrrolidin-2-yl]-3H-imidazol-4-yl}-[1,1';2',1"]terphenyl-4'-yl)-1H-imidazol-2-yl]-pyrrolidine-1-carbonyl}-2-methyl-propyl)-carbamic acid methyl ester dihydrochloride (2(22).2HCl), ((S)-1-{(S)-2-[5-(4'-{2-[(S)-1-((R)-2-Methoxycarbonylamino-2-phenyl-acetyl)-pyrrolidin-2-yl]-3H-imidazol-4-yl}-2-phenoxy-biphenyl-4-yl)-1H-imidazol-2-yl]-pyrrolidine-1-carbonyl}-2-methyl-propyl)-carbamic acid methyl ester dihydrochloride (2(23).2HCl), ((S)-1-{(S)-2-[5-(4'-{2-[(S)-1-((R)-2-Methoxycarbonylamino-2-phenyl-acetyl)-pyrrolidin-2-yl]-3H-imidazol-4-yl}-2-phenylsulfanyl-biphenyl-4-yl)-1H-imidazol-2-yl]-pyrrolidine-1-carbonyl}-2-methyl-propyl)-carbamic acid methyl ester dihydrochloride (2(24).2HCl),

[(S)-1-((S)-2-{5-[4'-{2-[(S)-1-((R)-2-Methoxycarbonylamino-2-phenyl-acetyl)-pyrrolidin-2-yl]-3H-imidazol-4-yl}-2-(methyl-phenyl-amino)-biphenyl-4-yl]-1H-imidazol-2-yl}-pyrrolidine-1-carbonyl)-2-methyl-propyl]-carbamic acid methyl ester trihydrochloride (2(25).3HCl), ((S)-1-{(S)-2-[5-(6'-Fluoro-4-{2-[(S)-1-((R)-2-methoxycarbonylamino-2-phenyl-acetyl)-pyrrolidin-2-yl]-3H-imidazol-4-yl}-[1,1';2',1"]terphenyl-4'-yl)-1H-imidazol-2-yl]-pyrrolidine-1-carbonyl}-2-methyl-propyl)-carbamic acid methyl ester dihydrochloride (2(26).2HCl), ((S)-1-{(S)-2-[5-(4-{2-[(S)-1-((R)-2-Methoxycarbonylamino-2-phenyl-acetyl)-pyrrolidin-2-yl]-3H-imidazol-4-yl}-6'-methyl-[1,1';2',1"]terphenyl-4'-yl)-1H-imidazol-2-yl]-pyrrolidine-1-carbonyl}-2-methyl-propyl)-carbamic acid methyl ester dihydrochloride (2(27).2HCl),

[(S)-1-((S)-2-{5-[6-(4-{2-[(S)-1-((S)-2-Methoxycarbonylamino-2-phenyl-acetyl)-pyrrolidin-2-yl]-3H-imidazol-4-yl}-buta-1,3-diynyl)-biphenyl-3-yl]-1H-imidazol-2-yl}-pyrrolidine-1-carbonyl)-2-methyl-propyl]-carbamic acid methyl ester dihydrochloride (2(28).2HCl),

[(S)-1-((S)-2-{5-[4-(5-{2-[(S)-1-((S)-2-Methoxycarbonylamino-2-phenyl-acetyl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(29).2HCl),

[(S)-1-((S)-2-{5-[4-(5-{2-[(S)-1-((R)-2-Methoxycarbonylamino-2-phenyl-acetyl)-pyrrolidin-2-yl]-3H-imidazol-4-yl}-biphenyl-2-yl)-buta-1,3-diynyl]-1H-imidazol-2-yl}-pyrrolidine-1-carbonyl)-2-methyl-propyl]-carbamic acid methyl ester dihydrochloride (2(30).2HCl),

[(S)-1-((S)-2-{5-[4-(4-{2-[(S)-1-((S)-2-Methoxycarbonylamino-3-methyl-butyryl)-pyrrolidin-2-yl]-3H-imidazol-4-yl}-buta-1,3-diynyl)-3-((R)-1-phenyl-ethoxy)-phenyl]-1H-imidazol-2-yl}-pyrrolidine-1-carbonyl)-2-methyl-propyl]-carbamic acid methyl ester dihydrochloride (2(31).2HCl),

[(S)-1-((S)-2-{5-Benzyloxy-4-(4-{2-[(S)-1-((S)-2-methoxycarbonylamino-3-methyl-butyryl)-pyrrolidin-2-yl]-3H-imidazol-4-yl}-buta-1,3-diynyl)-phenyl]-1H-imidazol-2-yl}-pyrrolidine-1-carbonyl)-2-methyl-propyl]-carbamic acid methyl ester dihydrochloride (2(32).2HCl) and ((S)-1-{(S)-2-[5-(3'-Fluoro-5'-{2-((S)-1-((S)-2-methoxycarbonylamino-3-methyl-butyryl)-pyrrolidin-2-yl]-3H-imidazol-4-yl}-[1,1';2',1"]terphenyl-4"-yl)-1H-imidazol-2-yl]-pyrrolidine-1-carbonyl}-2-methyl-propyl)-carbamic acid methyl ester dihydrochloride (2(33).2HCl), or a pharmaceutically acceptable salt, a hydrate, or a crystalline form thereof.

3. A pharmaceutical composition comprising at least one compound according to claim 1 or 2 or a pharmaceutically acceptable salt, a hydrate, a crystalline form, or a stereoisomer thereof, in combination with a pharmaceutically acceptable carrier or excipient.

4. The pharmaceutical composition of claim 3, further comprising one or more agents selected from interferon, pegylated interferon, ribavirin, amantadine, an HCV protease inhibitor, an HCV polymerase inhibitor, an HCV helicase inhibitor, or an internal ribosome entry site inhibitor.

5. The pharmaceutical composition of claim 3, comprising a further comprising one or more an agents selected from interferon, pegylated interferon, ribavirin, NS3/4A, NS4A, NS4B, NS5B inhibitor, and an internal ribosome entry site inhibitor.

6. The pharmaceutical composition of claim 3, further comprising ribavirin and interferon or pegylated interferon.

7. The pharmaceutical composition of claim 3, further comprising NS3/4A, ribavirin and interferon or pegylated interferon.

8. The pharmaceutical composition of claim 3, further comprising an NS5B inhibitor.

9. The pharmaceutical composition of claim 3, further comprising a cytochrome P450 monoxygenase inhibitor.

10. The pharmaceutical composition of claim 9, wherein the cytochrome P450 monoxygenase inhibitor is ritonavir.

\* \* \* \* \*